(12) United States Patent
Lesh et al.

(10) Patent No.: US 7,089,063 B2
(45) Date of Patent: Aug. 8, 2006

(54) DEFLECTABLE TIP CATHETER WITH GUIDEWIRE TRACKING MECHANISM

(75) Inventors: Michael D. Lesh, Mill Valley, CA (US); Michael R. Ross, Hillsborough, CA (US); James C Peakcock, III, San Carlos, CA (US); Kevin J. Taylor, San Francisco, CA (US)

(73) Assignee: Atrionix, Inc., Palo Alto, CA (US)

( * ) Notice: Subject to any disclaimer, the term of this patent is extended or adjusted under 35 U.S.C. 154(b) by 342 days.

(21) Appl. No.: 09/858,523

(22) Filed: May 16, 2001

(65) Prior Publication Data

US 2002/0165535 A1 Nov. 7, 2002

Related U.S. Application Data

(60) Provisional application No. 60/205,009, filed on May 16, 2000.

(51) Int. Cl.
*A61F 2/00* (2006.01)

(52) U.S. Cl. .................. 607/101; 607/96; 607/122; 606/41

(58) Field of Classification Search .............. 606/41, 606/45–47, 7, 13, 15; 604/95; 607/101, 607/122, 102; 600/104, 139
See application file for complete search history.

(56) References Cited

U.S. PATENT DOCUMENTS

| | | | |
|---|---|---|---|
| 2,688,329 A | 9/1954 | Wallace | |
| 4,529,400 A | 7/1985 | Scholten | |
| 4,592,341 A * | 6/1986 | Omagari et al. | ............ 600/104 |
| 4,960,134 A | 10/1990 | Webster, Jr. | |
| 4,986,257 A | 1/1991 | Chikama | |
| 5,168,864 A | 12/1992 | Shockey | |
| 5,195,968 A | 3/1993 | Lundquist et al. | |
| 5,254,088 A | 10/1993 | Lundquist et al. | |
| 5,275,151 A | 1/1994 | Shockey et al. | |
| 5,318,525 A | 6/1994 | West et al. | |
| 5,368,557 A * | 11/1994 | Nita et al. | ...................... 601/2 |
| 5,395,328 A | 3/1995 | Ockuly et al. | |
| 5,395,329 A | 3/1995 | Fleischhackor et al. | |
| 5,397,304 A * | 3/1995 | Truckai | ...................... 604/528 |
| 5,437,636 A | 8/1995 | Snoke et al. | |
| 5,472,017 A | 12/1995 | Kovalcheck | |
| 5,487,757 A | 1/1996 | Truckai et al. | |
| 5,562,619 A | 10/1996 | Mirarchi et al. | |
| 5,609,606 A * | 3/1997 | O'Boyle | ...................... 606/194 |

(Continued)

FOREIGN PATENT DOCUMENTS

EP 0 667 126 A1 8/1995

(Continued)

*Primary Examiner*—Roy D. Gibson

(57) ABSTRACT

A deflectable tip catheter that is used in combination with a guidewire for delivery of an ablation element to target areas of a patient's vasculature. The deflectable tip catheter has a handle portion, an elongated shaft and a deflectable tip portion. A guidewire lumen extends through the elongated shaft and deflectable tip portion. A guidewire passes through the guidewire lumen and exits from a port in the distal end of the deflectable tip portion. The deflectable tip of the catheter is deflected by manipulation of the handle portion to direct the advancement of the guidewire as the guidewire is advanced out of the distal port. By using the deflectable tip portion to direct the advancement of the guidewire, the physician's ability to navigate sharp angles is greatly improved. The deflectable tip catheter is particularly suitable for delivering an ablation element to a pulmonary vein or pulmonary vein branch for performing circumferential ultrasound vein ablation to treat atrial fibrillation.

3 Claims, 38 Drawing Sheets

U.S. PATENT DOCUMENTS

| | | | |
|---|---|---|---|
| 5,676,653 A * | 10/1997 | Taylor et al. | 604/95.04 |
| 5,702,433 A * | 12/1997 | Taylor et al. | 607/101 |
| 5,755,760 A | 5/1998 | Maguire et al. | |
| 5,814,016 A | 9/1998 | Valley et al. | |
| 5,827,278 A | 10/1998 | Webster, Jr. | |
| 5,868,698 A | 2/1999 | Rowland et al. | |
| 5,876,373 A * | 3/1999 | Giba et al. | 604/103.1 |
| 5,882,333 A | 3/1999 | Schaer et al. | |
| 5,919,188 A | 7/1999 | Shearon et al. | |
| 5,964,757 A * | 10/1999 | Ponzi | 606/45 |
| 5,971,983 A * | 10/1999 | Lesh | 606/41 |
| 6,006,755 A * | 12/1999 | Edwards | 128/898 |
| 6,036,687 A | 3/2000 | Laufer et al. | |
| 6,042,581 A * | 3/2000 | Ryan et al. | 606/45 |
| 6,059,739 A | 5/2000 | Baumann | |
| 6,063,080 A | 5/2000 | Nelson et al. | |
| 6,063,082 A * | 5/2000 | DeVore et al. | 606/170 |
| 6,083,170 A | 7/2000 | Ben-Haim | |
| 6,083,222 A | 7/2000 | Klein et al. | |
| 6,283,959 B1 * | 9/2001 | Lalonde et al. | 606/21 |
| 6,290,697 B1 * | 9/2001 | Tu et al. | 606/27 |
| 6,325,797 B1 * | 12/2001 | Stewart et al. | 606/41 |
| 6,484,727 B1 * | 11/2002 | Vaska et al. | 128/898 |
| 6,602,276 B1 * | 8/2003 | Dobak et al. | 607/105 |
| 2003/0195510 A1 * | 10/2003 | Schaer | 606/41 |

FOREIGN PATENT DOCUMENTS

| | | |
|---|---|---|
| WO | WO 99/02096 A1 | 1/1999 |
| WO | WO 00/56237 A2 | 9/2000 |

* cited by examiner

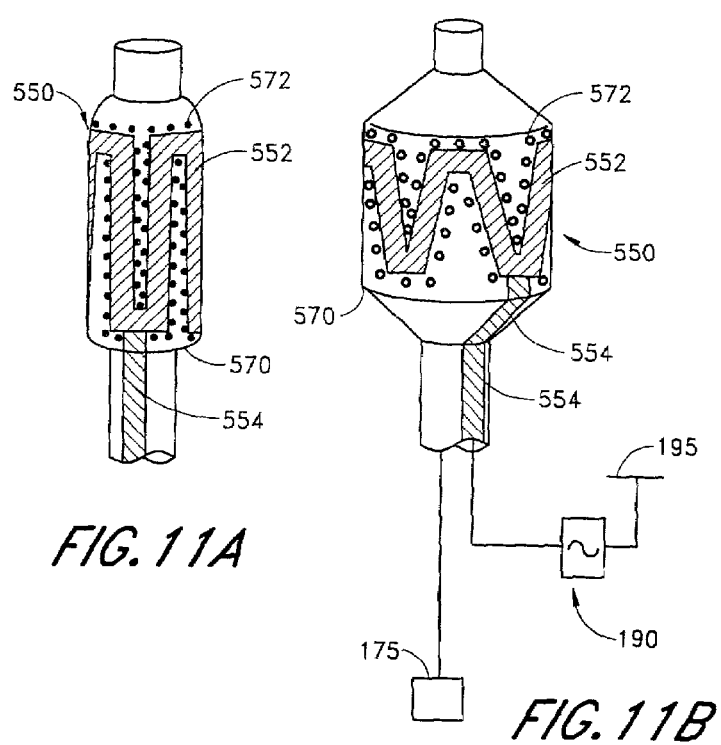
FIG.11A
FIG.11B
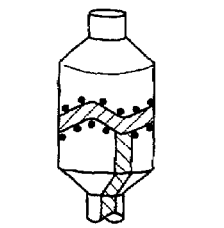
FIG.11C
FIG.11D
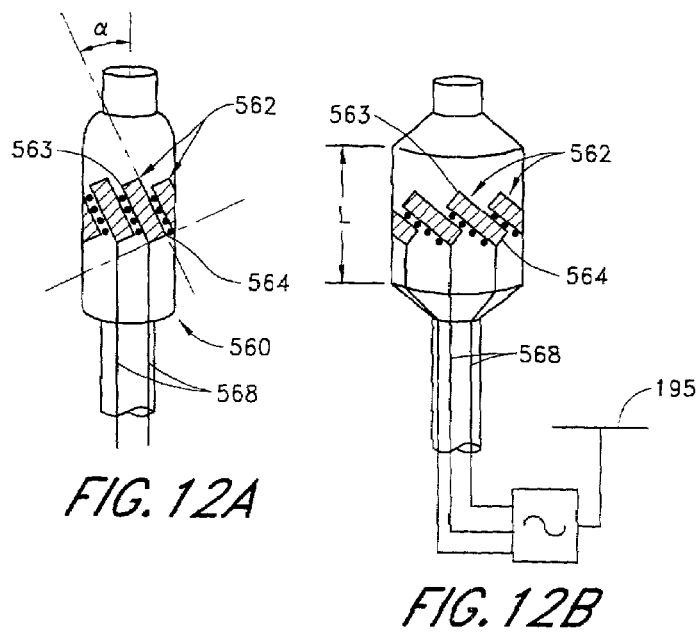
FIG.12A
FIG.12B

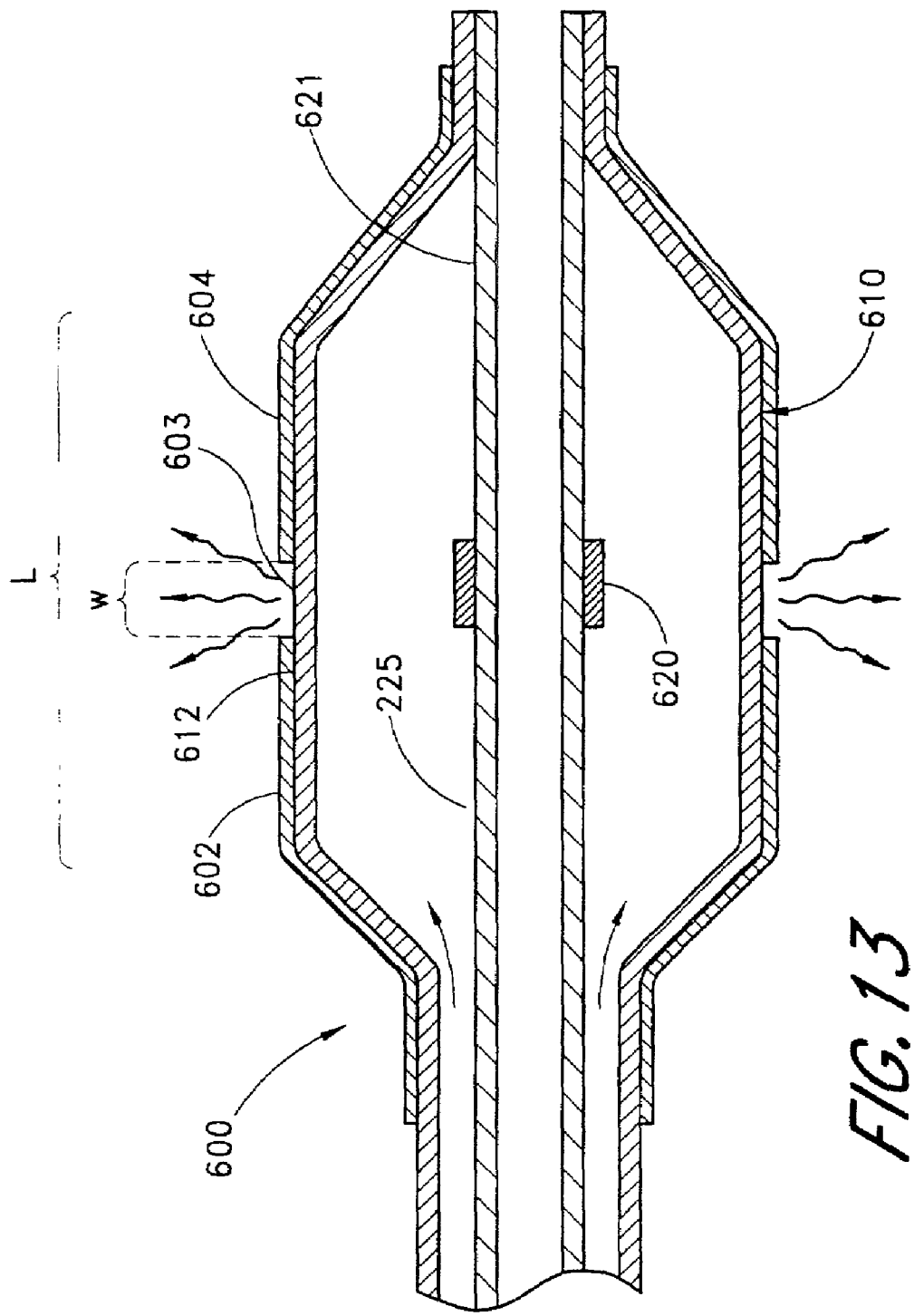

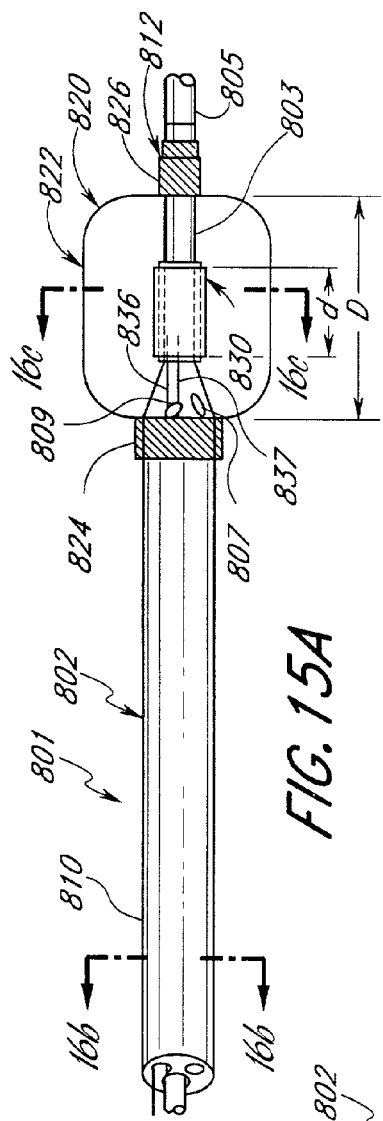
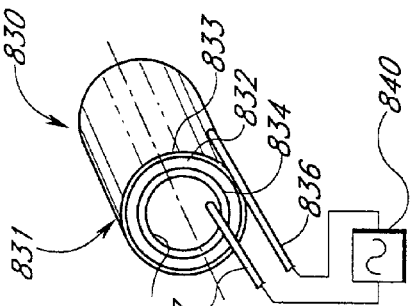
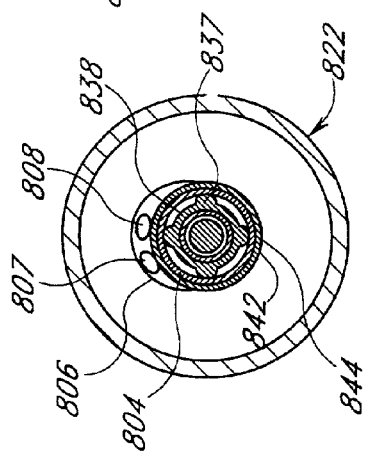
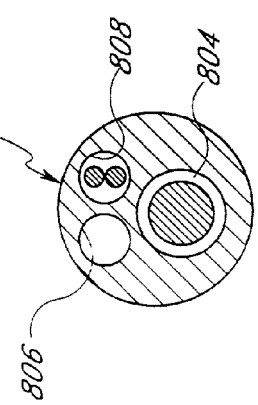
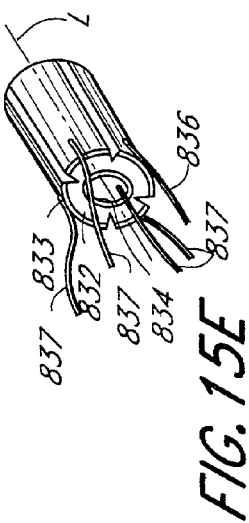
FIG. 15A
FIG. 15B
FIG. 15C
FIG. 15D
FIG. 15E

DEFLECTABLE TIP CATHETER WITH GUIDEWIRE TRACKING MECHANISM

RELATED APPLICATIONS

The present application claims priority under 35 U.S.C. §119(e) to U.S. Provisional Application No. 60/205009, filed May 16, 2000.

TECHNICAL FIELD

The present invention relates to a medical device for positioning a therapeutic device in a body structure. More particularly, the invention relates to a deflectable tip catheter that functions in combination with a guidewire to facilitate the advancement of a circumferential ablation device into a pulmonary vein ostium.

BACKGROUND OF THE INVENTION

Abnormal patterns of electrical conduction in the heart can produce abnormalities in the cardiac cycle known as arrythmias. A common form of arrhythmia, known as atrial fibrillation, is a pervasive problem in modem society. Atrial fibrillation is associated with an increased risk of myocardial ischemia, especially during strenuous activity, and has also been linked to congestive heart failure, stroke, and other thromboembolic events.

In the human heart, normal cardiac rhythm is maintained by a cluster of pacemaker cells, known as the sinoatrial ("SA") node, located within the wall of the right atrium. The SA node undergoes repetitive cycles of membrane depolarization and repolarization, thereby generating a continuous stream of electrical impulses, called "action potentials." These action potentials orchestrate the regular contraction and relaxation of the cardiac muscle cells throughout the heart. Action potentials spread rapidly from cell to cell through both the right and left atria via gap junctions between the cardiac muscle cells. Atrial arrhythmias result when electrical impulses originating from sites other than the SA node are conducted through the atrial cardiac tissue.

In some cases, atrial fibrillation results from perpetually wandering reentrant wavelets, which exhibit no consistent localized region(s) of aberrant conduction. In other cases, atrial fibrillation may be focal in nature, resulting from rapid and repetitive changes in membrane potential originating from isolated centers, or foci, within the atrial cardiac muscle tissue. These foci exhibit consistent centrifugal patterns of electrical activation, and may act as either a trigger of atrial fibrillatory paroxysmal or may even sustain the fibrillation. Recent studies have suggested that focal arrhythmias often originate from a tissue region along the pulmonary veins of the left atrium, and even more particularly in the superior pulmonary veins.

Several surgical approaches have been developed for the treatment of atrial fibrillation. For example, Cox, J L et al. disclose the "maze" procedure, in "The Surgical Treatment Of Atrial Fibrillation. I. Summary", *Thoracic and Cardiovascular Surgery* 101(3):402–405 (1991) and "The Surgical Treatment Of Atrial Fibrillation. IV. Surgical Technique", *Thoracic and Cardiovascular Surgery* 101(4):584–592 (1991). In general, the maze procedure is designed to relieve atrial arrhythmia by restoring effective SA node control through a prescribed pattern of incisions about the cardiac tissue wall. Although early clinical studies on the maze procedure included surgical incisions in both the right and left atrial chambers, more recent reports suggest that the maze procedure may be effective when performed only in the left atrium (see for example Sueda et al., "Simple Left Atrial Procedure For Chronic Atrial Fibrillation Associated With Mitral Valve Disease" (1996)).

The left atrial maze procedure involves forming vertical incisions from the two superior pulmonary veins and terminating in the region of the mitral valve annulus, traversing the inferior pulmonary veins en route. An additional horizontal incision connects the superior ends of the two vertical incisions. Thus, the atrial wall region bordered by the pulmonary vein ostia is isolated from the other atrial tissue. In this process, the mechanical sectioning of atrial tissue eliminates the atrial arrhythmia by blocking conduction of the aberrant action potentials.

The moderate success observed with the maze procedure and other surgical segmentation procedures have validated the principle that mechanically isolating cardiac tissue may successfully prevent atrial arrhythmias, particularly atrial fibrillation, resulting from either perpetually wandering reentrant wavelets or focal regions of aberrant conduction. Unfortunately, the highly invasive nature of such procedures may be prohibitive in many cases. Consequently, less invasive catheter-based approaches to treat atrial fibrillation have been developed.

These less invasive catheter-based therapies generally involve advancing a catheter into a cardiac chamber, such as in a percutaneous translumenal procedure, wherein an energy sink on the catheter's distal end portion is positioned at or adjacent to the aberrant conductive tissue. Upon application of energy, the targeted tissue is ablated and rendered non-conductive.

These catheter-based methods can be subdivided into two related categories, based on the etiology of the atrial arrhythmia. The first category includes various localized ablation methods used to treat focal arrhythmias by targeting the foci of aberrant electrical activity. Accordingly, devices and techniques have been disclosed which use end-electrode catheter designs for ablating focal arrhythmias centered in the pulmonary veins, using a point source of energy to ablate the locus of abnormal electrical activity. Such procedures typically employ incremental application of electrical energy to the tissue to form focal lesions. The second category includes methods designed for the treatment atrial fibrillations caused by perpetually wandering reentrant wavelets. Such arrhythmias are generally not amenable to localized ablation techniques because the excitation waves may circumnavigate a focal lesion. Thus, the second category of catheter-based approaches have generally attempted to mimic the earlier surgical segmentation techniques, such as the maze procedure, wherein continuous linear lesions are required to completely segment the atrial tissue so as to block conduction of the reentrant wave fronts.

An example of an ablation method targeting focal arrhythmias originating from a pulmonary vein is disclosed by Haissaguerre et al. in "Right And Left Atrial Radiofrequency Catheter Therapy Of Paroxysmal Atrial Fibrillation" in *J. Cardiovasc. Electrophys.* 7(12):1132–1144 (1996). Haissaguerre et al. describe radiofrequency catheter ablation of drug-refractory paroxysmal atrial fibrillation using linear atrial lesions complemented by focal ablation targeted at arrhythmogenic foci in a screened patient population. The site of the arrhythmogenic foci was generally located just inside the superior pulmonary vein, and was ablated using a standard 4 mm tip single ablation electrode.

Another ablation method directed at paroxysmal arrhythmias arising from a focal source is disclosed by Jais et al. "A Focal Source Of Atrial Fibrillation Treated By Discrete Radiofrequency Ablation" *Circulation* 95:572–576 (1997). At the site of arrhythmogenic tissue, in both right and left atria, several pulses of a discrete source of radiofrequency energy were applied in order to eliminate the fibrillatory process.

The treatment of reentrant wavelet arrhythmias through the use of catheter-based ablation techniques required the development of methods and devices for generating continuous linear lesions, like those employed in the maze procedure. Initially, conventional ablation tip electrodes were adapted for use in "drag burn" procedures to form linear lesions. During the "drag" procedure, as energy was being applied, the catheter tip was drawn across the tissue along a predetermined pathway within the heart. Alternatively, sequentially positioning the distal tip electrode, applying a pulse of energy, and then re-positioning the electrode along a predetermined linear pathway also made lines of ablation.

Subsequently, conventional catheters were modified to include multiple electrode arrangements. Such catheters typically contained a plurality of ring electrodes circling the catheter at various distances extending proximally from the distal tip of the catheter. More detailed examples of such catheter-based tissue ablation assemblies have been disclosed in U.S. Pat. No. 5,676,662 to Fleischhacker et al.; U.S. Pat. No. 5,688,267 to Panescu et al.; and U.S. Pat. No. 5,693,078 to Desai et al.

Further more detailed examples of transcatheter-based tissue ablation assemblies and methods are described in the following references: U.S. Pat. No. 5,575,810 to Swanson et al.; PCT Published Application WO 96/10961 to Fleischman et al.; U.S. Pat. No. 5,702,438 to Avitall; U.S. Pat. No. 5,687,723 to Avitall; U.S. Pat. No. 5,487,385 to Avitall; and PCT Published Application WO 97/37607 to Schaer.

While the disclosures above describe feasible catheter designs for imparting linear ablation tracks, as a practical matter, most of these catheter assemblies have been difficult to position and maintain placement and contact pressure long enough and in a sufficiently precise manner in the beating heart to successfully form segmented linear lesions along a chamber wall. Indeed, many of the aforementioned methods have generally failed to produce closed transmural lesions, thus leaving the opportunity for the reentrant circuits to reappear in the gaps remaining between point or drag ablations.

Due to the shortcomings associated with linear ablation techniques, a new method of treating atrial fibrillation was developed whereby a circumferential lesion is formed along a pulmonary vein ostium. The formation of a circumfential lesion creates a circumferential conduction block that electrically isolates a substantial portion of a posterior atrial wall from an arrhythmogenic focus located in a pulmonary vein. In a variation of this method, a circumferential lesion can be formed in combination with linear lesions to treat atrial fibrillation caused by wandering reentrant wavelets. These methods are disclosed in detail in U.S. Pat. No. 6,024,740 to Lesh.

U.S. Pat. No. 6,024,740 to Lesh et al. discloses a circumferential ablation device assembly used to form a circumferential lesion. The circumferential ablation device assembly includes an ablation element and an expandable member. The device is anchored in the pulmonary vein ostium using the expandable member and the ablation element is energized to form a circumferential lesion.

Although the aforementioned methods and devices have shown great success in treating atrial fibrillation through the formation of a circumferential lesion, optimizing the effectiveness of such methods and devices depends to some extent on the precise positioning of the ablation element at a location where the pulmonary vein extends from the atrium. At this time, minimal means have been disclosed for advancing ablation catheters to anatomic sites of interest such as the pulmonary veins.

Guidewire positioning techniques are known in the art and have been used extensively for catheter placement within difficult areas of a patient's vasculature. Guidewire positioning techniques generally involve advancing a guidewire through a patient's vasculature to the desired anatomical site and then advancing a catheter over the guidewire. However, the use of a guidewire alone does not provide an adequate means for placement of a catheter in a pulmonary vein because placement of the guidewire itself within a pulmonary vein poses a significant challenge.

Deflectable tip catheters are also known in the art and are often used for facilitating catheter placement. Deflectable tip catheters generally incorporate one or more internal pull wires affixed to the distal tip and to a proximal handle with a steering control mechanism. The steering control mechanism is used to deflect the tip of the catheter, usually in a single direction, as the catheter is advanced through a patient's vasculature. Detailed examples of steerable catheters and methods are described in the following references: U.S. Pat. No. 5,702,433 to Taylor, U.S. Pat. No. 5,755,327 to Randolph, U.S. Pat. No. 5,865,800 to Mirarchi et al., U.S. Pat. No. 5,882,333 to Schaer, U.S. Pat. No. 6,022,955 to Willems, U.S. Pat. No. 6,024,739 to Ponzi, U.S. Pat. No. 6,083,222 to Klein to Taylor, Although deflectable tip catheters have been successful in addressing certain internal cardiac areas, existing deflectable tip catheter designs are not well-suited for advancing an ablation catheter into a pulmonary vein. In practice, it has been found that existing deflectable tip catheter designs are not capable of navigating the sharp angle from the fossa ovalis to the pulmonary vein without great difficulty. Furthermore, once the deflectable tip catheter reaches the pulmonary vein ostium, the ablation element is often unable to sustain sufficient contact with the surrounding tissue to create an adequate circumferential lesion.

Therefore, a need exists for an improved ablation catheter that can be advanced through a patient's vasculature to a pulmonary vein ostium in a quick and easy manner. It is also desirable that such an ablation catheter be capable of engaging the surrounding tissue to create a circumferential lesion for isolating a pulmonary vein from the posterior atrial wall of the heart. A device that achieves these objectives would represent a significant advancement in the treatment of atrial fibrillation.

SUMMARY OF THE INVENTION

The present invention relates to an improved deflectable tip catheter design that is used in combination with a guidewire to facilitate the advancement of an intravascular device through a patient's vasculature. The present invention is particularly well-suited for use in advancing an ablation element into a pulmonary vein or pulmonary vein branch for performing circumferential ultrasound vein ablation (CUVA) to treat atrial fibrillation.

The deflectable tip catheter of the present invention provides the physician with the ability to aim the distal end of the guidewire in a desired direction as the guidewire is advanced from the distal end of the catheter. By using the deflectable tip portion to help direct the advancement of the guidewire, the physician's ability to maneuver the guidewire (and therefore the catheter) around sharp angles is dramatically improved. The deflectable tip catheter also can be used in other conventional modes as well. Such as, for example, the deflectable tip portion can be deflected to help steer the catheter through the patient's vasculature or to reduce resistance as the catheter is advanced over bends in the guidewire. Preferably, the deflectable tip catheter is designed for use with a variety of commercially available cardiology guidewires.

The deflectable tip catheter of the present invention generally comprises a handle portion, an elongated catheter body, a deflectable tip portion, and a guidewire tracking mechanism. The handle portion is provided at the proximal end of the elongated catheter body and provides a means for advancing the ablation device through the patient's vasculature. A pull wire is attached to the handle portion and also to the deflectable tip portion. By applying tension to the pull wire, the deflectable tip portion can be deflected relative to the elongated catheter body. By turning the handle portion, the orientation of the deflected tip may be rotated.

An elongated catheter body extends from the handle portion to the deflectable tip portion. The elongated catheter body is formed with an inner catheter, a stainless steel braid, and an outer extrusion. The inner catheter is preferably formed with a plurality of lumens including a guidewire lumen, a pull wire lumen, an inflation lumen, a co-axial cable lumen, and a thermocouple lead lumen. The elongated catheter body is relatively stiff as compared with the deflectable tip portion. The elongated catheter body is also constructed to provide high fidelity torque transmission to the deflectable tip portion when torque is applied to the handle portion.

An ablation element is disposed on the deflectable tip portion for ablating at least a substantial portion of the circumferential region of tissue. In a preferred embodiment, the ablation element comprises one or more ultrasonic transducers coupled to an energy source. In another embodiment, the ablation element comprises a piezoelectric transducer.

An anchoring member is also provided for anchoring the catheter during ablation procedures. The anchoring device provides a means for holding the ablation element steady relative to the beating heart during the ablation procedure. In a preferred embodiment, the anchoring member comprises an expandable balloon adapted to engage a circumferential region of tissue, such as the pulmonary vein ostium.

The present invention also relates to a method of ablating a substantial portion of a circumferenital region of tissue at a body location where a pulmonary vein extends from an atrium.

Other features and advantages of the invention will become apparent from the following detailed description, taken in conjunction with the accompanying drawings, which illustrate, by way of example, the features of the invention.

BRIEF DESCRIPTION OF THE DRAWINGS

FIGS. 8A–B show perspective views of another circumferential ablation catheter during use in a left atrium according to the method of FIG. 3, wherein FIG. 8A shows a radially compliant expandable member with a working length adjusted to a radially expanded position while in the left atrium, and FIG. 8B shows the expandable member after advancing it into and engaging a pulmonary vein ostium while in the radially expanded position.

FIGS. 11A–B show perspective views of one circumferential ablation member for use in a circumferential ablation device assembly, showing a circumferential ablation electrode circumscribing the working length of an expandable member with a secondary shape along the longitudinal axis of the working length which is a modified step shape, the expandable member being shown in a radially collapsed position and also in a radially expanded position, respectively.

FIGS. 11C–D show perspective views of two circumferential ablation electrodes which form equatorial or otherwise circumferentially placed bands that circumscribe the working length of an expandable member and that have serpentine and sawtooth secondary shapes, respectively, relative to the longitudinal axis of the expandable member when adjusted to a radially expanded position.

FIGS. 12A–B show perspective views of another circumferential ablation element which includes a plurality of individual ablation electrodes that are spaced circumferentially to form an equatorial band which circumscribes the working length of an expandable member either in an equatorial location or an otherwise circumferential location that is bounded both proximally and distally by the working length, and which are adapted to form a continuous circumferential lesion while the working length is adjusted to a radially expanded position.

FIG. 13 shows a cross-sectional view of another circumferential ablation member for use in a circumferential ablation device assembly, wherein the circumferential ablation element circumscribes an outer surface of an expandable member substantially along its working length and is insulated at both the proximal and the distal ends of the working length to thereby form an uninsulated equatorial band in a middle region of the working length or otherwise circumferential region of the working length which is bounded both proximally and distally by end portions of the working length, which member is adapted to ablate a circumferential path of tissue in a pulmonary wall adjacent to the equatorial band.

FIG. 15A shows a longitudinal cross-sectional view of another circumferential ablation catheter with an ablation element having a single cylindrical ultrasound transducer which is positioned along an inner member within an expandable balloon which is further shown in a radially expanded condition.

FIG. 15B shows a transverse cross-sectional view of the circumferential ablation catheter shown in FIG. 15A taken along line 15B—15B shown in FIG. 15A.

FIG. 15C shows a transverse cross-sectional view of the circumferential ablation catheter shown in FIG. 15A taken along line 15C—15C shown in FIG. 15A.

FIG. 15D shows a perspective view of the ultrasonic transducer of FIG. 15A in isolation.

FIG. 15E shows a modified version of the ultrasonic transducer of FIG. 15D with individually driven sectors.

DETAILED DESCRIPTION OF THE PREFERRED EMBODIMENT

Figure 1:
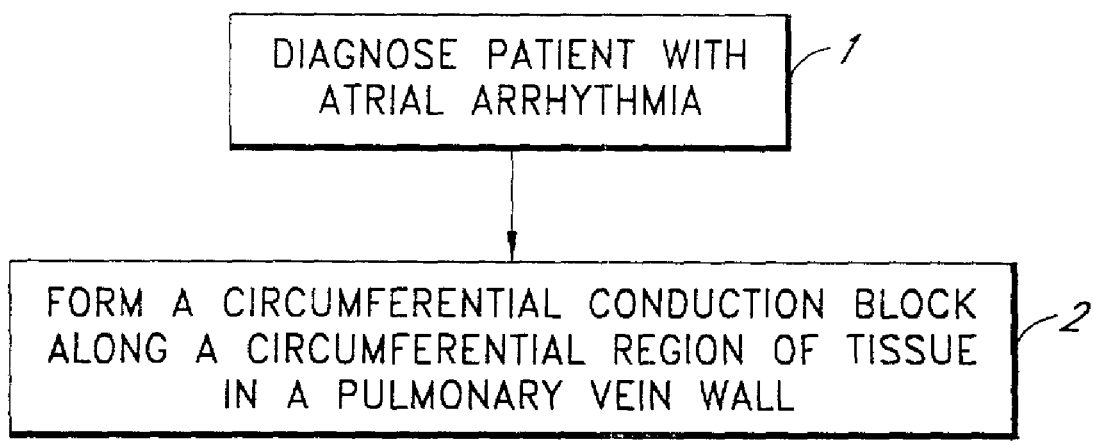
FIG. 1 diagrammatically shows sequential, general steps of a method for treating atrial arrhythmia through pulmonary vein isolation.

The present invention relates to an improved deflectable tip catheter that works in combination with a guidewire to facilitate the advancement of a catheter through a patient's vasculature. This invention has a wide variety of applications in the area of catheter-based therapies, however, for illustrative purposes, the invention is described with respect to the treatment of atrial fibrillation whereby a circumferential ablation catheter is advanced into a pulmonary vein ostium. Particular embodiments for pulmonary vein isolation are shown and described by reference to FIGS. 1–18B, with the related method of treatment broadly illustrated in diagrammatical form in the flow diagram of FIG. 1. The deflectable tip catheter assembly of the present invention and its method of operation are shown and described by reference to FIGS. 19–28.

The following terms will have the following meanings throughout this specification.

The terms "body space," including derivatives thereof, is herein intended to mean any cavity or lumen within the body which is defined at least in part by a tissue wall. For example, the cardiac chambers, the uterus, the regions of the gastrointestinal tract, and the arterial or venous vessels are all considered illustrative examples of body spaces within the intended meaning.

The term "body lumen," including derivatives thereof, is herein intended to mean any body space which is circumscribed along a length by a tubular tissue wall and which terminates at each of two ends in at least one opening that communicates externally of the body space. For example, the large and small intestines, the vas deferens, the trachea, and the fallopian tubes are all illustrative examples of lumens within the intended meaning. Blood vessels are also herein considered lumens, including regions of the vascular tree between their branch points. More particularly, the pulmonary veins are lumens within the intended meaning, including the region of the pulmonary veins between the branched portions of their ostia along a left ventricle wall, although the wall tissue defining the ostia typically presents uniquely tapered lumenal shapes.

The terms "circumference" or "circumferential", including derivatives thereof, as used herein include a continuous path or line which forms an outer border or perimeter that surrounds and thereby defines an enclosed region of space. Such a continuous path starts at one location along the outer border or perimeter, and translates along the outer border or perimeter until it is completed at the original starting location to enclose the defined region of space. The related term "circumscribe," including derivatives thereof, as used herein includes a surface to enclose, surround, or encompass a defined region of space. Therefore, a continuous line which is traced around a region of space and which starts and ends at substantially the same location "circumscribes" the region of space and has a "circumference" which includes the distance the line travels as it translates along the path circumscribing the space.

Still further, a circumferential path or element may include one or more of several shapes, and may be for example circular, oblong, ovular, elliptical, or otherwise planar enclosures. A circumferential path may also be three dimensional, such as for example two opposite-facing semi-circular paths in two different parallel or off-axis planes that are connected at their ends by line segments bridging between the planes.

A "circumferential conduction block" according to the present invention is formed along a region of tissue that follows a circumferential path along the pulmonary vein wall, circumscribing the pulmonary vein lumen and transecting the pulmonary vein relative to electrical conduction along its longitudinal axis. The transecting circumferential conduction block therefore isolates electrical conduction between opposite longitudinal portions of the pulmonary wall relative to the conduction block and along the longitudinal axis.

Figure 2A:
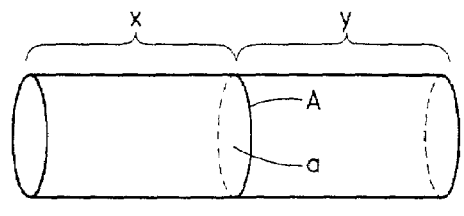
FIGS. 2A–E show schematic, perspective views of various circumferential conduction blocks formed at a location where a pulmonary vein extends from an atrium with a circumferential ablation device assembly.
Figure 2B:
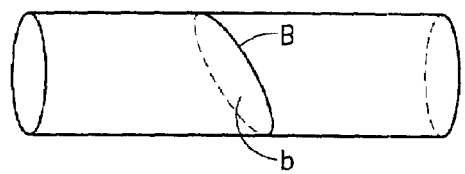
Figure 2C:
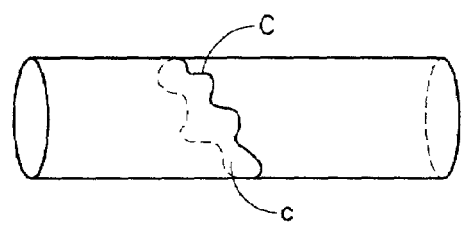
Figure 2D:
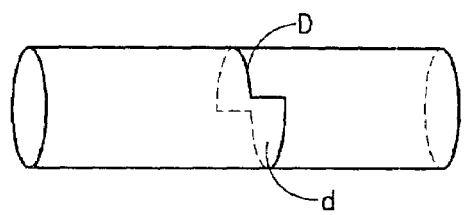
Figure 2E:
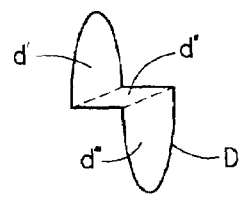

For purpose of further illustration, FIGS. 2A–D therefore show various circumferential paths A, B, C, and D, respectively, each translating along a portion of a pulmonary vein wall and circumscribing a defined region of space, shown at a, b, c, and d also respectively, each circumscribed region of space being a portion of a pulmonary vein lumen. For still further illustration of the three-dimensional circumferential case shown in FIG. 2D. FIG. 2E shows an exploded perspective view of circumferential path D as it circumscribes multiplanar portions of the pulmonary vein lumen shown at d', d", and d''', which together make up region d as shown in FIG. 2D.

The term "transect", including derivatives thereof, is also herein intended to mean to divide or separate a region of space into isolated regions. Thus, each of the regions circumscribed by the circumferential paths shown in FIGS. 2A–D transects the respective pulmonary vein, including its lumen and its wall, to the extent that the respective pulmonary vein is divided into a first longitudinal region located on one side of the transecting region, shown, for example, at region "X" in FIG. 2A, and a second longitudinal region on the other side of the transecting plane, shown, for example, at region "Y" also in FIG. 2A.

Therefore, a "circumferential conduction block" according to the present invention is formed along a region of tissue which follows a circumferential path along the pulmonary vein wall, circumscribing the pulmonary vein lumen and transecting the pulmonary vein relative to electrical conduction along its longitudinal axis. The transecting circumferential conduction block therefore isolates electrical conduction between opposite longitudinal portions of the pulmonary wall relative to the conduction block and along the longitudinal axis.

The terms "ablate" or "ablation," including derivatives thereof, are hereafter intended to include the substantial altering of the mechanical, electrical, chemical, or other structural nature of tissue. In the context of ablation applications shown and described with reference to the variations of the illustrative device below, "ablation" is intended to include sufficient altering of tissue properties to substantially block conduction of electrical signals from or through the ablated cardiac tissue.

The term "element" within the context of "ablation element" is herein intended to include a discrete element, such as an electrode, or a plurality of discrete elements, such as a plurality of spaced electrodes, which are positioned so as to collectively ablate a region of tissue.

Therefore, an "ablation element" according to the defined terms can include a variety of specific structures adapted to ablate a defined region of tissue. For example, one suitable ablation element for use in the present invention may be formed, according to the teachings of the embodiments below, from an "energy emitting" type of structure which is adapted to emit energy sufficient to ablate tissue when coupled to and energized by an energy source. Suitable "energy emitting" ablation elements for use in the present invention may therefore include, for example: an electrode element adapted to couple to a direct current ("DC") or alternating current ("AC") current source, such as a Radio Frequency ("RF") current source; an antenna element which is energized by a microwave energy source; a heating element, such as a metallic element or other thermal conductor which is energized to emit heat such as by convection or conductive heat transfer, by resistive heating due to current flow, or by optical heating with light; a light emitting element, such as a laser; or an ultrasonic element such as an ultrasound crystal element which is adapted to emit ultrasonic sound waves sufficient to ablate tissue when coupled to a suitable excitation source.

In addition, other elements for altering the nature of tissue may be suitable as "ablation elements" under the present invention when adapted according to the detailed description of the invention below. For example, a cryogenic ablation (cryoblation) element adapted to sufficiently cool tissue to substantially alter the structure thereof may be suitable if adapted according to the teachings of the current invention. Furthermore, a fluid delivery element, such as a discrete port or a plurality of ports which are fluidly coupled to a fluid delivery source, may be adapted to infuse an ablating fluid, such as a fluid containing alcohol, into the tissue adjacent to the port or ports to substantially alter the nature of that issue.

The term "anchor" is herein intended to broadly encompass any structure that functions to secure at least a portion of the disclosed ablation device assemblies to a pulmonary vein or pulmonary vein ostium, such that the circumferential and/or linear ablation elements are positioned sufficiently close to posterior wall of the left atrium to ablatively engage the targeted tissue. Examples of suitable anchors within the scope of the present disclosure include, conventional guidewires, guidewires with balloons, deflectable/steerable guidewires, shaped stylets, radially expandable members, inflatable members, etc.

The term "diagnose", including derivatives thereof, is intended to include patients suspected or predicted to have atrial arrhythmia, in addition to those having specific symptoms or mapped electrical conduction indicative of atrial arrhythmia.

Pulmonary Vein Isolation

As discussed above, the method of treating atrial fibrillation is broadly illustrated in diagrammatical form in the flow diagram of FIG. 1. A patient diagnosed with atrial arrhythmia according to diagnosing step (1) is treated with a circumferential conduction block according to treatment step (2).

In one aspect of the method of FIG. 1, a patient diagnosed with focal arrhythmia originating from an arrhythmogenic origin or focus in a pulmonary vein is treated according to this method when the circumferential conduction block is formed along a circumferential path of wall tissue that either includes the arrhythmogenic origin or is between the origin and the left atrium. In the former case, the arrhythmogenic tissue at the origin is destroyed by the conduction block as it is formed through that focus. In the latter case, the arrhythmogenic focus may still conduct abnormally, although such aberrant conduction is prevented from entering and affecting the atrial wall tissue due to the intervening circumferential conduction block.

In another aspect of the method, a patient diagnosed according to diagnosis step (1) with multiple wavelet arrhythmia originating from multiple regions along the atrial wall may be treated in part by forming the circumferential conduction block according to treatment step (2), although as an adjunct to forming long linear regions of conduction block between adjacent pulmonary vein ostia in a less-invasive "maze"-type catheter ablation procedure. More detail regarding this particular aspect of the inventive method is provided below with reference to a combination circumferential-long linear lesion ablation device that is described below with reference to FIGS. 9A–F.

In still a further aspect of the method shown in FIG. 1, the circumferential conduction block may be formed in one of several ways according to treatment step (2). In one example not shown, the circumferential conduction block may be formed by a surgical incision or other method to mechanically transect the pulmonary vein, followed by suturing the transected vein back together. As the circumferential injury is naturally repaired, such as through a physiologic scarring response common to the "maze" procedure, electrical conduction will generally not be restored across the injury site. In another example not shown, a circumferential conduction block of one or more pulmonary veins may be performed in an epicardial ablation procedure, wherein an ablation element is either placed around the target pulmonary vein or is translated circumferentially around it while being energized to ablate the adjacent tissue in an "outside-in" approach. This alternative method may be performed during an open chest-type procedure, or may be done using other known epicardial access techniques.

Figure 3:
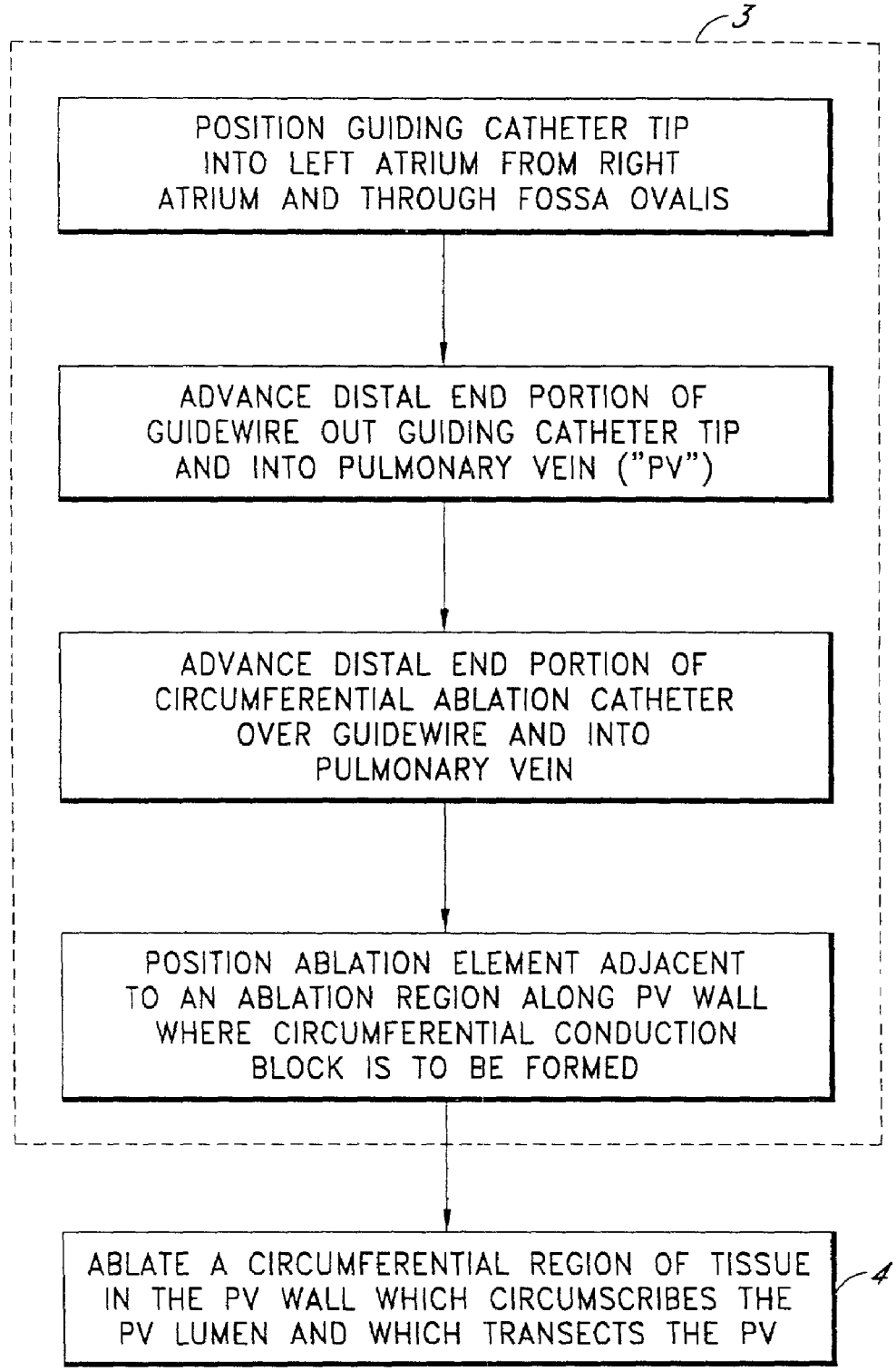
FIG. 3 shows a flow diagram of a method for using a circumferential ablation device assembly to form a circumferential conduction block at a location where a pulmonary vein extends from an atrium.

FIG. 3 diagrammatically shows the sequential steps of a method for using the circumferential ablation device assembly of the present invention in forming a circumferential conduction block at a location where a pulmonary vein extends from an atrium. The circumferential ablation method according to FIG. 3 includes: positioning a circumferential ablation element at an ablation region along the pulmonary vein according to a series of detailed steps shown collectively in FIG. 3 as positioning step (3); and thereafter ablating a continuous circumferential region of tissue in the PV wall at the ablation region according to ablation step (4).

Further to positioning step (3) according to the method of FIG. 3, a distal tip of a guiding catheter is first positioned within the left atrium according to a transeptal access method, which is further described in more detail as follows. The right venous system is first accessed using the "Seldinger" technique, wherein a peripheral vein (such as a femoral vein) is punctured with a needle, the puncture wound is dilated with a dilator to a size sufficient to accommodate an introducer sheath, and an introducer sheath with at least one hemostatic valve is seated within the dilated puncture wound while maintaining relative hemostasis. With the introducer sheath in place, the guiding catheter or sheath is introduced through the hemostatic valve of the introducer sheath and is advanced along the peripheral vein, into the region of the vena cavae, and into the right atrium.

Once in the right atrium, the distal tip of the guiding catheter is positioned against the fossa ovalis in the intraatrial septal wall. A "Brockenbrough" needle or trocar is then advanced distally through the guide catheter until it punctures the fossa ovalis. A separate dilator may also be advanced with the needle through the fossa ovalis to prepare an access port through the septum for seating the guiding catheter. The guiding catheter thereafter replaces the needle across the septum and is seated in the left atrium through the fossa ovalis, thereby providing access for object devices through its own inner lumen and into the left atrium.

It is however further contemplated that other left atrial access methods may be suitable substitutes for using the circumferential ablation device assembly of the present invention. In one alternative variation not shown, a "retrograde" approach may be used, wherein the guiding catheter is advanced into the left atrium from the arterial system. In this variation, the Seldinger technique is employed to gain vascular access into the arterial system, rather than the venous, for example, at a femoral artery. The guiding catheter is advanced retrogradedly through the aorta, around the aortic arch, into the ventricle, and then into the left atrium through the mitral valve.

Subsequent to gaining transeptal access to the left atrium as just described, positioning step (3) according to FIG. 3 next includes advancing a guidewire into a pulmonary vein. The guidewire may be advanced into the pulmonary vein by directing it with a second sub-selective delivery catheter (not shown) which is coaxial within the guiding catheter, such as, for example, by using one of the directional catheters disclosed in U.S. Pat. No. 5,575,766 to Swartz. Or, the guidewire may have sufficient stiffness and maneuverability in the left atrial cavity to unitarily subselect the desired pulmonary vein distally of the guiding catheter seated at the fossa ovalis. However, preferably, the guidewire is advanced into the pulmonary vein using the deflectable tip catheter described below in detail with reference to FIGS. 19–28.

Subsequent to gaining pulmonary vein access, positioning step (3) of FIG. 3 next includes tracking the distal end portion of a circumferential ablation device assembly over the guidewire and into the pulmonary vein, followed by positioning a circumferential ablation element at an ablation region of the pulmonary vein where the circumferential conduction block is to be desirably formed.

Circumferential Ablation Devices and Methods

Figure 4:
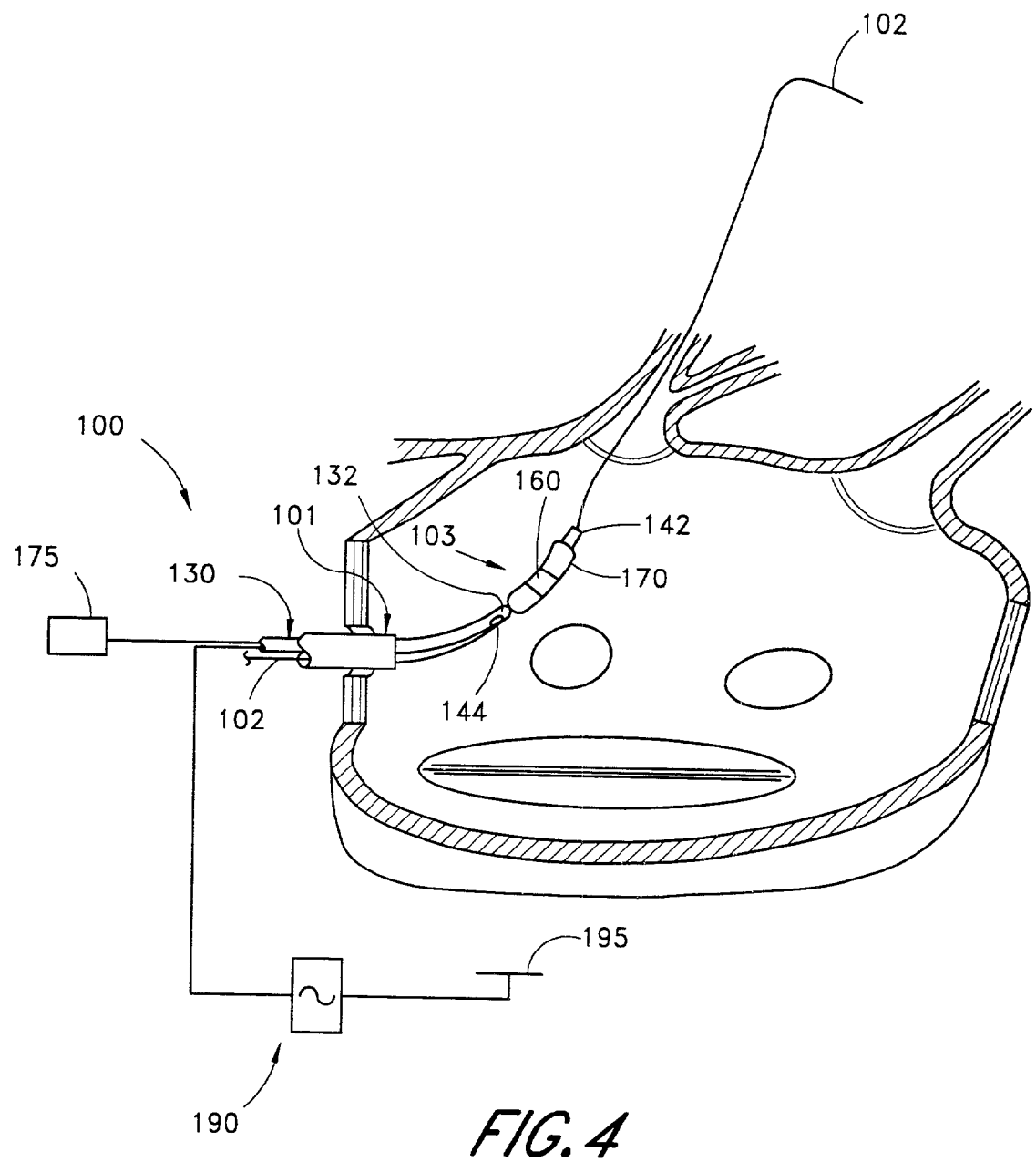
FIG. 4 shows a perspective view of a circumferential ablation device assembly during use in a left atrium subsequent to performing transeptal access and guidewire positioning steps according to the method of FIG. 3.

FIG. 4 further shows a circumferential ablation device assembly 100 during use in performing positioning step (3) and ablation step (4) just described with reference to FIG. 3. Included in the circumferential ablation device assembly 100 are guiding catheter 101, guidewire 102, and circumferential ablation catheter 103.

More specifically, FIG. 4 shows guiding catheter 101 subsequent to performing a transeptal access method according to FIG. 3, and also shows guidewire 102 subsequent to advancement and positioning within a pulmonary vein, also according to step (3) of FIG. 3. FIG. 4 shows circumferential ablation catheter 103 as it tracks coaxially over guidewire 102 with a distal guidewire tracking member, which is specifically shown only in part at first and second distal guidewire ports 142, 144 located on the distal end portion 132 of an elongate catheter body 130. A guidewire lumen (not shown) extends between the first and second distal guidewire ports 142, 144 and is adapted to slideably receive and track over the guidewire. In the particular variation of FIG. 4, the second distal guidewire port 142 is located on a distal end portion 132 of the elongate catheter body 130, although proximally of first distal guidewire port 142.

As would be apparent to one of ordinary skill, the distal guidewire tracking member shown in FIG. 4 and just described may be slideably coupled to the guidewire externally of the body in a "backloading" technique after the guidewire is first positioned in the pulmonary vein. Furthermore, there is no need in this guidewire tracking variation for a guidewire lumen in the proximal portions of the elongate catheter body 130, which allows for a reduction in the outer diameter of the catheter shaft in that region. Nevertheless, it is further contemplated that a design which places the second distal guidewire port on the proximal end portion of the elongate catheter body would also be acceptable, as is described below, for example, with reference to the perfusion embodiment of FIGS. 6A–B.

In addition, the inclusion of a guidewire lumen extending within the elongate catheter body between first and second ports, as provided in FIG. 4, should not limit the scope of acceptable guidewire tracking members according to the present invention. Other guidewire tracking members which form a bore adapted to slideably receive and track over a guidewire are also considered acceptable, such as, for example, the structure adapted to engage a guidewire as described in U.S. Pat. No. 5,505,702 to Arney, the entirety of which is hereby incorporated by reference herein.

While the assemblies and methods shown variously throughout the figures include a guidewire coupled to a guidewire tracking member on the circumferential ablation catheter, other detailed variations may also be suitable for positioning the circumferential ablation element at the ablation region in order to form a circumferential conduction block there. For example, an alternative circumferential ablation catheter not shown may include a "fixed-wire"-type of design wherein a guidewire is integrated into the ablation catheter as one unit. In another alternative assembly, the same type of sub-selective sheaths described above with reference to U.S. Pat. No. 5,575,766 to Swartz for advancing a guidewire into a pulmonary vein may also be used for advancing a circumferential ablation catheter device across the atrium and into a pulmonary vein.

Figure 5:
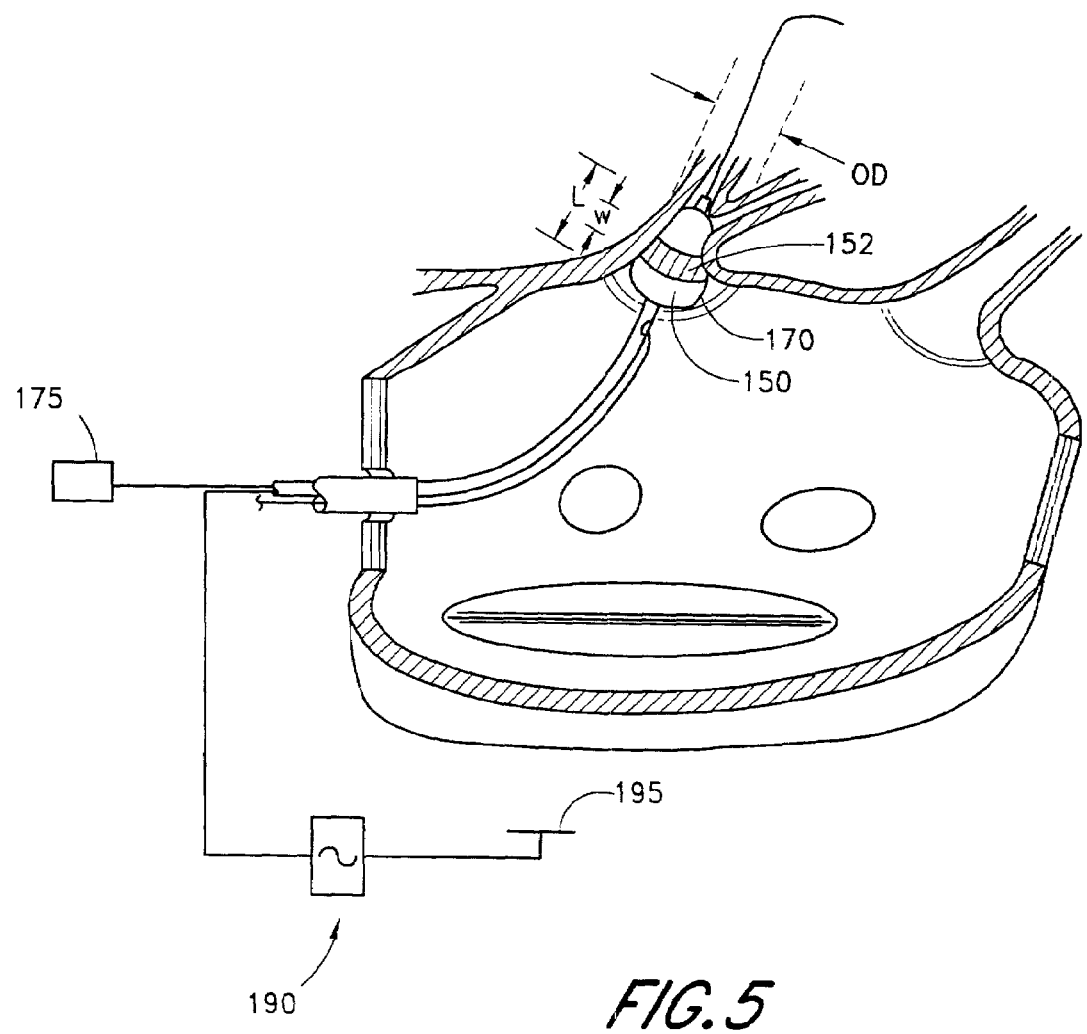
FIG. 5 shows a similar perspective view of the circumferential ablation device assembly shown in FIG. 4, and further shows a circumferential ablation catheter during use in ablating a circumferential region of tissue to form a circumferential conduction block in the pulmonary vein according to the method of FIG. 3.

FIG. 4 also shows circumferential ablation catheter 103 with a circumferential ablation element 160 formed on an expandable member 170. The expandable member 170 is shown in FIG. 4 in a radially collapsed position adapted for percutaneous translumenal delivery into the pulmonary vein according to positioning step (3) of FIG. 3. However, expandable member 170 is also adjustable to a radially expanded position when actuated by an expansion actuator 175, as shown in FIG. 5. Expansion actuator 175 may include, but is not limited to, a pressurizable fluid source. According to the expanded state shown in FIG. 5, expandable member 170 includes a working length L relative to the longitudinal axis of the elongate catheter body which has a larger expanded outer diameter OD than when in the radially collapsed position. Furthermore, the expanded outer diameter OD is sufficient to circumferentially engage the ablation region of the pulmonary vein. Therefore, the terms "working length" are herein intended to mean the length of an expandable member which, when in a radially expanded position, has an expanded outer diameter that is: (a) greater than the outer diameter of the expandable member when in a radially collapsed position; and (b) sufficient to engage a body space wall or adjacent ablation region surrounding the expandable member, at least on two opposing internal sides of the body space wall or adjacent ablation region, with sufficient surface area to anchor the expandable member.

Circumferential ablation member 150 also includes a circumferential band (hatched) on the outer surface of working length L which is coupled to an ablation actuator 190 at a proximal end portion of the elongate catheter body (shown schematically). After expandable member 170 is adjusted to the radially expanded position and at least a portion of working length L circumferentially engages the pulmonary vein wall in the ablation region, the circumferential band of the circumferential ablation member 150 is actuated by ablation actuator 190 to ablate the surrounding circumferential path of tissue in the pulmonary vein wall, thereby forming a circumferential lesion that circumscribes the pulmonary vein lumen and transects the electrical conductivity of the pulmonary vein to block conduction in a direction along its longitudinal axis.

Figure 6B:
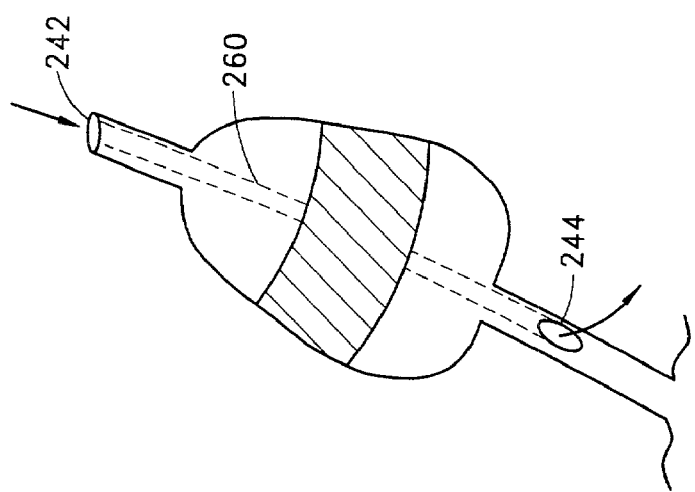
FIG. 6B is an enlarged partial view of the circumferential ablation catheter shown in FIG. 6A, with a perfusion lumen shown in phantom.
Figure 6A:
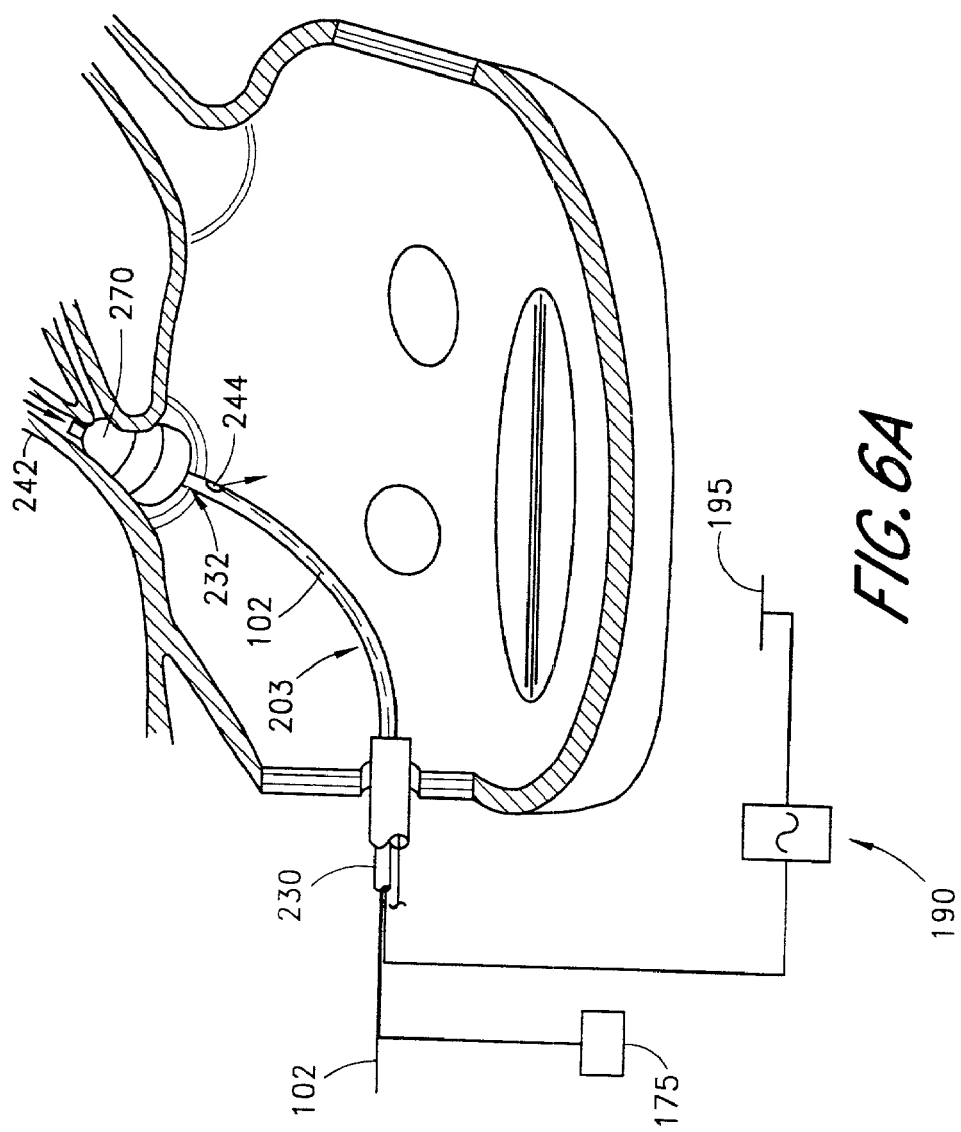
FIG. 6A shows a similar perspective view as shown in FIG. 5, although showing a circumferential ablation catheter which is adapted to allow for blood perfusion from the pulmonary vein and into the atrium while performing the circumferential ablation method shown diagrammatically in FIG. 3.

FIG. 6A shows another circumferential ablation catheter 203 during use also according to the method of FIG. 3, wherein a perfusion lumen 260 (shown in phantom in FIG. 6B) is formed within the distal end portion 132 of elongate catheter body 230. The perfusion lumen 260 in this example is formed between a distal perfusion port 242 (FIG. 6B), which in this example is the first distal guidewire port 242, and proximal perfusion port 244. Proximal perfusion port 244 is formed through the wall of the elongate catheter body 230 and communicates with the guidewire lumen (not shown) which also forms the perfusion lumen between the distal and proximal perfusion ports. In the particular design shown, after the guidewire has provided for the placement of the ablation element into the pulmonary vein, the guidewire is withdrawn proximally of the proximal perfusion port 244 so that the lumen (shown schematically in shadow) between the ports is clear for antegrade blood flow into the distal perfusion port 242, proximally along the perfusion lumen, out the proximal perfusion port 244 and into the atrium (perfusion flow shown schematically with arrows).

Further to the perfusion design shown in FIGS. 6A–B, guidewire 102 is positioned in a guidewire lumen which extends the entire length of the elongate catheter body 230 in an "over-the-wire"-type of design, which facilitates the proximal withdrawal of the guidewire to allow for perfusion while maintaining the ability to subsequently re-advance the guidewire distally through the first distal guidewire port 242 for catheter repositioning. In one alternative variation not shown, the guidewire is simply withdrawn and disengaged from the second distal guidewire port, in which case the circumferential ablation catheter must generally be withdrawn from the body in order to re-couple the distal guidewire tracking member with the guidewire.

In another alternative perfusion variation not shown which is a modification of the embodiment of FIG. 6A, a proximal perfusion port is provided as a separate and distinct port positioned between the second distal guidewire port and the expandable member, which allows for proximal withdrawal of the guidewire to clear the guidewire lumen and thereby form a perfusion lumen between the first distal guidewire port and the proximal perfusion port. The guidewire of this alternative variation, however, remains engaged within the guidewire lumen between the second distal guidewire port and the proximal perfusion port.

Passive perfusion during expansion of the expandable member is believed to minimize stasis and allow the target pulmonary vein to continue in its atrial filling function during the atrial arrhythmia treatment procedure. In addition, in cases where the ablation element is adapted to ablate tissue with heat conduction at the ablation region, as described by reference to more detailed embodiments below, the perfusion feature according to the variation of FIGS. 6A–B may also provide a cooling function in the surrounding region, including in the blood adjacent to the expandable member.

Moreover, in addition to the specific perfusion structure shown and described by reference to FIGS. 6A–B, it is to be further understood that other structural variants which allow for perfusion flow during expansion of the expandable element may provide suitable substitutes according to one of ordinary skill without departing from the scope of the present invention.

Figure 7:
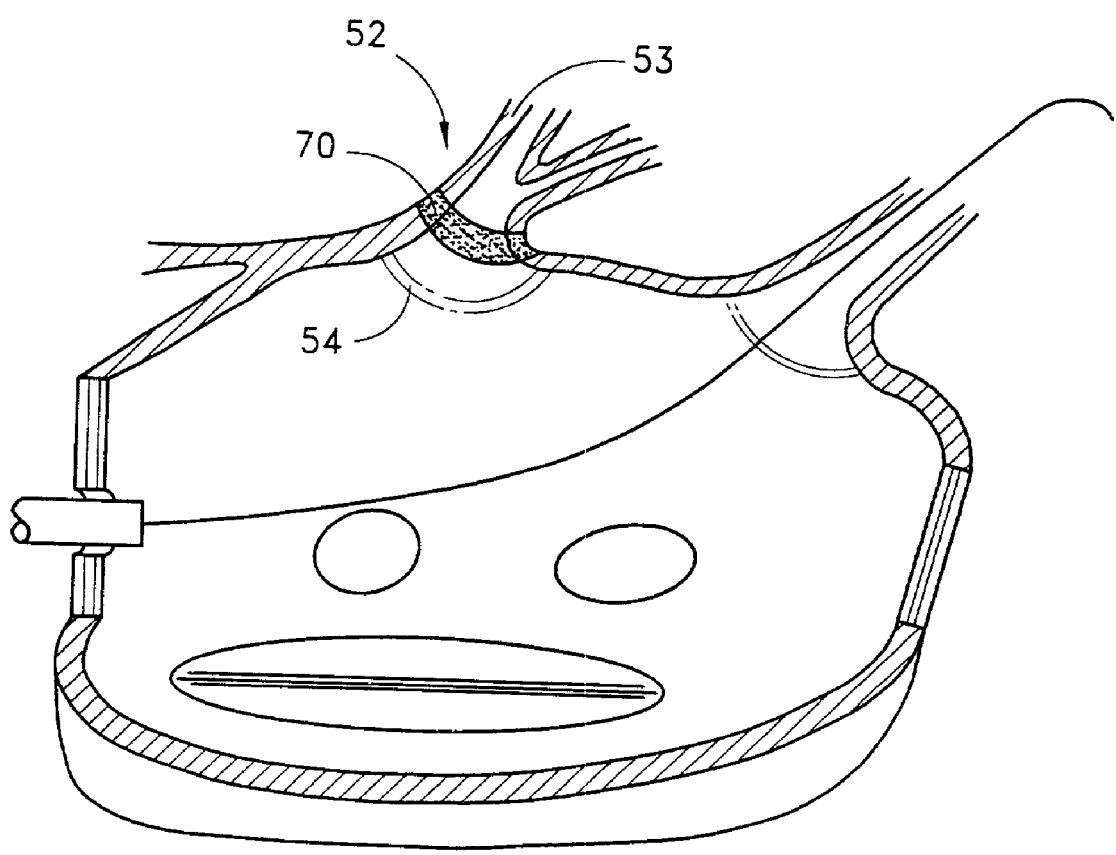
FIG. 7 shows a similar perspective view of the left atrium as that shown in FIGS. 3–5, although showing a cross-sectional view of a circumferential lesion after being formed by circumferential catheter ablation according to the method of FIG. 3.

FIG. 7 shows pulmonary vein 52 after removing the circumferential ablation device assembly subsequent to forming a circumferential lesion 70 around the ablation region of the pulmonary vein wall 53 according to the use of the circumferential ablation device assembly shown in stepwise fashion in FIGS. 3–6. Circumferential lesion 70 is shown located along the pulmonary vein adjacent to the pulmonary vein ostium 54, and is shown to also be "transmural," which is herein intended to mean extending completely through the wall, from one side to the other. Also, the circumferential lesion 70 is shown in FIG. 7 to form a "continuous" circumferential band, which is herein intended to mean without gaps around the pulmonary vein wall circumference, thereby circumscribing the pulmonary vein lumen.

It is believed, however, that circumferential catheter ablation with a circumferential ablation element according to the present invention may leave some tissue, either transmurally or along the circumference of the lesion, which is not actually ablated, but which is not substantial enough to allow for the passage of conductive signals. Therefore, the terms "transmural" and "continuous" as just defined are intended to have functional limitations, wherein some tissue in the ablation region may be unablated but there are no functional gaps which allow for symptomatically arrhythmogenic signals to conduct through the conduction block and into the atrium from the pulmonary vein.

Moreover, it is believed that the functionally transmural and continuous lesion qualities just described are characteristic of a completed circumferential conduction block in the pulmonary vein. Such a circumferential conduction block thereby transects the vein, isolating conduction between the portion of the vein on one longitudinal side of the lesion and the portion on the other side. Therefore, any foci of originating arrhythmogenic conduction which is opposite the conduction block from the atrium is prevented by the conduction block from conducting down into the atrium and atrial arrhythmic affects are therefore nullified.

Figure 8A:
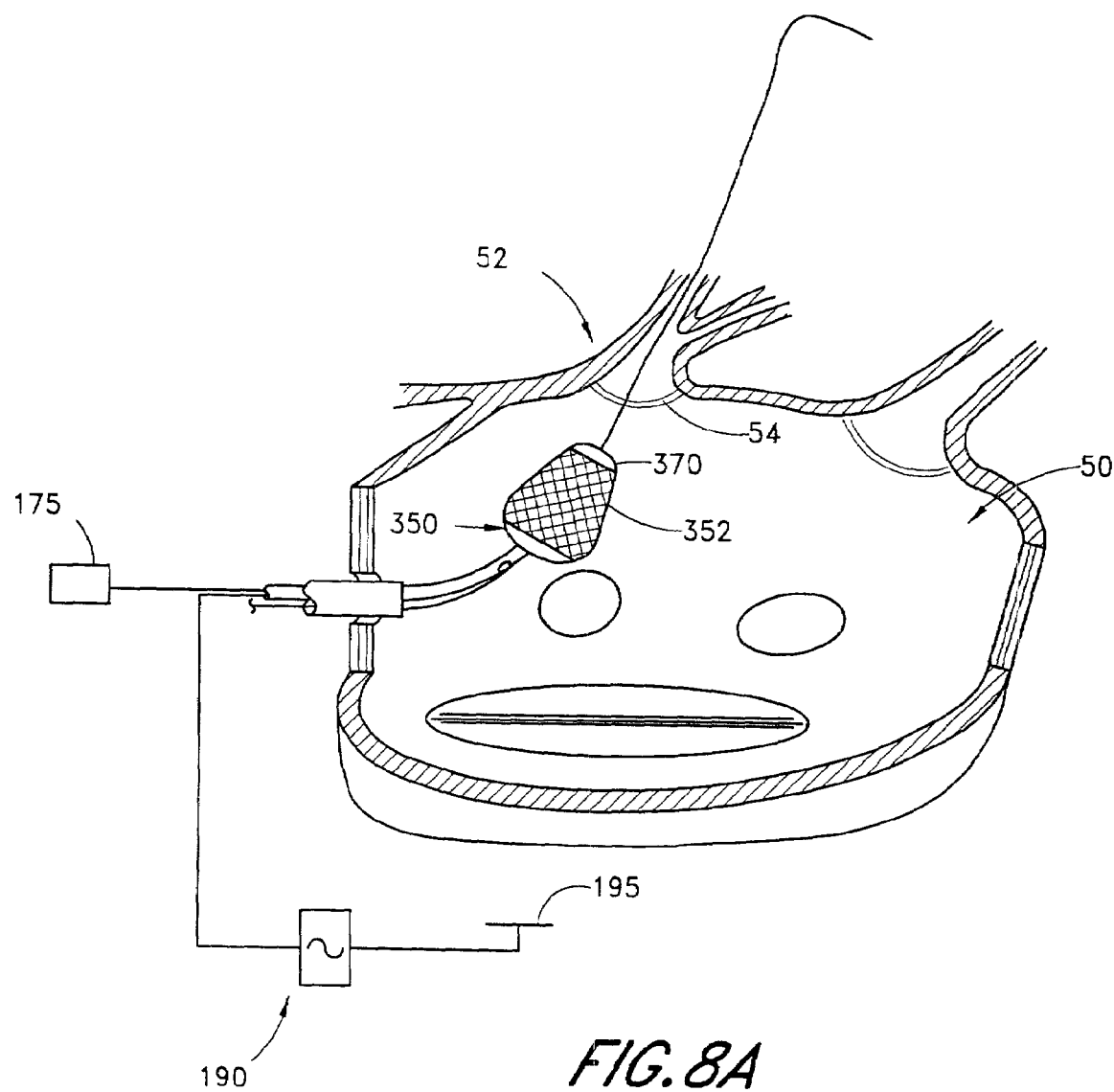
Figure 8B:
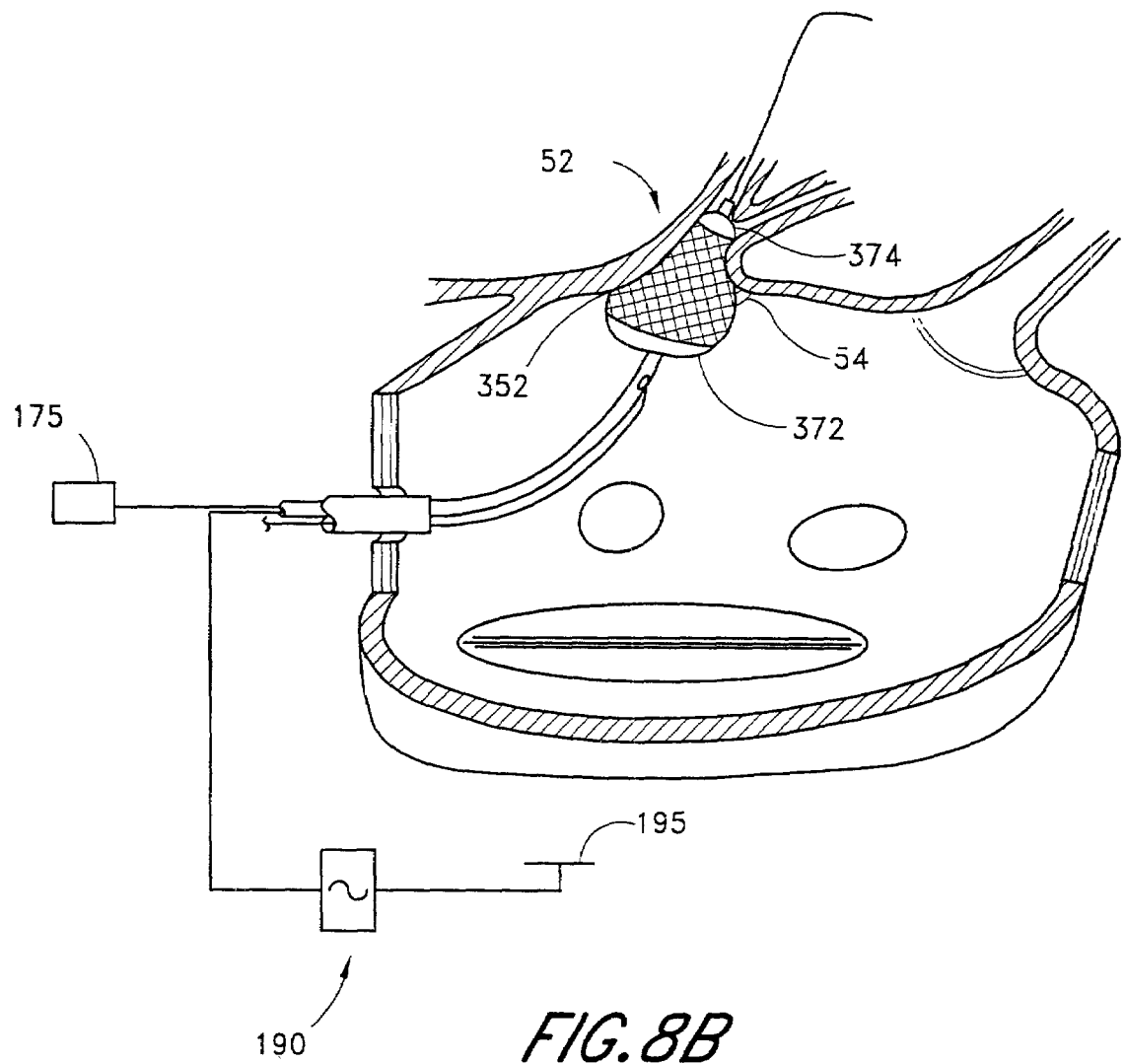
Figure 8C:
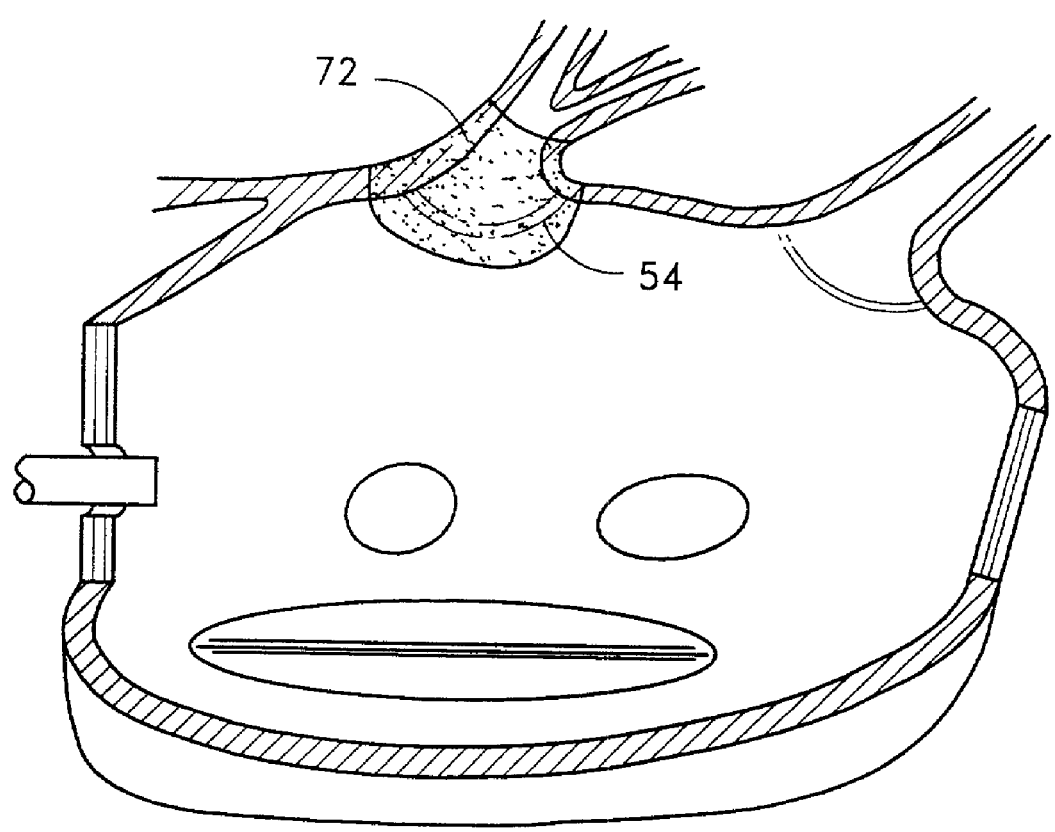
FIG. 8C shows the same perspective view of the left atrium shown in FIGS. 8A–B, although shown after forming a circumferential conduction block according to the circumferential ablation procedure of FIG. 3 and also after removing the circumferential ablation device assembly from the left atrium.

FIGS. 8A–B show a further variation of the circumferential ablation device, wherein a circumferential ablation member 350 includes a radially compliant expandable member 370 which is adapted to conform to a pulmonary vein ostium 54 at least in part by adjusting it to a radially expanded position while in the left atrium and then advancing it into the ostium. A circumferential ablation element 352 forms a band around expandable member 370, and is coupled to ablation actuator 190. FIG. 8A shows expandable member 370 after being adjusted to a radially expanded position while located in the left atrium 50. FIG. 8B further shows the expandable member after being advanced into the pulmonary vein 52 until at least a portion of the expanded working length L of circumferential ablation member, which includes a circumferential ablation element 352, engages the pulmonary vein ostium 54. The tapered distal portion 374 of the expandable member is shown conforming to the vein 52, whereas the proximal portion 372 is radially expanded so that the circumferential ablation element 352 ablatively contacts the ostium 54, and in some cases, also a portion of the posterior wall of the atrium. FIG. 8C shows a portion of a circumferential lesion 72 that forms a circumferential conduction block that encompasses the region of the pulmonary vein ostium 54 subsequent to actuating the circumferential ablation element to form the circumferential lesion.

In addition to conforming to the pulmonary vein ostium, the proximal portion 372 of expandable member is also shown in FIG. 8B to engage a circumferential path of tissue along the left posterior atrial wall which surrounds ostium 54. Moreover, circumferential band 352 of the circumferential ablation member is also thereby adapted to engage that atrial wall tissue. Therefore, the circumferential conduction block formed according to the method shown and just described in sequential steps by reference to FIGS. 8A–B, as shown in-part in FIG. 8C, includes ablating the circumferential path of atrial wall tissue and pulmonary vein wall which surrounds ostium 54. Accordingly, the entire pulmonary vein, including the ostium, is thereby electrically isolated from at least a substantial portion of the left atrial wall which includes the other of the pulmonary vein ostia, as would be apparent to one of ordinary skill according to the sequential method steps shown in FIGS. 8A–B and by further reference to the resulting circumferential lesion 72 shown in FIG. 8C.

Figure 8E:
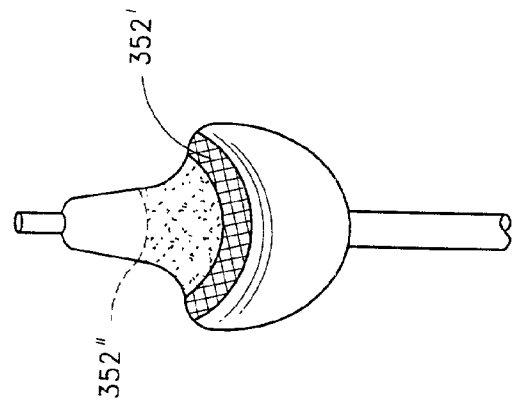
FIG. 8E shows one particular expandable member and circumferential ablation element that is adapted for use according to the mode of use shown in FIG. 8D.
Figure 8D:
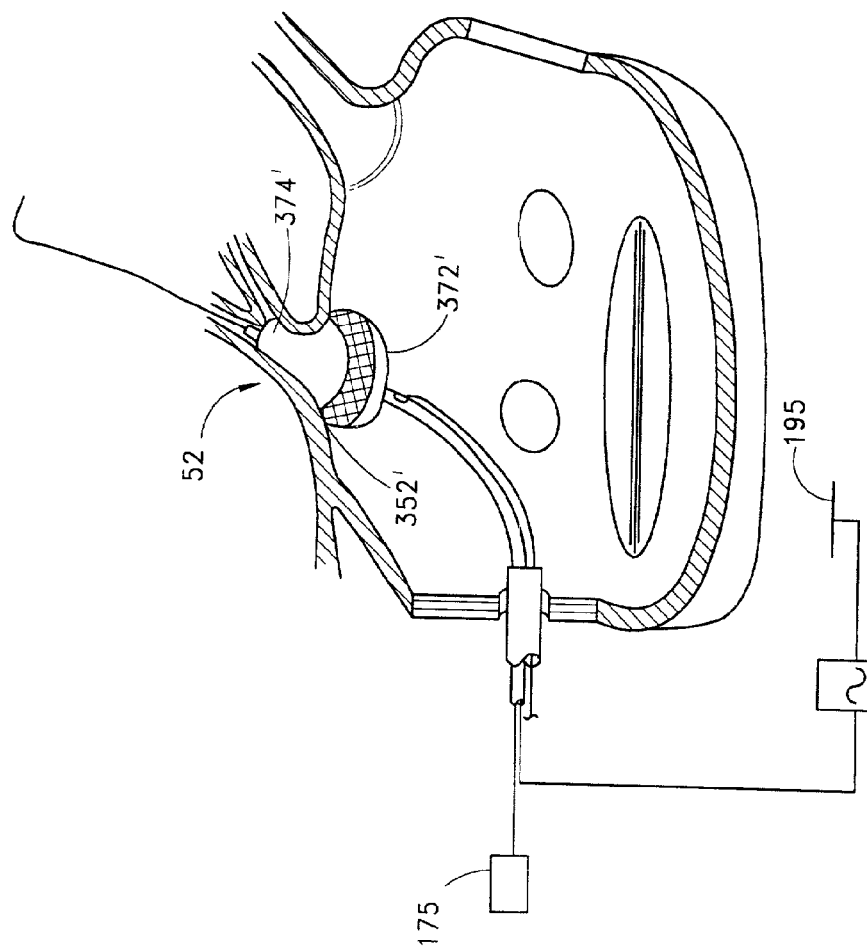
FIG. 8D shows another circumferential ablation catheter during use in a left atrium, and shows an expandable member in a radially expanded position which is engaged within a pulmonary vein ostium such that a circumferential band of a circumferential ablation element circumscribing the expandable member is also engaged to a circumferential path of tissue along the left posterior atrial wall which surrounds the pulmonary vein ostium.

FIGS. 8D–E show another highly beneficial circumferential ablation device embodiment and use thereof for electrically isolating pulmonary vein and ostium from a substantial portion of the left posterior atrial wall. However, unlike the embodiment previously shown and described by reference to FIGS. 8A–C, the FIG. 8D–E embodiment isolates the pulmonary vein without also ablating tissue along the lumen or lining of the pulmonary vein or ostium, as is apparent by reference to the resulting circumferential conduction block 72' shown in FIG. 8F.

In more detail, FIG. 8D shows a similar device assembly as that shown in FIGS. 8A–B, except that circumferential band 352' has a geometry (primarily width) and position around the proximal portion 372' of the expandable member such that it is adapted to engage only a circumferential path of tissue along the left posterior atrial wall which surrounds the pulmonary vein ostium. The tapered distal portion 374' is shown engaging the pulmonary vein 52. In one aspect of this embodiment, the compliant nature of the expandable member may be self-conforming to the region of the ostium such that the circumferential band is placed against this atrial wall tissue merely by way of conformability.

In another variation, a "pear-shaped" expandable member or balloon that includes a contoured taper may be suitable for use according to the FIG. 8D embodiment, as is shown by way of example in FIG. 8E. Such a pear shape may be preformed into the expandable member or balloon, or the member may be adapted to form this shape by way of controlled compliance as it expands, such as for example by the use of composite structures within the balloon construction. In any case, according to the "pear-shaped" variation, the circumferential band 352' of the ablation member is preferably placed along the surface of the contoured taper which is adapted to face the left posterior atrial wall during use according to the method illustrated by FIG. 8D. It is further contemplated that the ablation element may be further extended or alternatively positioned along other portions of the taper, such as is shown by example in shadow at extended band 352" in FIG. 8E. Accordingly, the variation shown in FIG. 8E to include extended band 352" may also adapt this particular device embodiment for use in forming circumferential conduction blocks also along tissue within the pulmonary vein and ostium, such as according to the method shown in FIGS. 8A–C.

Figure 8F:
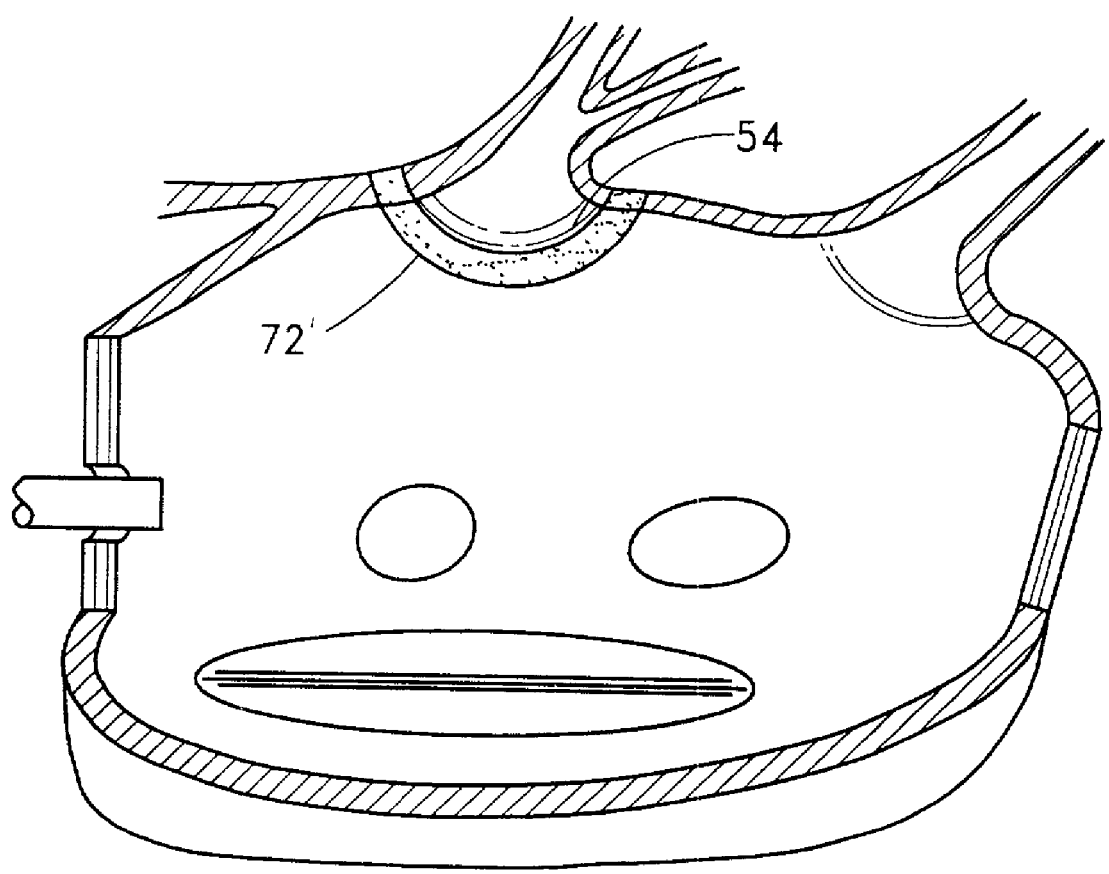
FIG. 8F shows a resulting circumferential conduction block or lesion which may be formed with the assemblies shown in FIGS. 8D–E and according to the method of use shown in FIG. 8D.

The method of forming a circumferential conduction block along a circumferential path of tissue along a left posterior atrial wall and which surrounds a pulmonary vein ostium without ablating the tissue of the vein or ostium should not be limited to the particular device embodiments just illustrated by reference to FIGS. 8D–F. Other device variations may be acceptable substitute for use according to this method. In one particular example which is believed to be suitable, a "looped" ablation member such as the embodiment illustrated below by reference to FIG. 15 may be adapted to form a "looped" ablation element within the left atrium and then be advanced against the left posterior atrial wall such that the loop engages the circumferential path of tissue along the atrial wall and which surrounds a vein ostium. Thereafter, the looped ablation element may be actuated to ablate the engaged tissue, such as for further illustration like a branding iron forming the predetermined pattern around the pulmonary vein ostium. In addition, other device or method variations may also be suitable substitutes according to one of ordinary skill.

FIGS. 9A–D collectively show a circumferential ablation device assembly as it is used to form a circumferential conduction block adjunctively to the formation of long linear lesions in a less-invasive "maze"-type procedure, as introduced above for the treatment of multiwavelet reentrant type fibrillation along the left atrial wall.

Figure 9A:
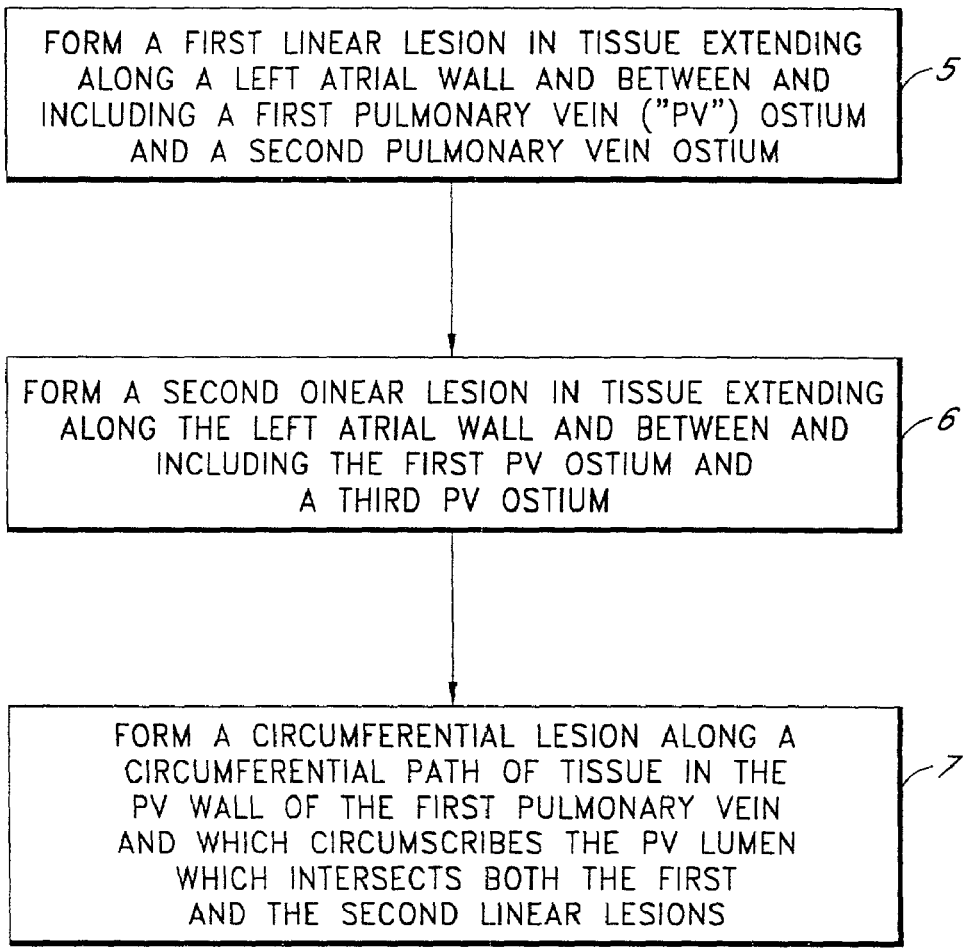
FIG. 9A diagrammatically shows a method for using a circumferential ablation device assembly to form a circumferential conduction block at a location where a pulmonary vein extends from an atrium in combination with a method for forming long linear lesions between pulmonary vein ostia in a less-invasive "maze"-type procedure.

More specifically, FIG. 9A diagrammatically shows a summary of steps for performing a "maze"-type procedure by forming circumferential conduction blocks that intersect with long linear conduction blocks formed between the pulmonary veins. As disclosed in co-pending patent application U.S. Ser. No. 08/853,861 entitled "Tissue Ablation Device and Method of Use", which is herein incorporated in its entirety by reference thereto, a box-like conduction block surrounding an arrhythmogenic atrial wall region bounded by the pulmonary veins may be created by forming long linear lesions 57, 58 and 59 between anchors in all pairs of adjacent pulmonary vein ostia, such as is shown in part in steps (5) and (6) of FIG. 9A. However, it is further believed that, in some particular applications, such linear lesions may be made sufficiently narrow with respect to the surface area of the pulmonary vein ostia that they may not intersect, thereby leaving gaps between them which may present proarrhythmic pathways for abnormal conduction into and from the box, such as is shown between linear lesions 57 and 58 in FIG. 9B. Therefore, by forming the circumferential conduction block according to step (7) of FIG. 9A, and as shown by use of circumferential ablation member 450 in FIG. 9C, the linear lesions 57 and 58 are thereby bridged and the gaps are closed.

Figure 9B:
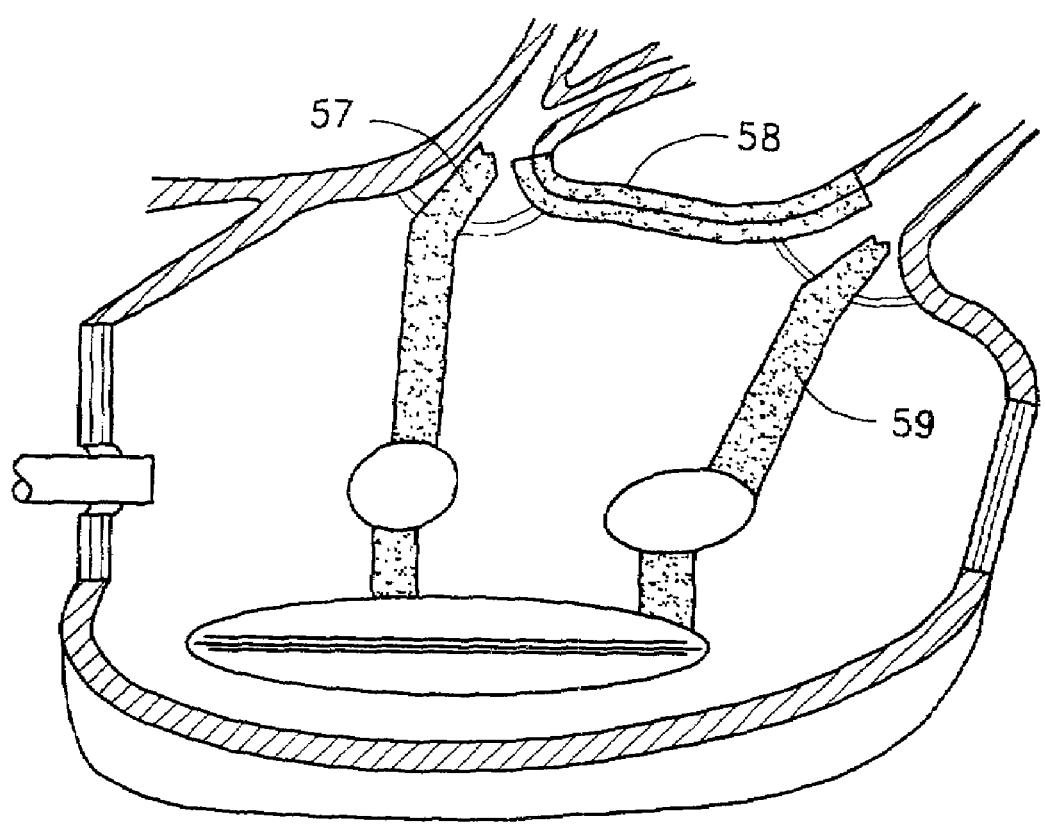
FIG. 9B shows a perspective view of a segmented left atrium after forming several long linear lesions between adjacent pairs of pulmonary vein ostia according to the method of FIG. 9A.
Figure 9C:
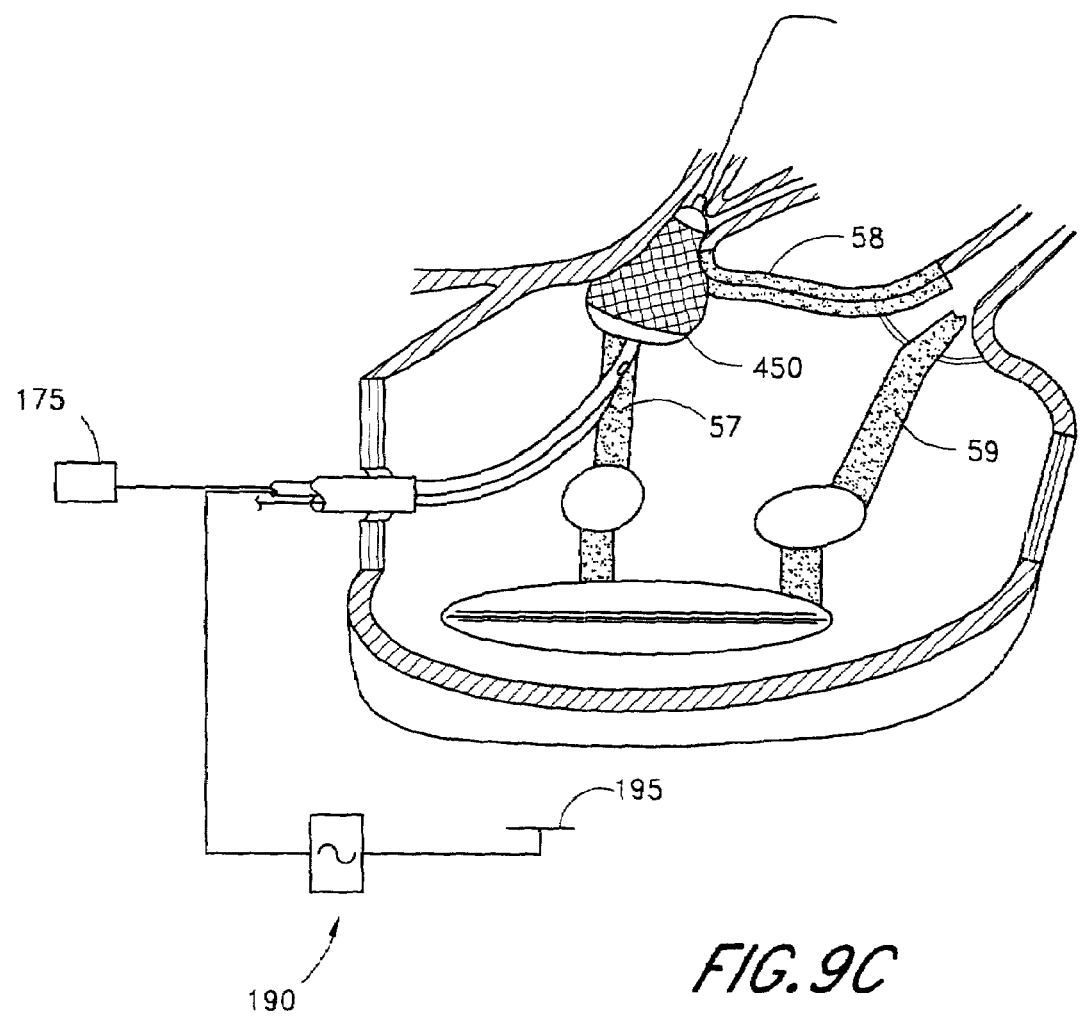
FIG. 9C shows a similar perspective view as that shown in FIG. 9B, although showing a circumferential ablation device assembly during use in forming a circumferential lesion at a location where a pulmonary vein extends from an atrium which intersects with two linear lesions that extend into the pulmonary vein, according to the method of FIG. 9A.
Figure 9D:
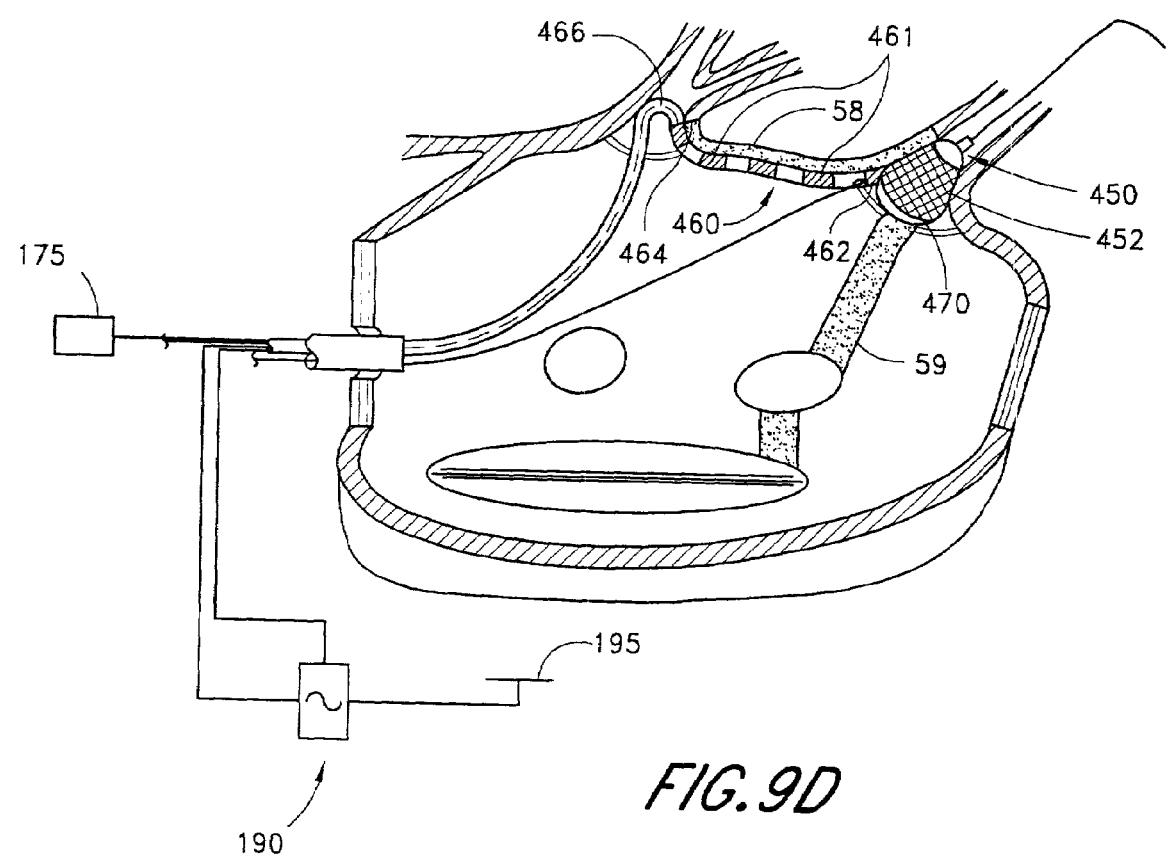
FIG. 9D shows a perspective view of another ablation catheter which combines a linear ablation member extending between two anchors with a circumferential ablation member for use in forming a circumferential lesion which intersects with at least one linear lesion according to the method of FIG. 9A.

In a further variation to the specific embodiments shown in FIGS. 9B–C, FIG. 9D shows another circumferential ablation device assembly, which includes both circumferential and linear ablation elements 452 and 461, respectively. Circumferential ablation member 450 is shown to include an expandable member 470 that is adjusted to a radially expanded position that is asymmetric to the underlying catheter shaft. Linear ablation member 460 extends along the elongate catheter body proximally from the circumferential ablation member 450. When expanded sufficiently to engage the pulmonary vein wall, expandable member 470 provides at least a portion of an anchor for a first end 462 of linear ablation member 460.

A shaped stylet 466 is shown in shadow in FIG. 9D within the elongate catheter body in the region of the second end 464 of the linear ablation member 460. Shaped stylet 466 is adapted to push the second end 464 into an adjacent pulmonary vein ostium such that the linear ablation member 460 is adapted to substantially contact the left atrial wall between the adjacent vein ostia to form the linear ablation according to the method of FIG. 9A. In addition to the use of shaped stylet 466, it is further contemplated that a different second anchor may be used adjacent to second end 464, such as for example an intermediate guidewire tracking member adapted to track over a guidewire engaged within the pulmonary vein, as shown in FIG. 9E at intermediate guidewire tracking member 466' which is engaged over guidewire 467.

Figure 9E:
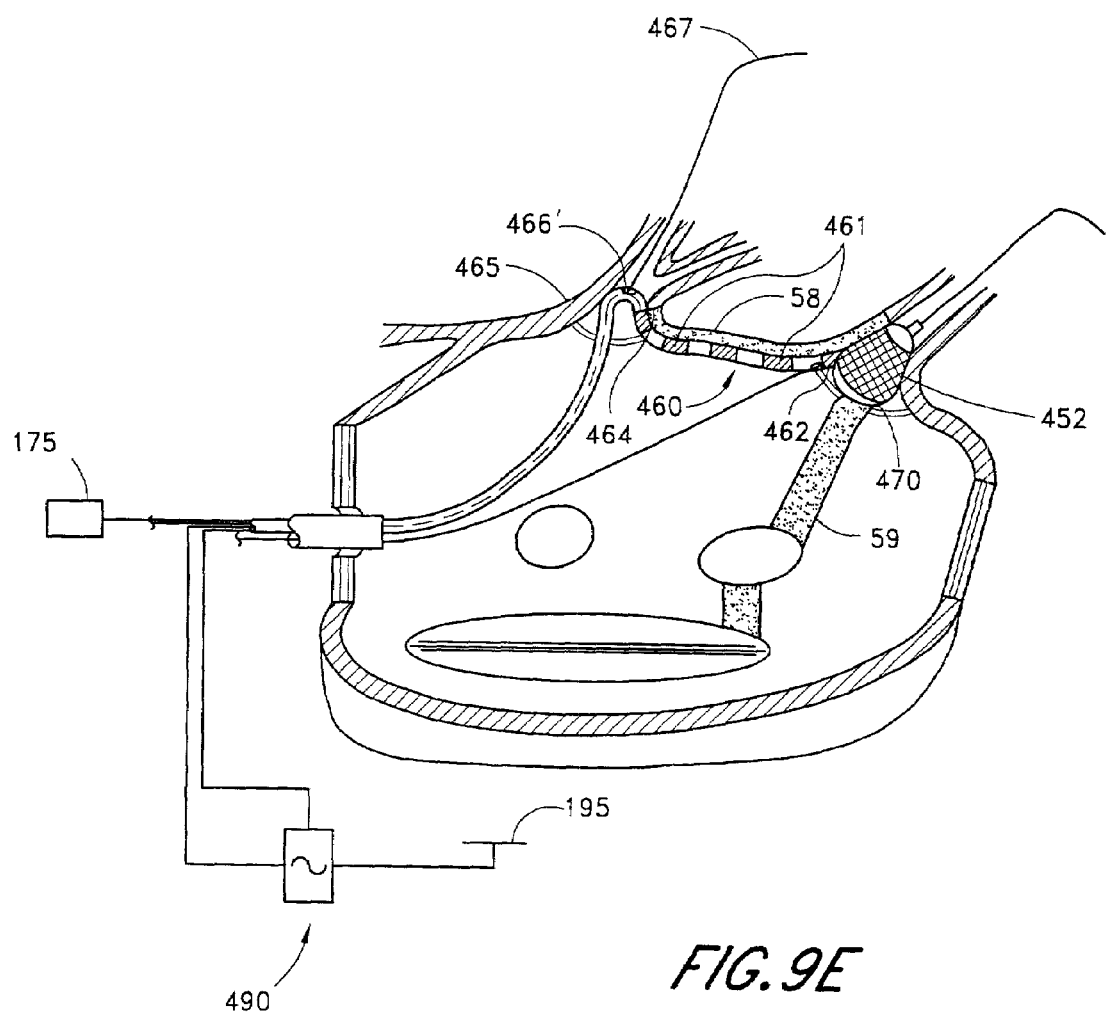
FIG. 9E shows a perspective view of another circumferential ablation catheter for use in forming a circumferential lesion that intersects with at least one linear lesion according to the method of FIG. 9A.

In a yet a further variation to the specific embodiment shown in FIG. 9D, FIG. 9E shows a circumferential ablation device assembly which includes both circumferential and linear ablation elements 452, 460, respectively. Circumferential ablation member 450 is shown to include an expandable member 470 which is adjusted to a radially expanded position that is asymmetric to the underlying catheter shaft. Linear ablation member 460 extends along the elongate body proximally from the circumferential ablation member 450. When expanded sufficiently to engage the pulmonary vein wall, expandable member 470 provides at least a portion of an anchor for a first end 462 of linear ablation member 460.

Moreover, the method shown schematically in FIG. 9A and also in various detail by reference to FIGS. 9B–C provides a specific sequence of steps for the purpose of illustration. According to this illustrative sequence, the linear lesions are formed first and then are connected thereafter with the circumferential conduction block. However, a circumferential conduction block may be formed prior to the formation of the linear lesions or conduction blocks, or in any other combination or sub-combination of sequential steps, so long as the resulting combination of lesions allows for the circumferential block to intersect with and connect with the linear lesions. In addition, the circumferential conduction block which connects the linear lesions may also include a circumferential path of tissue which surrounds and electrically isolates the pulmonary vein ostium from the rest of the left posterior atrial wall, such as for example by considering the embodiments just shown and described by reference to FIGS. 9A–E in view of the embodiment previously shown and described in relation to FIG. 8C above.

Figure 9F:
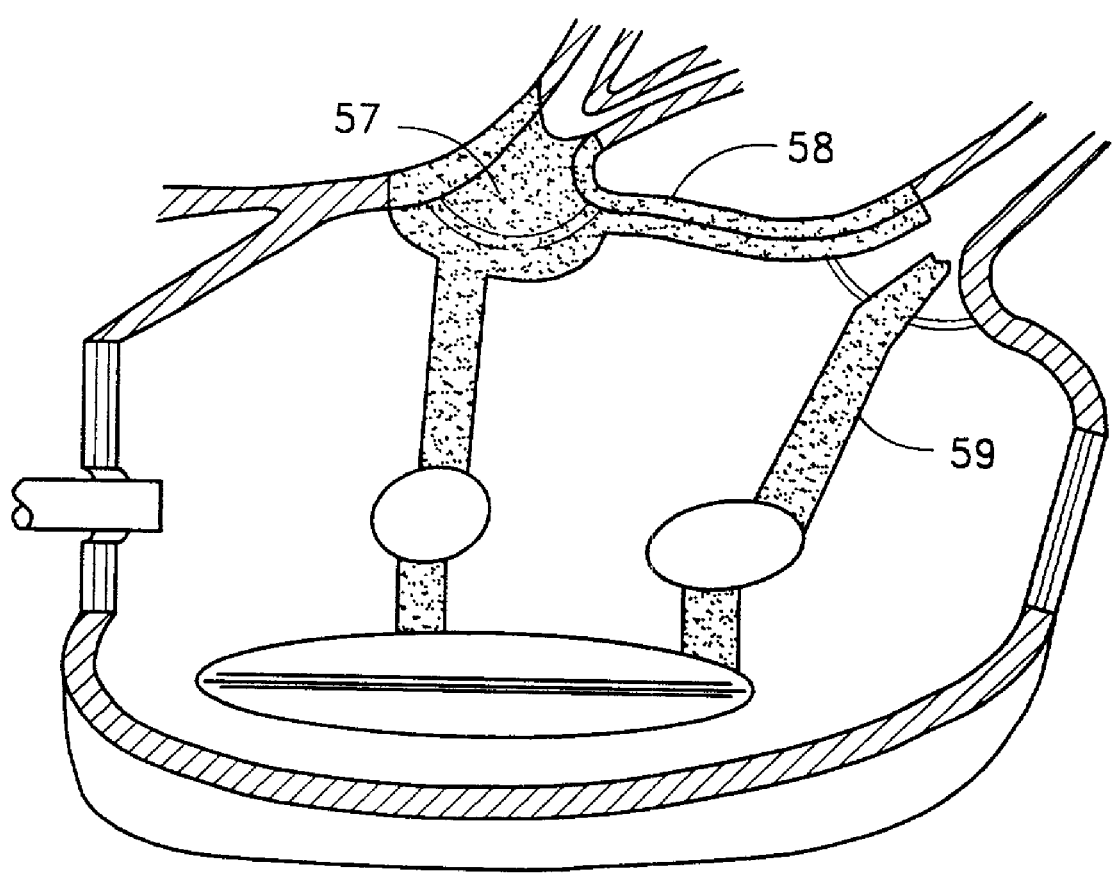
FIG. 9F shows a perspective view of a segmented left posterior atrial wall with a lesion pattern which results from combining the formation of two linear lesions according to FIG. 9B with the formation of a circumferential conduction block according to the methods and devices shown in FIGS. 8A–C.
Figure 9G:
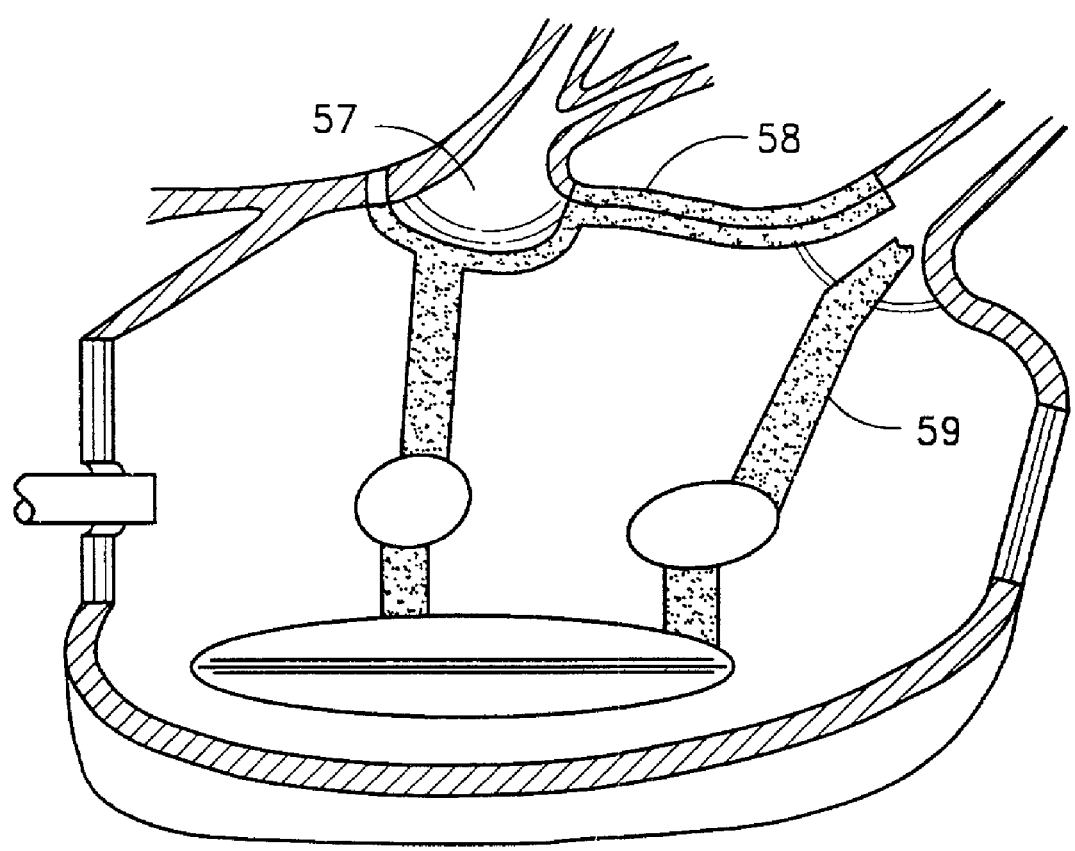
FIG. 9G shows a perspective view of a segmented left posterior atrial wall with a lesion pattern which results from combining the formation of two linear lesions according to FIG. 9B with the formation of a circumferential conduction block according to the methods and devices shown in FIGS. 8D–F.

In addition to the particular embodiments just shown and described by reference to FIGS. 9A–E, other methods are also contemplated for combining circumferential and linear conduction blocks device assemblies and uses in order to perform a less-invasive "maze"-type procedure. For example, FIG. 9F shows one particular lesion pattern which results by combining a circumferential conduction block 57, formed according to the previous embodiments of FIGS. 8A–C, with a pair of linear lesions which are formed according to the method illustrated by FIG. 9B. In a further example shown in FIG. 9G, another lesion pattern is formed by combining the pair of linear lesions of FIG. 9B with a circumferential conduction block formed according to the embodiments which are previously illustrated above by reference to FIGS. 9D–F. While the resulting lesion patterns of FIGS. 9F–G differ slightly as regards the particular geometry and position of the circumferential conduction block formed, the two variations are also similar in that the circumferential conduction block includes a circumferential path of atrial wall tissue. When such circumferential conduction blocks are formed between adjacent pulmonary vein ostia, shorter linear lesions are therefore sufficient to bridge the circumferential lesions during the overall "maze"-type procedure.

To this end, the invention further contemplates one further variation for a less-invasive "maze"-type procedure (not shown) wherein multiple circumferential conduction blocks are formed in atrial wall tissue such that each pulmonary vein ostium is surrounded by and is electrically isolated with one circumferential conduction block. A series of four linear lesions may be formed between the various pairs of adjacent ostia and with just sufficient length to intersect with and bridge the corresponding adjacent circumferential blocks. A box-like conduction block is thereby formed by the four circumferential conduction blocks and the four bridging linear lesions. A fifth linear lesion may be also formed between at least a portion of the box-like conduction block and another predetermined location, such as for example the mitral value annulus.

Figure 9H:
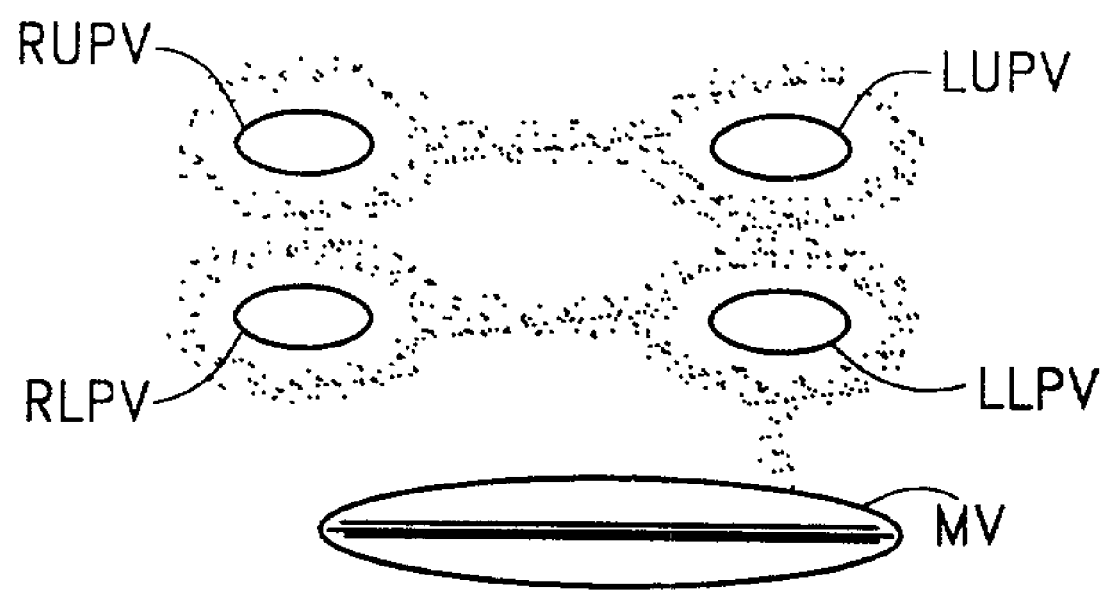
FIG. 9H shows a schematic perspective view of a left posterior atrial wall with one complete lesion pattern in a variation of a less-invasive "maze"-type procedure wherein circumferential conduction blocks are formed along circumferential paths of tissue along a left posterior atrial wall such that each circumferential conduction block surrounds a pulmonary vein ostium, each pair of vertically adjacent circumferential conduction blocks intersects, and each pair of horizontally adjacent circumferential conduction blocks are connected with one of two linear lesions extending between the respective pair of horizontally adjacent pulmonary vein ostia.

FIG. 9H shows yet a further variation for forming circumferential conduction blocks along atrial wall tissue around the pulmonary vein ostia during a less invasive "maze"-type procedure. According to this further variation, the circumferential conduction block patterns formed around each of two adjacent superior and inferior pulmonary vein ostia are shown in FIG. 9H to intersect, thereby alleviating the need for a linear lesion in order to form a conduction block between the ostia. Furthermore, the distances between the inferior and superior ostia, both on the right and left side of the posterior atrial wall, are believed to be significantly shorter than the distances between the two adjacent superior or inferior ostia. Therefore, FIG. 9H only shows the overlapping circumferential conduction blocks as just described to be positioned vertically between the inferior-superior pairs of adjacent ostia, and further shows linear lesions which are used to connect the right and left sided ostia of the superior and inferior pairs. In some instances these linear lesions will not be required to cure, treat or prevent a particular atrial arrhythmia condition. However, other combinations of these patterns are further contemplated, such as for example using only overlapping circumferential conduction blocks between all adjacent pairs of ostia in order to form the entire "maze"-type left atrial pattern.

Figure 10:
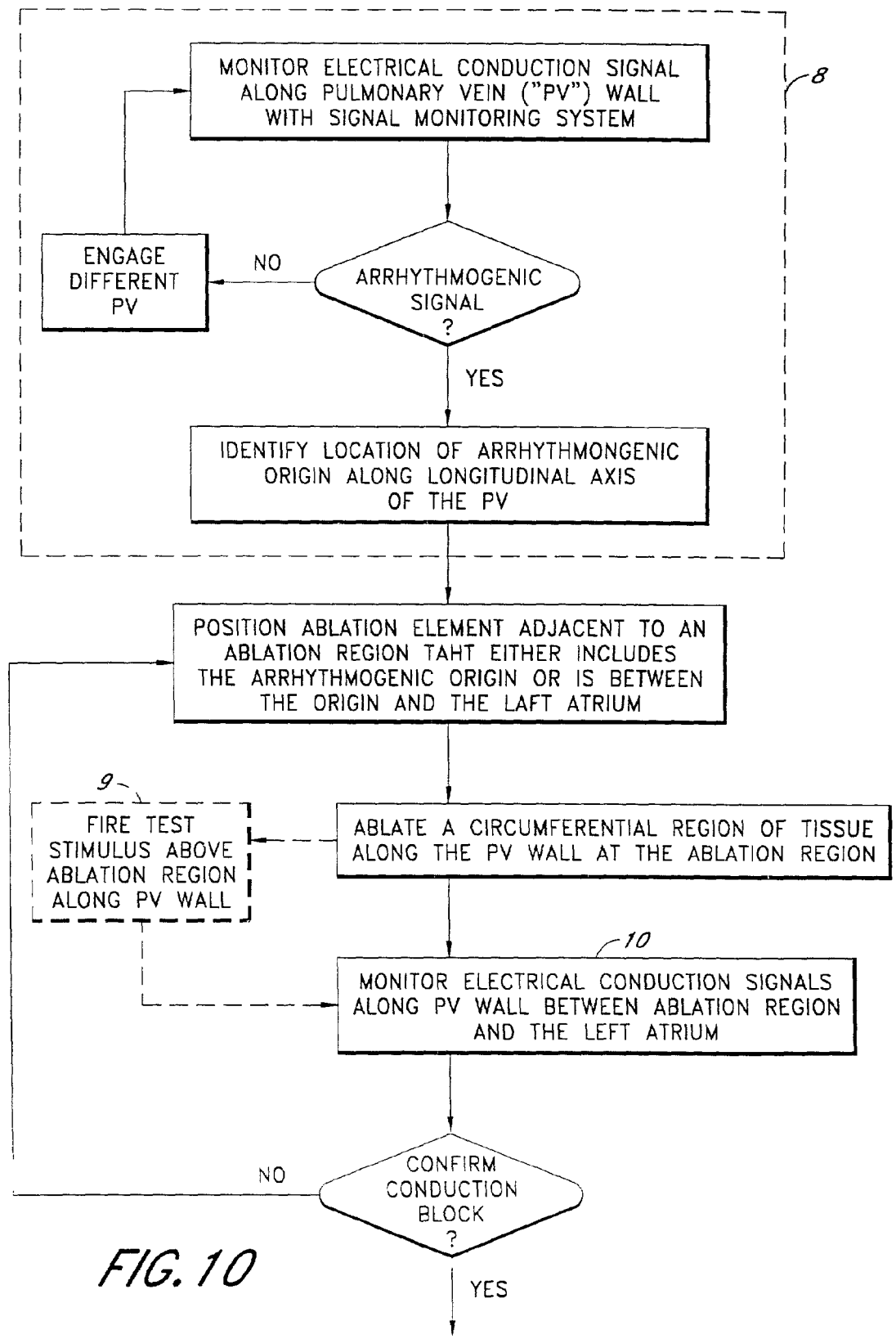
FIG. 10 diagrammatically shows a further method for using a circumferential ablation device assembly to form a circumferential conduction block at a location where a pulmonary vein extends from an atrium wall, wherein signal monitoring and "post-ablation" test elements are used to locate an arrhythmogenic origin along the pulmonary vein wall and to test the efficacy of a circumferential conduction block in the wall, respectively.

FIG. 10 diagrammatically shows a further method for using the circumferential ablation device assembly of the present invention wherein electrical signals along the pulmonary vein are monitored with a sensing element before and after ablation according to steps (8) and (9), respectively. Signals within the pulmonary vein are monitored prior to forming a conduction block, as indicated in step (8) in FIG. 10, in order to confirm that the pulmonary vein chosen contains an arrhythmogenic origin for atrial arrhythmia. Failure to confirm an arrhythmogenic origin in the pulmonary vein, particularly in the case of a patient diagnosed with focal arrhythmia, may dictate the need to monitor signals in another pulmonary vein in order to direct treatment to the proper location in the heart. In addition, monitoring the pre-ablation signals may be used to indicate the location of the arrhythmogenic origin of the atrial arrhythmia, which information helps determine the best location to form the conduction block. As such, the conduction block may be positioned to include and therefore ablate the actual focal origin of the arrhythmia, or may be positioned between the focus and the atrium in order to block aberrant conduction from the focal origin and into the atrial wall.

In addition or in the alternative to monitoring electrical conduction signals in the pulmonary vein prior to ablation, electrical signals along the pulmonary vein wall may also be monitored by the sensing element subsequent to circumferential ablation, according to step (9) of the method of FIG. 10. This monitoring method aids in testing the efficacy of the ablation in forming a complete conduction block against arrhythmogenic conduction. Arrhythmogenic firing from the identified focus will not be observed during signal monitoring along the pulmonary vein wall when taken below a continuous circumferential and transmural lesion formation, and thus would characterize a successful circumferential conduction block. In contrast, observation of such arrhythmogenic signals between the lesion and the atrial wall characterizes a functionally incomplete or discontinuous circumference (gaps) or depth (transmurality) which would potentially identify the need for a subsequent follow-up procedure, such as a second circumferential lesioning procedure in the ablation region.

A test electrode may also be used in a "post ablation" signal monitoring method according to step (10) of FIG. 10. In one particular embodiment not shown, the test electrode is positioned on the distal end portion of an elongate catheter body and is electrically coupled to a current source for firing a test signal into the tissue surrounding the test electrode when it is placed distally or "upstream" of the circumferential lesion in an attempt to simulate a focal arrhythmia. This test signal generally challenges the robustness of the circumferential lesion in preventing atrial arrhythmia from any such future physiologically generated aberrant activity along the suspect vein.

Further to the signal monitoring and test stimulus methods just described, such methods may be performed with a separate electrode or electrode pair located on the catheter distal end portion adjacent to the region of the circumferential ablation element, or may be performed using one or more electrodes which form the circumferential ablation element itself, as will be further developed below.

Expandable Member and Circumferential Ablation Element

The designs for the expandable member and circumferential ablation element for use in a circumferential ablation device assembly as herein described have been described generically with reference to the embodiments shown in the previous figures. Examples of various specific expandable member and ablation element structures that are adapted for use in such assemblies and methods are further provided as follows.

Notwithstanding their somewhat schematic detail, the circumferential ablation members shown in the previous figures do illustrate one particular embodiment wherein a circumferential electrode element circumscribes an outer surface of an expandable member. The expandable member of the embodiments shown may take one of several different forms, although the expandable member is generally herein shown as an inflatable balloon that is coupled to an expansion actuator which is a pressurizeable fluid source. The balloon is preferably made of a polymeric material and forms a fluid chamber which communicates with a fluid passageway (not shown in the figures) that extends proximally along the elongate catheter body and terminates proximally in a proximal fluid port that is adapted to couple to the pressurizeable fluid source.

In one expandable balloon variation, the balloon is constructed of a relatively inelastic polymer such as a polyethylene ("PE"; preferably linear low density or high density or blends thereof), polyolefin copolymer ("POC"), polyethylene terepthalate ("PET"), polyimide, or a nylon material. In this construction, the balloon has a low radial yield or compliance over a working range of pressures and may be folded into a predetermined configuration when deflated in order to facilitate introduction of the balloon into the desired ablation location via known percutaneous catheterization techniques. In this variation, one balloon size may not suitably engage all pulmonary vein walls for performing the circumferential ablation methods of the present invention on all needy patients. Therefore, it is further contemplated that a kit of multiple ablation catheters, with each balloon working length having a unique predetermined expanded diameter, may be provided from which a treating physician may chose a particular device to meet a particular patient's pulmonary vein anatomy.

In an alternative expandable balloon variation, the balloon is constructed of a relatively compliant, elastomeric material, such as, for example (but not limited to), a silicone, latex, polyurethane, or mylar elastomer. In this construction, the balloon takes the form of a tubular member in the deflated, non-expanded state. When the elastic tubular balloon is pressurized with fluid such as in the previous, relatively non-compliant example, the material forming the wall of the tubular member elastically deforms and stretches radially to a predetermined diameter for a given inflation pressure. It is further contemplated that the compliant balloon may be constructed as a composite, such as, for example, a latex or silicone balloon skin which includes fibers, such as metal, Kevlar, or nylon fibers, which are embedded into the skin. Such fibers, when provided in a predetermined pattern such as a mesh or braid, may provide a controlled compliance along a preferred axis, preferably limiting longitudinal compliance of the expandable member while allowing for radial compliance.

It is believed that, among other features, the relatively compliant variation may provide a wide range of working diameters, which may allow for a wide variety of patients, or of vessels within a single patient, to be treated with just one or a few devices. Furthermore, this range of diameters is achievable over a relatively low range of pressures, which is believed to diminish a potentially traumatic vessel response that may otherwise be presented concomitant with inflation at higher pressures, particularly when the inflated balloon is oversized to the vessel. In addition, the low-pressure inflation feature of this variation is suitable for the present invention because the functional requirement of the expandable balloon is merely to engage the ablation element against a circumferential path along the inner lining of the pulmonary vein wall.

Moreover, a circumferential ablation member is adapted to conform to the geometry of the pulmonary vein ostium, at least in part by providing substantial compliance to the expandable member, as was shown and described previously by reference to FIGS. 8A–B. Further to this conformability to pulmonary vein ostia as provided in the specific design of FIGS. 8A–B, the working length L of expandable member is also shown to include a taper which has a distally reducing outer diameter from a proximal end to a distal end. In either a compliant or the non-compliant balloon, such a distally reducing tapered geometry adapts the circumferential ablation element to conform to the funneling geometry of the pulmonary veins in the region of their ostia in order to facilitate the formation of a circumferential conduction block there.

Further to the circumferential electrode element embodiment as shown variously throughout the previous illustrative figures, the circumferential electrode element is coupled to an ablation actuator 190. Ablation actuator 190 generally includes a radio-frequency ("RF") current source (not shown) that is coupled to both the RF electrode element and also a ground patch 195 which is in skin contact with the patient to complete an RF circuit. In addition, ablation actuator 190 preferably includes a monitoring circuit (not shown) and a control circuit (not shown) which together use either the electrical parameters of the RF circuit or tissue parameters such as temperature in a feedback control loop to drive current through the electrode element during ablation. Also, where a plurality of ablation elements or electrodes in one ablation element are used, a switching means may be used to multiplex the RF current source between the various elements or electrodes.

FIGS. 11A–D show various patterns of electrically conductive, circumferential electrode bands as electrode ablation elements, each circumscribing an outer surface of the working length of an expandable member. FIGS. 11A–B show circumferential ablation member 550 to include a continuous circumferential electrode band 552 that circumscribes an outer surface of an expandable member 570. FIG. 11B more specifically shows expandable member 570 as a balloon which is fluidly coupled to a pressurizeable fluid source 175, and further shows electrode band (circumferential ablation element) 552 electrically coupled via electrically conductive lead 554 to ablation actuator 190. In addition, a plurality of apertures 572 are shown in the balloon skin wall of expandable member 570 adjacent to electrode band 552. The purpose of these apertures 572 is to provide a positive flow of fluid such as saline or ringers lactate fluid into the tissue surrounding the electrode band 552. Such fluid flow is believed to reduce the temperature rise in the tissue surrounding the electrode element during RF ablation.

The shapes shown collectively in FIGS. 11A–D allow for a continuous electrode band to circumscribe an expandable member's working length over a range of expanded diameters, a feature which is believed to be particularly useful with a relatively compliant balloon as the expandable member. In the particular embodiments of FIGS. 11A–D, this feature is provided primarily by a secondary shape given to the electrode band relative to the longitudinal axis of the working length of the expandable member. Electrode band 552 is thus shown in FIGS. 11A–B to take the specific secondary shape of a modified step curve. Other shapes than a modified step curve are also suitable, such as the serpentine or sawtooth secondary shapes shown respectively in FIGS. 11C–D. Other shapes in addition to those shown in FIGS. 11A–D and which meet the defined functional requirements are further contemplated within the scope of the present invention.

In addition, the electrode band provided by the circumferential ablation elements shown in FIGS. 11C–D and also shown schematically in FIGS. 3–6B has a functional band width w relative to the longitudinal axis of the working length which is only required to be sufficiently wide to form a complete conduction block against conduction along the walls of the pulmonary vein in directions parallel to the longitudinal axis. In contrast, the working length L of the respective expandable element is adapted to securely anchor the distal end portion in place such that the ablation element is firmly positioned at a selected region of the pulmonary vein for ablation. Accordingly, the band width w is relatively narrow compared to the working length L of the expandable element, and the electrode band may thus form a relatively narrow equatorial band which has a band width that is less than two-thirds or even one-half of the working length of the expandable element. Additionally, it is to be noted here and elsewhere throughout the specification, that a narrow band may be placed at locations other than the equator of the expandable element, preferably as long as the band is bordered on both sides by a portion of the working length L.

In another aspect of the narrow equatorial band variation for the circumferential ablation element, the circumferential lesion formed may also be relatively narrow when compared to its own circumference, and may be less than two-thirds or even one-half its own circumference on the expandable element when expanded. In one arrangement which is believed to be suitable for ablating circumferential lesions in the pulmonary veins as conduction blocks, the band width w is less than 1 cm with a circumference on the working length when expanded that is greater than 1.5 cm.

FIGS. 12A–B show a further variation of a circumferential ablation element which is adapted to maintain a continuous circumferential lesion pattern over a range of expanded diameters and which includes electrode elements that form a relatively narrow equatorial band around the working length of an expandable balloon member. In this variation, a plurality of individual electrode/ablation elements 562 are included in the circumferential ablation element and are positioned in spaced arrangement along an equatorial band which circumscribes an outer surface of the expandable member's working length L.

The size and spacing between these individual electrode elements 562, when the balloon is expanded, is adapted to form a substantially continuous circumferential lesion at a location where a pulmonary vein extends from an atrium when in intimal contact adjacent thereto, and is further adapted to form such a lesion over a range of band diameters as the working length is adjusted between a variety of radially expanded positions. Each individual electrode element 562 has two opposite ends 563, 564, respectively, along a long axis LA and also has a short axis SA, and is positioned such that the long axis LA is at an acute angle relative to the longitudinal axis La of the elongate catheter body and expandable member 560. At least one of the ends 563, 564 along the long axis LA overlaps with an end of another adjacent individual electrode element, such that there is a region of overlap along their circumferential aspect, i.e., there is a region of overlap along the circumferential coordinates. The terms "region of overlap along their circumferential coordinate" are herein intended to mean that the two adjacent ends each are positioned along the working length with a circumferential and also a longitudinal coordinate, wherein they share a common circumferential coordinate. In this arrangement, the circumferential compliance along the working length, which accompanies radial expansion of the expandable member, also moves the individual electrode elements apart along the circumferential axis. However, the spaced, overlapping arrangement described allows the individual ablation elements to maintain a certain degree of their circumferential overlap, or at least remain close enough together, such that a continuous lesion may be formed without gaps between the elements.

The construction for suitable circumferential electrode elements in the RF variation of the present invention, such as the various electrode embodiments described with reference to FIGS. 11A–12B, may comprise a metallic material deposited on the outer surface of the working length using conventional techniques, such as by plasma depositing, sputter coating, chemical vapor deposition, other known techniques which are equivalent for this purpose, or otherwise affixing a metallic shaped member onto the outer surface of the expandable member such as through known adhesive bonding techniques. Other RF electrode arrangements are also considered within the scope of the present invention, so long as they form a circumferential conduction block as previously described. For example, a balloon skin may itself be metallized, such as by mixing conductive metal, including but not limited to gold, platinum, or silver, with a polymer to form a compounded, conductive matrix as the balloon skin.

Still further to the RF electrode embodiments, another circumferential ablation member variation (not shown) may also include an expandable member, such as an inflatable balloon, that includes a porous skin that is adapted to allow fluid, such as hypertonic saline solution, to pass from an internal chamber defined by the skin and outwardly into surrounding tissues. Such a porous skin may be constructed according to several different methods, such as by forming holes in an otherwise contiguous polymeric material, including mechanically drilling or using laser energy, or the porous skin may simply be an inherently porous membrane. In any case, by electrically coupling the fluid within the porous balloon skin to an RF current source (preferably monopolar), the porous region of the expandable member serves as an RF electrode wherein RF current flows outwardly through the pores via the conductive fluid. In addition, it is further contemplated that a porous outer skin may be provided externally of another, separate expandable member, such as a separate expandable balloon, wherein the conductive fluid is contained in a region between the porous outer skin and the expandable member contained therein. Various other "fluid electrode" designs than those specifically herein described may also be suitable according to one of ordinary skill upon review of this disclosure.

In the alternative, or in addition to the RF electrode variations just described, the circumferential ablation element may also include other ablative energy sources or sinks, and particularly may include a thermal conductor that circumscribes the outer circumference of the working length of an expandable member. Examples of suitable thermal conductor arrangements include a metallic element that may, for example, be constructed as previously described for the more detailed RF embodiments above. However, in the thermal conductor embodiment such a metallic element would be generally either resistively heated in a closed loop circuit internal to the catheter, or conductively heated by a heat source coupled to the thermal conductor. In the latter case of conductive heating of the thermal conductor with a heat source, the expandable member may be, for example, a polymeric balloon skin which is inflated with a fluid that is heated either by a resistive coil or by bipolar RF current. In any case, it is believed that a thermal conductor on the outer surface of the expandable member is suitable when it is adapted to heat tissue adjacent thereto to a temperature between 40° and 80° C.

Further to the thermal conduction variation for the circumferential ablation element, the perfusion balloon embodiment as shown in FIGS. 6A–B may be particularly useful in such a design. It is believed that ablation through increased temperatures, as provided by example above may also enhance coagulation of blood in the pulmonary vein adjacent to the expandable member, which blood would otherwise remain stagnant without such a perfusion feature.

One further circumferential ablation element design which is believed to be highly useful in performing the methods according to the present invention is shown in FIG. 13 to include a circumferential ablation member 600 with two insulators 602, 604 that encapsulate the proximal and distal ends, respectively, of the working length L of an expandable member 610. In the particular embodiment shown, the insulators 602, 604 are thermal insulators, such as a thermal insulator comprising a Teflon material. Expandable member 610 is an inflatable balloon which has a balloon skin 612 that is thermally conductive to surrounding tissue when inflated with a heated fluid that may contain a radiopaque agent, saline fluid, ringers lactate, combinations thereof, and/or other known biocompatible fluids having acceptable heat transfer properties for these purposes. By providing these spaced insulators, a circumferential ablation element is formed as an equatorial band 603 of uninsulated balloon skin located between the opposite insulators. In this configuration, the circumferential ablation element is able to conduct heat externally of the balloon skin much more efficiently at the uninsulated equatorial band 603 than at the insulated portions, and thereby is adapted to ablate only a circumferential region of tissue in a pulmonary vein wall which is adjacent to the equatorial band. It is further noted that this embodiment is not limited to an "equatorial" placement of the ablation element. Rather, a circumferential band may be formed anywhere along the working length of the expandable member and circumscribing the longitudinal axis of the expandable member as previously described.

FIG. 13 further shows use of a radiopaque marker 620 to identify the location of the equatorial band 603 in order to facilitate placement of that band at a selected ablation region of a pulmonary vein via X-ray visualization. Radiopaque marker 620 is opaque under X-ray, and may be constructed, for example, of a radiopaque metal such as gold, platinum, or tungsten, or may comprise a radiopaque polymer such as a metal loaded polymer. FIG. 13 shows radiopaque marker 620 positioned coaxially over an inner tubular member 621 which is included in a coaxial catheter design as would be apparent to one of ordinary skill. Such a radiopaque marker may also be combined with the other embodiments herein shown and described. When the circumferential ablation member that forms an equatorial band includes a metallic electrode element, such electrode may itself be radiopaque and may not require use of a separate marker as just described.

The thermal insulator embodiment just described by reference to FIG. 13 is illustrative of a broader embodiment, wherein a circumferential ablation member has an ablating surface along the entire working length of an expandable member, but is shielded from releasing ablative energy into surrounding tissues except for along an unshielded or uninsulated equatorial band. As such, the insulator embodiment contemplates other ablation elements, such as the RF embodiments previously described above, which are provided along the entire working length of an expandable member and which are insulated at their ends to selectively ablate tissue only about an uninsulated equatorial band.

In a further example using the insulator embodiment in combination with a circumferential RF electrode embodiment, a metallized balloon which includes a conductive balloon skin may have an electrical insulator, such as a polymeric coating, at each end of the working length and thereby selectively ablate tissue with electricity flowing through the uninsulated equatorial band. In this and other insulator embodiments, it is further contemplated that the insulators described may be only partial and still provide the equatorial band result. For instance, in the conductive RF electrode balloon case, a partial electrical insulator will allow a substantial component of current to flow through the uninsulated portion due to a "shorting" response to the lower resistance in that region.

In still a further example of an insulator combined with a RF ablation electrode, a porous membrane comprises the entire balloon skin of an expandable member. By insulating the proximal and distal end portions of the working length of the expandable member, only the pores in the unexposed equatorial band region are allowed to effuse the electrolyte that carries an ablative RF current.

Further to the expandable member design for use in a circumferential ablation element according to the present invention, other expandable members than a balloon are also considered suitable. For example, in one expandable cage embodiment shown in FIG. 14, cage 650 comprises coordinating wires 651 and is expandable to engage a desired ablation region at a location where a pulmonary vein extends from an atrium.

The radial expansion of cage 650 is accomplished as follows. Sheath 652 is secured around the wires proximally of cage 650. However, core 653, which may be a metallic mandrel such as stainless steel, extends through sheath 652 and distally within cage 650 wherein it terminates in a distal tip 656. Wires 651 are secured to distal tip 656, for example, by soldering, welding, adhesive bonding, heat shrinking a polymeric member over the wires, or any combination of these methods. Core 653 is slideable within sheath 652, and may, for example, be housed within a tubular lumen (not shown) within sheath 652, the wires being housed between a coaxial space between the tubular lumen and sheath 652. By moving the sheath 652 relative to core 653 and distal tip 656 (shown by arrows in FIG. 14), the cage 650 is collapsible along its longitudinal axis in order to force an outward radial bias (also shown with arrows in FIG. 14) to wires 651 in an organized fashion to form a working length of cage 650 which is expanded (not shown).

Figure 14:
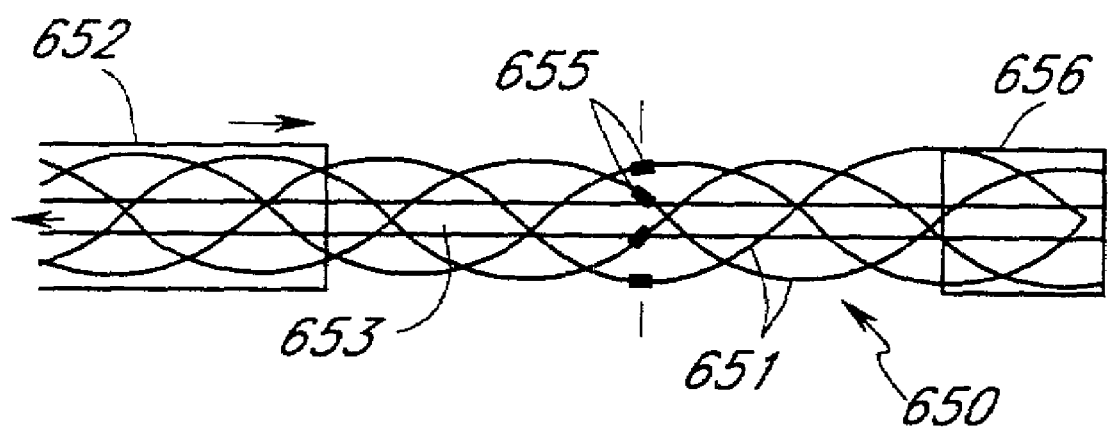
FIG. 14 shows a perspective view of another circumferential ablation member which is adapted for use in a circumferential ablation device assembly, wherein the expandable member is shown to be a cage of coordinating wires which are adapted to be adjusted from a radially collapsed position to a radially expanded position in order to engage electrode elements on the wires about a circumferential pattern of tissue at a location where a pulmonary vein extends from an atrium.

Further to the particular expandable cage embodiment shown in FIG. 14, a plurality of ablation electrodes 655 is shown, each being positioned on one of wires 651 and being similarly located along the longitudinal axis of the cage 650. The radial bias given to wires 651 during expansion, together with the location of the ablation electrodes 655, serves to position the plurality of ablation electrodes/elements 655 along a circumferential, equatorial band along the expanded working length of cage 650. The wires forming a cage according to this embodiment may also have another predetermined shape when in the radially expanded position. For example, a taper similar to that shown for expandable member 370 in FIG. 8A may be formed by expanding cage 650, wherein the ablation element formed by ablation electrodes 655 may be positioned between the proximal end and the distal end of the taper.

Further to the construction of the embodiment shown in FIG. 14, wires 651 are preferably metal, and may comprise stainless steel or a superelastic metal alloy, such as an alloy of nickel and titanium, or a combination of both. Regarding the case of nickel and titanium construction for the wires 655, a separate electrical conductor may be required in order to actuate ablation electrodes 655 to efficiently emit ablative current into surrounding tissues. In the case where wires 651 are constructed of stainless steel, they may also serve as electrical conductors for ablation electrodes 655. Further to the stainless steel design, the wires 651 may be coated with an electrical insulator to isolate the electrical flow into surrounding tissues at the site of the ablation electrodes 655. Moreover, the ablation electrodes 655 in the stainless steel wire variation may be formed simply by removing electrical insulation in an isolated region to allow for current to flow into tissue only from that exposed region.

In a further cage embodiment (not shown) to that shown in FIG. 14, a circumferential strip of electrodes may also be secured to the cage such that the strip circumscribes the cage at a predetermined location along the cage's longitudinal axis. By expanding cage as previously described, the strip of electrodes are adapted to take a circumferential shape according to the shape of the expanded cage. Such an electrode strip is preferably flexible, such that it may be easily reconfigured when the cage is adjusted between the radially collapsed and expanded positions and such that the strip may be easily advanced and withdrawn with the cage within the delivery sheath. Furthermore, the electrode strip may be a continuous circumferential electrode such as a conductive spring coil, or may be a flexible strip that includes several separate electrodes along its circumferential length. In the latter case, the flexible strip may electrically couple all of the electrodes to a conductive lead that interfaces with a drive circuit, or each electrode may be separately coupled to one or more such conductive leads.

FIGS. 15A–18B show various specific embodiments of a circumferential ablation device assembly that utilizes an ultrasonic energy source to ablate tissue. The present circumferential ablation device has particular utility in connection with forming a circumferential lesion within or about a pulmonary vein ostium or within the vein itself in order to form a circumferential conductive block. This application of the present ablation device, however, is merely an example, and it is understood that those skilled in the art can readily adapt the present ablation device for applications in other body spaces.

As common to each of the following embodiments, a source of acoustic energy is provided. A delivery device is also provided that includes an anchoring mechanism. In one mode, the anchoring device comprises an expandable member that also positions the acoustic energy source within the body; however, other anchoring and positioning devices may also be used, such as, for example, a basket mechanism. In a more specific form, the acoustic energy source is located within the expandable member and the expandable member is adapted to engage a circumferential path of tissue either about or along a pulmonary vein in the region of its ostium along a left atrial wall. The acoustic energy source in turn is acoustically coupled to the wall of the expandable member and thus to the circumferential region of tissue engaged by the expandable member wall by emitting a circumferential and longitudinally collimated ultrasound signal when actuated by an acoustic energy driver. The use of acoustic energy, and particularly ultrasonic energy, offers the advantage of simultaneously applying a dose of energy sufficient to ablate a relatively large surface area within or near the heart to a desired heating depth without exposing the heart to a large amount of current. For example, a collimated ultrasonic transducer can form a lesion, which has about a 1.5 mm width, about a 2.5 mm diameter lumen, such as a pulmonary vein and of a sufficient depth to form an effective conductive block. It is believed that an effective conductive block can be formed by producing a lesion within the tissue that is transmural or substantially transmural. Depending upon the patient as well as the location within the pulmonary vein ostium, the lesion may have a depth of about 1 to 10 mm. It has been observed that the collimated ultrasonic transducer can be powered to provide a lesion having these parameters so as to form an effective conductive block between the pulmonary vein and the posterior wall of the left atrium.

With specific reference now to the embodiment illustrated in FIGS. 15A–D, a circumferential ablation device assembly 800 includes an elongate catheter body 802 with proximal and distal end portions 810, 812, an expandable balloon 820 located along the distal end portion 812 of elongate catheter body 802, and a circumferential ultrasound transducer 830 which forms a circumferential ablation member that is acoustically coupled to the expandable balloon 820. In more detail, FIGS. 15A–C variously show elongate catheter body 802 to include guidewire lumen 804, inflation lumen 806, and electrical lead lumen 808. The ablation device, however, can be of a self-steering type rather than an over-the-wire type device.

Each lumen extends between a proximal port (not shown) and a respective distal port, which distal ports are shown as distal guidewire port 805 for guidewire lumen 804, distal inflation port 807 for inflation lumen 806, and distal lead port 809 for electrical lead lumen 808. Although the guidewire, inflation and electrical lead lumens are generally arranged in a side-by-side relationship, the elongate catheter body 802 can be constructed with one or more of these lumens arranged in a coaxial relationship, or in any of a wide variety of configurations that will be readily apparent to one of ordinary skill in the art.

In addition, the elongate catheter body 802 is also shown in FIGS. 15A and 15C to include an inner member 803 which extends distally beyond distal inflation and lead ports 807,809, through an interior chamber formed by the expandable balloon 820, and distally beyond expandable balloon 820 where the elongate catheter body terminates in a distal tip. The inner member 803 forms the distal region for the guidewire lumen 804 beyond the inflation and lead ports, and also provides a support member for the cylindrical ultrasound transducer 830 and for the distal neck of the expansion balloon, as described in more detail below.

One more detailed construction for the components of the elongate catheter body 802 that is believed to be suitable for use in transeptal left atrial ablation procedures is as follows. The elongate catheter body 802 itself may have an outer diameter provided within the range of from about 5 French to about 10 French, and more preferable from about 7 French to about 9 French. The guidewire lumen preferably is adapted to slideably receive guidewires ranging from about 0.010 inch to about 0.038 inch in diameter, and preferably is adapted for use with guidewires ranging from about 0.018 inch to about 0.035 inch in diameter. Where a 0.035 inch guidewire is to be used, the guidewire lumen preferably has an inner diameter of 0.040 inch to about 0.042 inch. In addition, the inflation lumen preferably has an inner diameter of about 0.020 inch in order to allow for rapid deflation times, although it may vary based upon the viscosity of the inflation medium used, length of the lumen, and other dynamic factors relating to fluid flow and pressure.

In addition to providing the requisite lumens and support members for the ultrasound transducer assembly, the elongate catheter body 802 of the present embodiment must also be adapted to be introduced into the left atrium such that the distal end portion with balloon and transducer may be placed within the pulmonary vein ostium in a percutaneous translumenal procedure, and even more preferably in a transeptal procedure as otherwise herein provided. Therefore, the distal end portion 812 is preferably flexible and adapted to track over and along a guidewire seated within the targeted pulmonary vein. In one further more detailed construction which is believed to be suitable, the proximal end portion is adapted to be at least 30% stiffer than the distal end portion. According to this relationship, the proximal end portion may be suitably adapted to provide push transmission to the distal end portion while the distal end portion is suitably adapted to track through bending anatomy during in vivo delivery of the distal end portion of the device into the desired ablation region.

Notwithstanding the specific device constructions just described, other delivery mechanisms for delivering the ultrasound ablation member to the desired ablation region are also contemplated. For example, while the FIG. 15A variation is shown as an "over-the-wire" catheter construction, other guidewire tracking designs may be suitable substitutes, such as, for example, catheter devices which are known as "rapid exchange" or "monorail" variations wherein the guidewire is only housed coaxially within a lumen of the catheter in the distal regions of the catheter. In another example, a deflectable tip design may also be a suitable substitute and which is adapted to independently select a desired pulmonary vein and direct the transducer assembly into the desired location for ablation. Further to this latter variation, the guidewire lumen and guidewire of the FIG. 15A variation may be replaced with a "pull wire" lumen and associated fixed pull wire which is adapted to deflect the catheter tip by applying tension along varied stiffness transitions along the catheter's length. Still further to this pull wire variation, acceptable pull wires may have a diameter within the range from about 0.008 inch to about 0.020 inch, and may further include a taper, such as, for example, a tapered outer diameter from about 0.020 inch to about 0.008 inch.

More specifically regarding expandable balloon 820 as shown in varied detail between FIGS. 15A and 15C, a central region 822 is generally coaxially disposed over the inner member 803 and is bordered at its end neck regions by proximal and distal adaptions 824, 826. The proximal adaption 824 is sealed over elongate catheter body 802 proximally of the distal inflation and the electrical lead ports 807, 809, and the distal adaption 826 is sealed over inner member 803. According to this arrangement, a fluid tight interior chamber is formed within expandable balloon 820. This interior chamber is fluidly coupled to a pressurizeable fluid source (not shown) via inflation lumen 806. In addition to the inflation lumen 806, electrical lead lumen 808 also communicates with the interior chamber of expandable balloon 820 so that the ultrasound transducer 830, which is positioned within that chamber and over the inner member 803, may be electrically coupled to an ultrasound drive source or actuator, as will be provided in more detail below.

The expandable balloon 820 may be constructed from a variety of known materials, although the balloon 820 preferably is adapted to conform to the contour of a pulmonary vein ostium. For this purpose, the balloon material can be of the highly compliant variety, such that the material elongates upon application of pressure and takes on the shape of the body lumen or space when fully inflated. Suitable balloon materials include elastomers, such as, for example, but without limitation, Silicone, latex, or low durometer polyurethane (for example, a durometer of about 80 A).

In addition or in the alternative to constructing the balloon of highly compliant material, the balloon 820 can be formed to have a predefined fully inflated shape (i.e., be preshaped) to generally match the anatomic shape of the body lumen in which the balloon is inflated. For instance, as described below in greater detail, the balloon can have a distally tapering shape to generally match the shape of a pulmonary vein ostium, and/or can include a bulbous proximal end to generally match a transition region of the atrium posterior wall adjacent to the pulmonary vein ostium. In this manner, the desired seating within the irregular geometry of a pulmonary vein or vein ostium can be achieved with both compliant and non-compliant balloon variations.

Notwithstanding the alternatives which may be acceptable as just described, the balloon 820 is preferably constructed to exhibit at least 300% expansion at 3 atmospheres of pressure, and more preferably to exhibit at least 400% expansion at that pressure. The term "expansion" is herein intended to mean the balloon outer diameter after pressurization divided by the balloon inner diameter before pressurization, wherein the balloon inner diameter before pressurization is taken after the balloon is substantially filled with fluid in a taut configuration. In other words, "expansion" is herein intended to relate to change in diameter that is attributable to the material compliance in a stress strain relationship. In one more detailed construction which is believed to be suitable for use in most conduction block procedures in the region of the pulmonary veins, the balloon is adapted to expand under a normal range of pressure such that its outer diameter may be adjusted from a radially collapsed position of about 5 mm to a radially expanded position of about 2.5 cm (or approximately 500% expansion ratio).

The ablation member illustrated in FIGS. 15A–D, takes the form of annular ultrasonic transducer 830. In the illustrated embodiment, the annular ultrasonic transducer 830 has a unitary cylindrical shape with a hollow interior (i.e., is tubular shaped); however, the transducer applicator 830 can have a generally annular shape and be formed of a plurality of segments. For instance, the transducer applicator 830 can be formed by a plurality of tube sectors that together form an annular shape. The tube sectors can also be of sufficient arc lengths so as when joined together, the sector assembly forms a "clover-leaf" shape. This shape is believed to provide overlap in heated regions between adjacent elements. The generally annular shape can also be formed by a plurality of planar transducer segments that are arranged in a polygon shape (e.g., hexagon). In addition, although in the illustrated embodiment the ultrasonic transducer comprises a single transducer element, the transducer applicator can be formed of a multi-element array, as described in greater detail below.

As is shown in detail in FIG. 15D, cylindrical ultrasound transducer 830 includes a tubular wall 831 with three concentric tubular layers. The central layer 832 is a tubular shaped member of a piezoceramic or piezoelectric crystalline material. The transducer preferably is made of type PZT-4, PZT-5 or PZT-8, quartz or Lithium-Niobate type piezoceramic material to ensure high power output capabilities. These types of transducer materials are commercially available from Stavely Sensors, Inc. of East Hartford, Conn., or from Valpey-Fischer Corp. of Hopkinton, Mass.

The outer and inner tubular members 833, 834 enclose central layer 832 within their coaxial space and are constructed of an electrically conductive material. In the illustrated embodiment, these transducer electrodes 833, 834 comprise a metallic coating, and more preferably a coating of nickel, copper, silver, gold, platinum, or alloys of these metals.

One more detailed construction for a cylindrical ultrasound transducer for use in the present application is as follows. The length of the transducer 830 or transducer assembly (e.g., multi-element array of transducer elements) desirably is selected for a given clinical application. In connection with forming circumferential conduction blocks in cardiac or pulmonary vein wall tissue, the transducer length can fall within the range of approximately 2 mm up to greater than 10 mm, and preferably equals about 5 to 10 mm. A transducer accordingly sized is believed to form a lesion of a width sufficient to ensure the integrity of the formed conductive block without undue tissue ablation. For other applications, however, the length can be significantly longer.

Likewise, the transducer outer diameter desirably is selected to account for delivery through a particular access path (e.g., percutaneously and transseptally), for proper placement and location within a particular body space, and for achieving a desired ablation effect. In the given application within or proximate of the pulmonary vein ostium, the transducer 830 preferably has an outer diameter within the range of about 1.8 mm to greater than 2.5 mm. It has been observed that a transducer with an outer diameter of about 2 mm generates acoustic power levels approaching 20 Watts per centimeter radiator or greater within myocardial or vascular tissue, which is believed to be sufficient for ablation of tissue engaged by the outer balloon for up between 2–3 cm outer diameter of the balloon. For applications in other body spaces, the transducer applicator 830 may have an outer diameter within the range of about 1 mm to greater than 3–4 mm (e.g., as large as 1 to 2 cm for applications in some body spaces).

The central layer 832 of the transducer 830 has a thickness selected to produce a desired operating frequency. The operating frequency will vary of course depending upon clinical needs, such as the tolerable outer diameter of the ablation and the depth of heating, as well as upon the size of the transducer as limited by the delivery path and the size of the target site. As described in greater detail below, the transducer 830 in the illustrated application preferably operates within the range of about 5 MHz to about 20 MHz, and more preferably within the range of about 7 MHz to about 10 MHz. Thus, for example, the transducer can have a thickness of approximately 0.3 mm for an operating frequency of about 7 MHz (i.e., a thickness generally equal to ½ the wavelength associated with the desired operating frequency).

The transducer 830 is vibrated across the wall thickness and to radiate collimated acoustic energy in the radial direction. For this purpose, as best seen in FIGS. 15A and 15D, the distal ends of electrical leads 836, 837 are electrically coupled to outer and inner tubular members or electrodes 833, 834, respectively, of the transducer 830, such as, for example, by soldering the leads to the metallic coatings or by resistance welding. In the illustrated embodiment, the electrical leads are 4–8 mil (0.004 to 0.008 inch diameter) silver wire or the like.

The proximal ends of these leads are adapted to couple to an ultrasonic driver or actuator 840, which is schematically illustrated in FIG. 15D. FIGS. 15A–D further show leads 836, 837 as separate wires within electrical lead lumen 808, in which configuration the leads must be well insulated when in close contact. Other configurations for leads 836, 837 are therefore contemplated. For example, a coaxial cable may provide one cable for both leads which is well insulated as to inductance interference. Or, the leads may be communicated toward the distal end portion 812 of the elongate catheter body through different lumens that are separated by the catheter body.

The transducer also can be sectored by scoring or notching the outer transducer electrode 833 and part of the central layer 832 along lines parallel to the longitudinal axis L of the transducer 830, as illustrated in FIG. 15E. A separate electrical lead connects to each sector in order to couple the sector to a dedicated power control that individually excites the corresponding transducer sector. By controlling the driving power and operating frequency to each individual sector, the ultrasonic driver 840 can enhance the uniformity of the ultrasonic beam around the transducer 830, as well as can vary the degree of heating (i.e., lesion control) in the angular dimension.

The ultrasound transducer just described is combined with the overall device assembly according to the present embodiment as follows. In assembly, the transducer 830 desirably is "air-backed" to produce more energy and to enhance energy distribution uniformity, as known in the art. In other words, the inner member 803 does not contact an appreciable amount of the inner surface of transducer inner tubular member 834. This is because the piezoelectric crystal which forms central layer 832 of ultrasound transducer 830 is adapted to radially contract and expand (or radially "vibrate") when an alternating current is applied from a current source and across the outer and inner tubular electrodes 833, 834 of the crystal via the electrical leads 836, 837. This controlled vibration emits the ultrasonic energy that is adapted to ablate tissue and form a circumferential conduction block according to the present embodiment. Therefore, it is believed that appreciable levels of contact along the surface of the crystal may provide a dampening effect that would diminish the vibration of the crystal and thus limit the efficiency of ultrasound transmission.

For this purpose, the transducer 830 seats coaxial about the inner member 803 and is supported about the inner member 803 in a manner providing a gap between the inner member 803 and the transducer inner tubular member 834. That is, the inner tubular member 834 forms an interior bore 835 that loosely receives the inner member 803. Any of a variety of structures can be used to support the transducer 830 about the inner member 803. For instance, spacers or splines can be used to coaxially position the transducer 830 about the inner member 803 while leaving a generally annular space between these components. In the alternative, other conventional and known approaches to support the transducer can also be used. For instance, O-rings that circumscribe the inner member 803 and lie between the inner member 803 and the transducer 830 can support the transducer 830 in a manner similar to that illustrated in U.S. Pat. No. 5,606,974 to Castellano issued Mar. 4, 1997, and entitled "Catheter Having Ultrasonic Device." More detailed examples of the alternative transducer support structures just described are disclosed in U.S. Pat. No. 5,620,479 to Diederich, issued Apr. 15, 1997, and entitled "Method and Apparatus for Thermal Therapy of Tumors." The disclosures of these references are herein incorporated in their entirety by reference thereto.

In the illustrated embodiment, at least one stand-off region 838 is provided along inner member 803 in order to ensure that the transducer 830 has a radial separation from the inner member 803 to form a gap filled with air and/or other fluid. In one preferred mode shown in FIG. 15C, stand-off region 838 is a tubular member with a plurality of circumferentially spaced outer splines 839 that hold the majority of the transducer inner surface away from the surface of the stand-off between the splines, thereby minimizing dampening affects from the coupling of the transducer to the catheter. The tubular member that forms a stand-off such as stand-off region 838 in the FIG. 15C embodiment may also provide its inner bore as the guidewire lumen in the region of the ultrasound transducer, in the alternative to providing a separate stand-off coaxially over another tubular member which forms the inner member, such as according to the FIG. 15C embodiment.

In a further mode, the elongate catheter body 802 can also include additional lumens which lie either side by side to or coaxial with the guidewire lumen 804 and which terminate at ports located within the space between the inner member 803 and the transducer 830. A cooling medium can circulate through space defined by the stand-off 838 between the inner member 803 and the transducer 830 via these additional lumens. By way of example, carbon dioxide gas, circulated at a rate of 5 liters per minute, can be used as a suitable cooling medium to maintain the transducer at a lower operating temperature. It is believed that such thermal cooling would allow more acoustic power to transmit to the targeted tissue without degradation of the transducer material.

The transducer 830 desirably is electrically and mechanically isolated from the interior of the balloon 820. Again, any of a variety of coatings, sheaths, sealants, tubing and the like may be suitable for this purpose, such as those described in U.S. Pat. No. 5,620,479 to Diederich and U.S. Pat. No. 5,606,974 to Castellano. In the illustrated embodiment, as best illustrated in FIG. 15C, a conventional, flexible, acoustically compatible, and medical grade epoxy 842 is applied over the transducer 830. The epoxy 842 may be, for example, Epotek 301, Epotek 310, which is available commercially from Epoxy Technology, or Tracon FDA-8. In addition, a conventional sealant, such as, for example, General Electric Silicon II gasket glue and sealant, desirably is applied at the proximal and distal ends of the transducer 830 around the exposed portions of the inner member 803, wires 836, 837 and stand-off region 838 to seal the space between the transducer 830 and the inner member 803 at these locations.

An ultra thin-walled polyester heat shrink tubing 844 or the like then seals the epoxy coated transducer. Alternatively, the epoxy covered transducer 830, inner member 803 along stand-off region 838 can be instead inserted into a tight thin wall rubber or plastic tubing made from a material such as Teflon®, polyethylene, polyurethane, silastic or the like. The tubing desirably has a thickness of 0.0005 to 0.003 inches.

When assembling the ablation device assembly, additional epoxy is injected into the tubing after the tubing is placed over the epoxy coated transducer 830. As the tube shrinks, excess epoxy flows out and a thin layer of epoxy remains between the transducer and the heat shrink tubing 844. These layers 842, 844 protect the transducer surface, help acoustically match the transducer 830 to the load, makes the ablation device more robust, and ensures air-tight integrity of the air backing.

Although not illustrated in FIG. 15A in order to simplify the drawing, the tubing 844 extends beyond the ends of transducer 830 and surrounds a portion of the inner member 803 on either side of the transducer 830. A filler (not shown) can also be used to support the ends of the tubing 844. Suitable fillers include flexible materials such as, for example, but without limitation, epoxy, Teflon® tape and the like.

The ultrasonic actuator 840 generates alternating current to power the transducer 830. The ultrasonic actuator 840 drives the transducer 830 at frequencies within the range of about 5 MHz to about 20 MHz, and preferably for the illustrated application within the range of about 7 MHz to about 10 MHz. In addition, the ultrasonic driver can modulate the driving frequencies and/or vary power in order to smooth or unify the produced collimated ultrasonic beam. For instance, the function generator of the ultrasonic actuator 840 can drive the transducer at frequencies within the range of 6.8 MHz and 7.2 MHz by continuously or discretely sweeping between these frequencies.

The ultrasound transducer 830 of the present embodiment sonically couples with the outer skin of the balloon 820 in a manner that forms a circumferential conduction block at a location where a pulmonary vein extends from an atrium as follows. Initially, the ultrasound transducer is believed to emit its energy in a circumferential pattern that is highly collimated along the transducer's length relative to its longitudinal axis L. The circumferential band therefore maintains its width and circumferential pattern over an appreciable range of diameters away from the source at the transducer. Also, the balloon is preferably inflated with fluid that is relatively ultrasonically transparent, such as, for example, degassed water. Therefore, by actuating the transducer 830 while the balloon 820 is inflated, the circumferential band of energy is allowed to translate through the inflation fluid and ultimately sonically couple with a circumferential band of balloon skin which circumscribes the balloon 820. Moreover, the circumferential band of balloon skin material may also be further engaged along a circumferential path of tissue which circumscribes the balloon, such as, for example, if the balloon is inflated within and engages a pulmonary vein wall, ostium, or region of atrial wall. Accordingly, where the balloon is constructed of a relatively ultrasonically transparent material, the circumferential band of ultrasound energy is allowed to pass through the balloon skin and into the engaged circumferential path of tissue such that the circumferential path of tissue is ablated.

Further to the transducer-balloon relationship just described, the energy is coupled to the tissue largely via the inflation fluid and balloon skin. It is believed that, for in vivo uses of the present invention, the efficiency of energy coupling to the tissue, and therefore ablation efficiency, may significantly diminish in circumstances where there is poor contact and conforming interface between the balloon skin and the tissue. Accordingly, it is contemplated that several different balloon types may be provided for ablating different tissue structures so that a particular shape may be chosen for a particular region of tissue to be ablated.

Figure 17A:
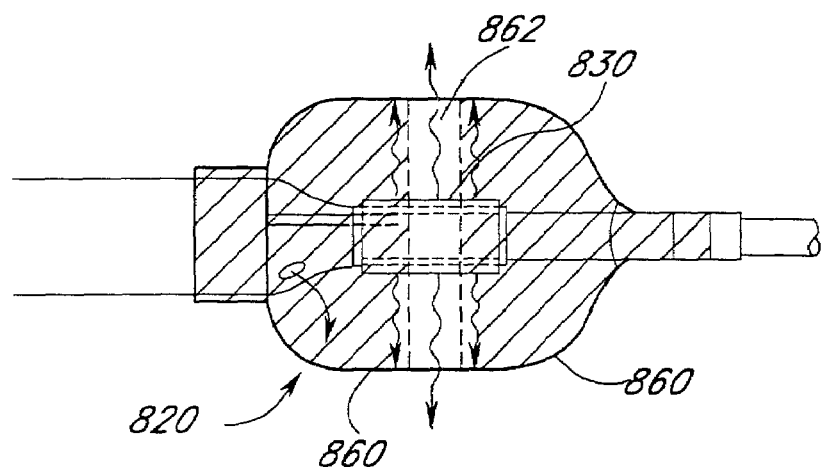
FIG. 17A shows a cross-sectional view of the distal end portion of another circumferential ablation catheter, wherein an outer shield or filter is provided along the balloon's outer surface in order to form a predetermined shape for the circumferential ablation element created by sonic transmissions from the inner ultrasound transducer.

In one particular balloon-transducer combination shown in FIG. 15A and also in FIG. 17A, the ultrasound transducer preferably has a length such that the ultrasonically coupled band of the balloon skin, having a similar length d according to the collimated ultrasound signal, is shorter than the working length D of the balloon. According to this aspect of the relationship, the transducer is adapted as a circumferential ablation member that is coupled to the balloon to form an ablation element along a circumferential band of the balloon, therefore forming a circumferential ablation element band that circumscribes the balloon. Preferably, the transducer has a length that is less than two-thirds the working length of the balloon, and more preferably is less than one-half the working length of the balloon. By sizing the ultrasonic transducer length d smaller than the working length D of the balloon 820—and hence shorter than a longitudinal length of the engagement area between the balloon 820 and the wall of the body space (e.g., pulmonary vein ostium)—and by generally centering the transducer 830 within the balloon's working length D, the transducer 830 operates in a field isolated from the blood pool. A generally equatorial position of the transducer 830 relative to the ends of the balloon's working length also assists in the isolation of the transducer 830 from the blood pool. It is believed that the transducer placement according to this arrangement may be preventative of thrombus formation that might otherwise occur at a lesion sight, particularly in the left atrium.

The ultrasound transducer described in various levels of detail above has been observed to provide a suitable degree of radiopacity for locating the energy source at a desired location for ablating the conductive block. However, it is further contemplated that the elongate catheter body 802 may include an additional radiopaque marker or markers (not shown) to identify the location of the ultrasonic transducer 830 in order to facilitate placement of the transducer at a selected ablation region of a pulmonary vein via X-ray visualization. The radiopaque marker is opaque under X-ray, and can be constructed, for example, of a radiopaque metal such as gold, platinum, or tungsten, or can comprise a radiopaque polymer such as a metal loaded polymer. The radiopaque marker is positioned coaxially over an inner tubular member 803.

The present circumferential ablation device is introduced into a pulmonary vein of the left atrium in a manner similar to that described above. Once properly positioned within the pulmonary vein or vein ostium, the pressurized fluid source inflates the balloon 820 to engage the lumenal surface of the pulmonary vein ostium. Once properly positioned, the ultrasonic driver 840 is energized to drive the transducer 830. It is believed that by driving the ultrasonic transducer 830 at 20 acoustical watts at an operating frequency of 7 MHz, that a sufficiently sized lesion can be formed circumferentially about the pulmonary vein ostium in a relatively short period of time (e.g., 1 to 2 minutes or less). It is also contemplated that the control level of energy can be delivered, then tested for lesion formation with a test stimulus in the pulmonary vein, either from an electrode provided at the tip area of the ultrasonic catheter or on a separate device such as a guidewire through the ultrasonic catheter. Therefore, the procedure may involve ablation at a first energy level in time, then check for the effective conductive block provided by the resulting lesion, and then subsequent ablations and testing until a complete conductive block is formed. In the alternative, the circumferential ablation device may also include feedback control, for example, if thermocouples are provided at the circumferential element formed along the balloon outer surface. Monitoring temperature at this location provides indicia for the progression of the lesion. This feedback feature may be used in addition to or in the alternative to the multi-step procedure described above.

Figure 16A:
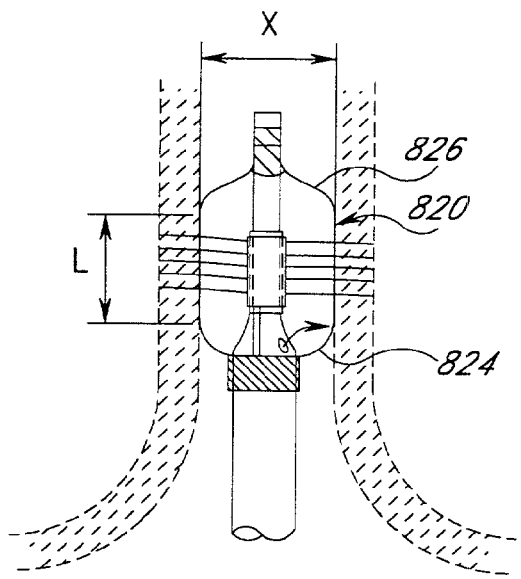
FIG. 16A shows a perspective view of a similar circumferential ablation catheter to the catheter shown in FIG. 15A, and shows the distal end portion of the circumferential ablation catheter during one mode of use in forming a circumferential conduction block at a location where a pulmonary vein extends from an atrium in the region of its ostium along a left atrial wall (shown in cross-section in shadow).
Figure 16B:
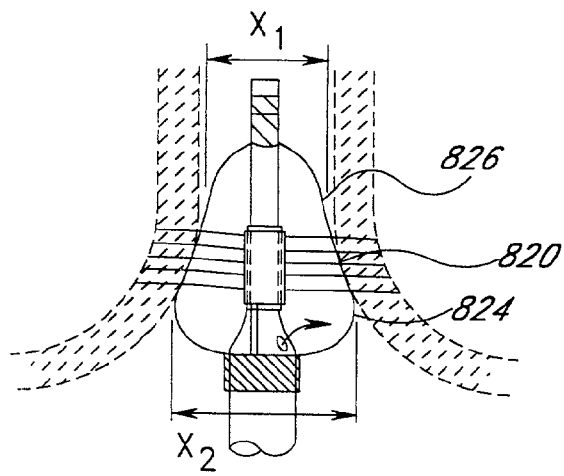
FIG. 16B shows a similar perspective and cross-section shadow view of a circumferential ablation catheter and pulmonary vein ostium as that shown in FIG. 16A, although shows another circumferential ablation catheter wherein the balloon has a tapered outer diameter.
Figure 16C:
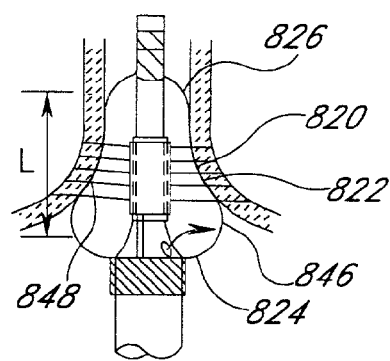
FIG. 16C shows a similar view to that shown in FIGS. 16A–B, although showing another circumferential ablation catheter wherein the balloon has a "pear"-shaped outer diameter with a contoured surface along a taper which is adapted to seat in the ostium of a pulmonary vein.
Figure 16D:
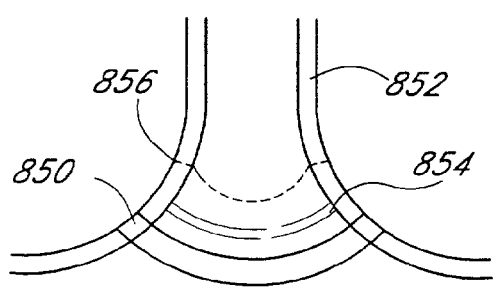
FIG. 16D shows a cross-sectional view of one circumferential conduction block which may be formed by use of a circumferential ablation catheter such as that shown in FIG. 16C.

FIGS. 16A–C show various alternative embodiments of the present invention for the purpose of illustrating the relationship between the ultrasound transducer and balloon of the present invention just described above. More specifically, FIG. 16A shows the balloon 820 having "straight" configuration with a working length D and a relatively constant diameter X between proximal and distal tapers 824, 826. As is shown in FIG. 16A, this variation is believed to be particularly well adapted for use in forming a circumferential conduction block along a circumferential path of tissue which circumscribes and transects a pulmonary vein wall. However, unless the balloon is constructed of a material having a high degree of compliance and conformability, this shape may provide for gaps in contact between the desired circumferential band of tissue and the circumferential band of the balloon skin along the working length of the balloon 820.

The balloon 820 in FIG. 16A is also concentrically positioned relative to the longitudinal axis of the elongate catheter body 802. It is understood, however, that the balloon can be asymmetrically positioned on the elongate catheter body, and that the ablation device can include more than one balloon.

FIG. 16B shows another assembly according to the invention, although this assembly includes a balloon 820 that has a tapered outer diameter from a proximal outer diameter $X_1$ to a smaller distal outer diameter $X_2$. (Like reference numerals have been used in each of these embodiments in order to identify generally common elements between the embodiments.) According to this mode, this tapered shape is believed to conform well to other tapering regions of space, and may also be particularly beneficial for use in engaging and ablating circumferential paths of tissue along a pulmonary vein ostium.

FIG. 16C further shows a similar shape for the balloon as that just illustrated by reference to FIG. 16B, except that the FIG. 16C embodiment further includes a balloon 820 and includes a bulbous proximal end 846. In the illustrated embodiment, the proximate bulbous end 846 of the central region 822 gives the balloon 820 a "pear"-shape. More specifically, a contoured surface 848 is positioned along the tapered working length L and between proximal shoulder 824 and the smaller distal shoulder 826 of balloon 820. As is suggested by view of FIG. 16C, this pear shaped embodiment is believed to be beneficial for forming the circumferential conduction block along a circumferential path of atrial wall tissue that surrounds and perhaps includes the pulmonary vein ostium. For example, the device shown in FIG. 16C is believed to be suited to form a similar lesion to that shown at circumferential lesion 850 in FIG. 16D. Circumferential lesion 850 electrically isolates the respective pulmonary vein 852 from a substantial portion of the left atrial wall. The device shown in FIG. 16C is also believed to be suited to form an elongate lesion which extends along a substantial portion of the pulmonary vein ostium 854, e.g., between the proximal edge of the illustrated lesion 850 and the dashed line 856 which schematically marks a distal edge of such an elongate lesion 850.

As mentioned above, the transducer 830 can be formed of an array of multiple transducer elements that are arranged in series and coaxial. The transducer can also be formed to have a plurality of longitudinal sectors. These modes of the transducer have particular utility in connection with the tapering balloon designs illustrated in FIGS. 32B and 32C. In these cases, because of the differing distances along the length of the transducer between the transducer and the targeted tissue, it is believed that a non-uniform heating depth could occur if the transducer were driven at a constant power. In order to uniformly heat the targeted tissue along the length of the transducer assembly, more power may therefore be required at the proximal end than at the distal end because power falls off as 1/radius from a source (i.e., from the transducer) in water. Moreover, if the transducer 830 is operating in an attenuating fluid, then the desired power level may need to account for the attenuation caused by the fluid. The region of smaller balloon diameter near the distal end thus requires less transducer power output than the region of larger balloon diameter near the proximal end. Further to this premise, in a more specific embodiment transducer elements or sectors, which are individually powered, can be provided and produce a tapering ultrasound power deposition. That is, the proximal transducer element or sector can be driven at a higher power level than the distal transducer element or sector so as to enhance the uniformity of heating when the transducer lies skewed relative to the target site.

The circumferential ablation device 800 can also include additional mechanisms to control the depth of heating. For instance, the elongate catheter body 802 can include an additional lumen that is arranged on the body so as to circulate the inflation fluid through a closed system. A heat exchanger can remove heat from the inflation fluid and the flow rate through the closed system can be controlled to regulate the temperature of the inflation fluid. The cooled inflation fluid within the balloon 820 can thus act as a heat sink to conduct away some of the heat from the targeted tissue and maintain the tissue below a desired temperature (e.g., 90° C.), and thereby increase the depth of heating. That is, by maintaining the temperature of the tissue at the balloon/tissue interface below a desired temperature, more power can be deposited in the tissue for greater penetration. Conversely, the fluid can be allowed to warm. This use of this feature and the temperature of the inflation fluid can be varied from procedure to procedure, as well as during a particular procedure, in order to tailor the degree of ablation to a given application or patient.

The depth of heating can also be controlled by selecting the inflation material to have certain absorption characteristics. For example, by selecting an inflation material with higher absorption than water, less energy will reach the balloon wall, thereby limiting thermal penetration into the tissue. It is believed that the following fluids may be suitable for this application: vegetable oil, silicone oil and the like.

Uniform heating can also be enhanced by rotating the transducer within the balloon. For this purpose, the transducer 830 may be mounted on a torquable member that is movably engaged within a lumen that is formed by the elongate catheter body 802.

Another aspect of the balloon-transducer relationship of the present embodiment is illustrated by reference to FIGS. 17A–B. In general, as to the variations embodied by those figures, the circumferential ultrasound energy signal is modified at the balloon coupling level such that a third order of control is provided for the tissue lesion pattern (the first order of control is the transducer properties affecting signal emission, such as length, width, shape of the transducer crystal; the second order of control for tissue lesion pattern is the balloon shape, per above by reference to FIGS. 16A–C).

This third order of control for the tissue lesion pattern can be understood more particularly with reference to FIG. 17A, which shows balloon 820 to include a shield or filter 860. The filter 860 has a predetermined pattern along the balloon surface adapted to shield tissue from the ultrasound signal, for example, by either absorbing or reflecting the ultrasound signal. In the particular variation shown in FIG. 17A, the filter 860 is patterned so that the energy band which is passed through the balloon wall is substantially more narrow than the band that emits from the transducer 830 internally of the balloon 820. The filter 860 can be constructed, for example, by coating the balloon 820 with an ultrasonically reflective material, such as with a metal, or with an ultrasonically absorbent material, such as with a polyurethane elastomer. Or, the filter can be formed by varying the balloon's wall thickness such that a circumferential band 862, which is narrow in the longitudinal direction as compared to the length of the balloon, is also thinner (in a radial direction) than the surrounding regions, thereby preferentially allowing signals to pass through the band 862. The thicker walls of the balloon 820 on either side of the band 862 inhibit propagation of the ultrasonic energy through the balloon skin at these locations.

Figure 18B:
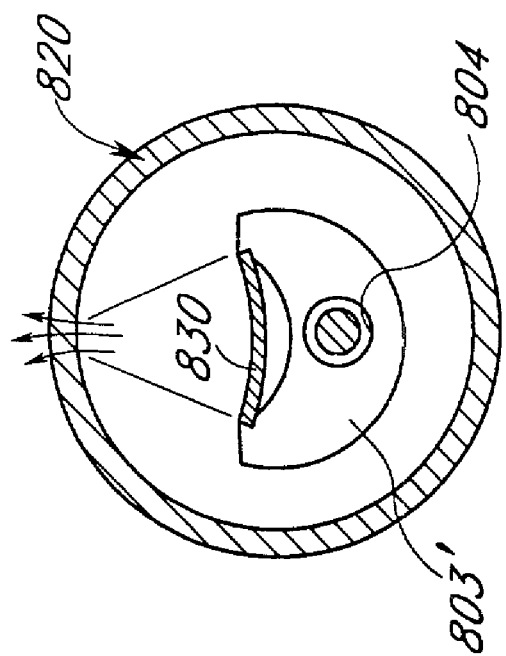
FIG. 18B shows a transverse cross-sectional view of a further circumferential ablation catheter with an ablation element having a single curvilinear section that is mounted so as to position its concave surface facing in a radially outward direction.
Figure 18A:
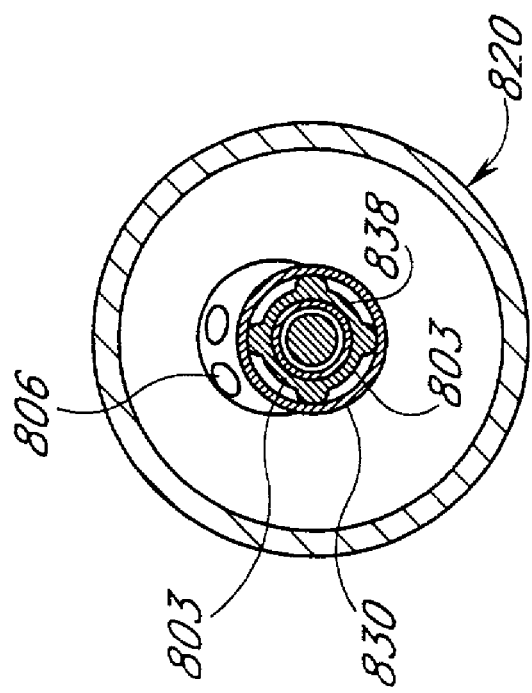
FIG. 18A shows a transverse cross-sectional view of an additional circumferential ablation catheter with an ablation element having a single transducer sector segment which is positioned along an inner member within an expandable balloon which is further shown in a radially expanded condition.

For various reasons, the "narrow pass filter" embodiment of FIG. 18A may be particularly well suited for use in forming circumferential conduction blocks in left atrial wall and pulmonary vein tissues according to the present invention. It is believed that the efficiency of ultrasound transmission from a piezoelectric transducer is limited by the length of the transducer, which limitations are further believed to be a function of the wavelength of the emitted signal. Thus, for some applications a transducer 830 may be required to be longer than the length which is desired for the lesion to be formed. Many procedures intending to form conduction blocks in the left atrium or pulmonary veins, such as, for example, less-invasive "maze"-type procedures, require only enough lesion width to create a functional electrical block and to electrically isolate a tissue region. In addition, limiting the amount of damage formed along an atrial wall, even in a controlled ablation procedure, pervades as a general concern. However, a transducer that is necessary to form that block, or which may be desirable for other reasons, may require a length which is much longer and may create lesions which are much wider than is functionally required for the block. A "narrow pass" filter along the balloon provides one solution to such competing interests.

Figure 17B:
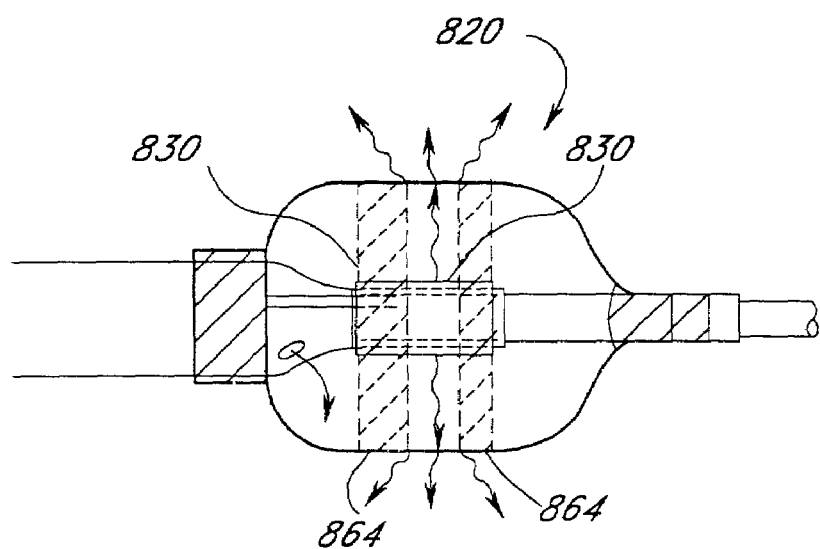
FIG. 17B shows a similar view as that shown in FIG. 17A, although showing the distal end portion of another circumferential ablation catheter which includes a heat sink as an equatorial band within the circumferential path of energy emission from an inner ultrasound transducer.

FIG. 17B shows another variation of the balloon-transducer relationship in an ultrasound ablation assembly according to the present invention. Unlike the variation shown in FIG. 18A, FIG. 17B shows placement of an ultrasonically absorbent band 864 along balloon 820 and directly in the central region of the emitted energy signal from transducer 830. According to this variation, the ultrasonically absorbent band 864 is adapted to heat to a significant temperature rise when sonically coupled to the transducer via the ultrasound signal. It is believed that some ablation methods may benefit from combining ultrasound/thermal conduction modes of ablation in a targeted circumferential band of tissue. In another aspect of this variation, ultrasonically absorbent band 864 may operate as an energy sink as an aid to control the extent of ablation to a less traumatic and invasive level than would be reached by allowing the raw ultrasound energy to couple directly to the tissue. In other words, by heating the absorbent band 864 the signal is diminished to a level that might have a more controlled depth of tissue ablation. Further to this aspect, absorbent band 864 may therefore also have a width that is more commensurate with the length of the transducer, as is shown in an alternative mode in shadow at absorbent band 864.

In each of the embodiments illustrated in FIGS. 15A–17B, the ultrasonic transducer had an annular shape so as to emit ultrasonic energy around the entire circumference of the balloon. The present circumferential ablation device, however, can emit a collimated beam of ultrasonic energy in a specific angular exposure. For instance, as seen in FIG. 18A, the transducer can be configured to have only a single active sector (e.g., 180 degree exposure). The transducer can also have a planar shape. By rotating the elongate catheter body 802, the transducer 830 can be swept through 360 degrees in order to form a circumferential ablation. For this purpose, the transducer 830 may be mounted on a torquable member 803, in the manner described above.

FIG. 18B illustrates another type of ultrasonic transducer that can be mounted to a torquable member 803 within the balloon 820. The transducer 830 is formed by curvilinear section and is mounted on the inner member 803 with its concave surface facing in a radially outward direction. The inner member 803 desirably is formed with recess that substantially matches a portion of the concave surface of the transducer 830. The inner member 803 also includes longitudinal ridges on the edges of the recess that support the transducer above the inner member such that an air gap is formed between the transducer and the inner member. In this manner, the transducer is "air-backed." This spaced is sealed and closed in the manner described above in connection with the embodiment of FIGS. 18A–E.

Deflectable Tip Catheter Assembly

It has been observed that the placement of an ablation catheter at a location where a pulmonary vein extends from an atrial wall raises significant positioning problems, particularly where transeptal access to the atrium and conventional guidewire tracking are employed. The selected pulmonary vein may be located at a very sharp angle from the axis of entry so that placement of a guidewire is very difficult once the guidewire emerges from the transeptal sheath and enters the cardiac chamber. Moreover, even after a guidewire is successfully placed in the selected pulmonary vein, tracking of an ablation catheter over the guidewire is problematic. The ablation catheter resists making the sharp bend toward the pulmonary vein. Furthermore, it has been observed that the guidewire sometimes backs out of the vein under the resistance force from the catheter and may even become completely dislodged from the vein. Therefore, a need exists for an improved ablation catheter design that allows the physician to easily advance an ablation element around the sharp angle from the transeptal sheath into the selected pulmonary vein for creating a circumferential lesion.

Figure 19:
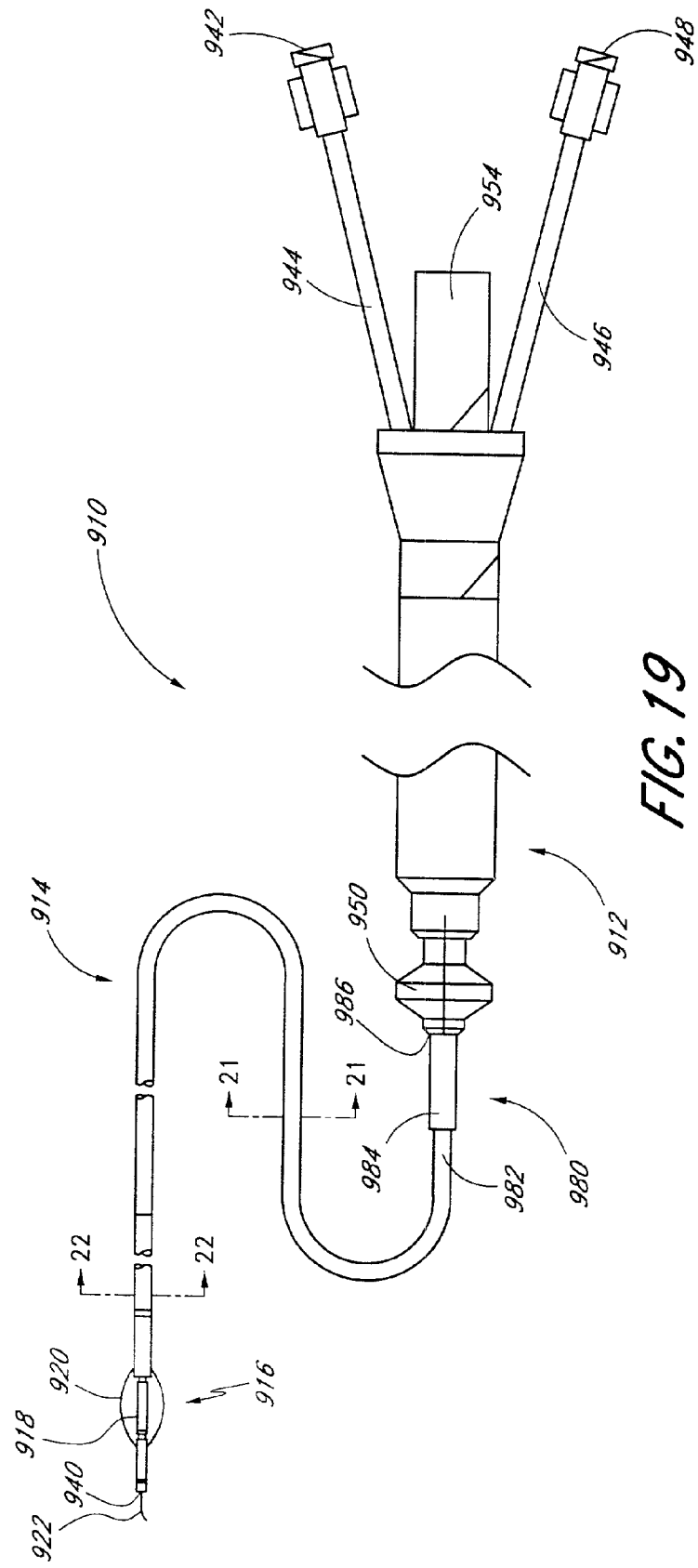
FIG. 19 is an elevational view of a deflectable circumferential ultrasound ablation catheter in accordance with one mode of the present invention.

Referring now to FIG. 19, for purposes of illustration, the present invention is embodied in a deflectable tip catheter 910 in accordance with one mode of the present invention. The deflectable tip catheter 910 includes, generally, a handle portion 912, an elongated catheter body 914 and a deflectable tip portion 916. An ablation element 918 is disposed on the deflectable tip portion 916. The ablation element 918 is surrounded by an expandable member 920 used for anchoring the catheter at a selected anatomic site, such as in the ostium of a pulmonary vein.

The deflectable tip catheter 910 is adapted to track over a guidewire 922. The guidewire 922 is slidably disposed in a guidewire lumen (not shown) that extends from a proximal port 942 located at the proximal end of a guidewire lumen extension tube 944 on the handle 912 to a distal port 940 in the deflectable tip portion 916. Preferably, the deflectable tip catheter of the present invention can be used with a wide variety of commercially available cardiology guidewires.

In a variation to the illustrated guidewire lumen, which extends the entire longitudinal length of the catheter, the guidewire lumen may extend from the distal port 940 to a proximal port located distal to the handle. Indeed, monorail or rapid-exchange guidewire tracking mechanisms may be positioned anywhere along the deflectable tip portion.

The handle 912 comprises a mechanism that controls the deflection of the deflectable tip portion 916. The handle 912 operates by placing tension on a pull wire (not shown) that is attached to the deflectable tip portion 916. The thumb slide 950 on the handle 912 is coupled to the proximal end 986 of the elongated catheter body 914. When the thumb slide 950 is moved distally, the elongated catheter body 914 is pushed distally relative to the pull wire thereby creating tension in the pull wire and causing the deflectable tip portion 916 to bend. The deflectable tip can be used to steer the catheter as it is advanced through the patient's vasculature or, alternatively, to direct the advancement of the guidewire from the catheter toward a selected anatomic site.

Figure 20:
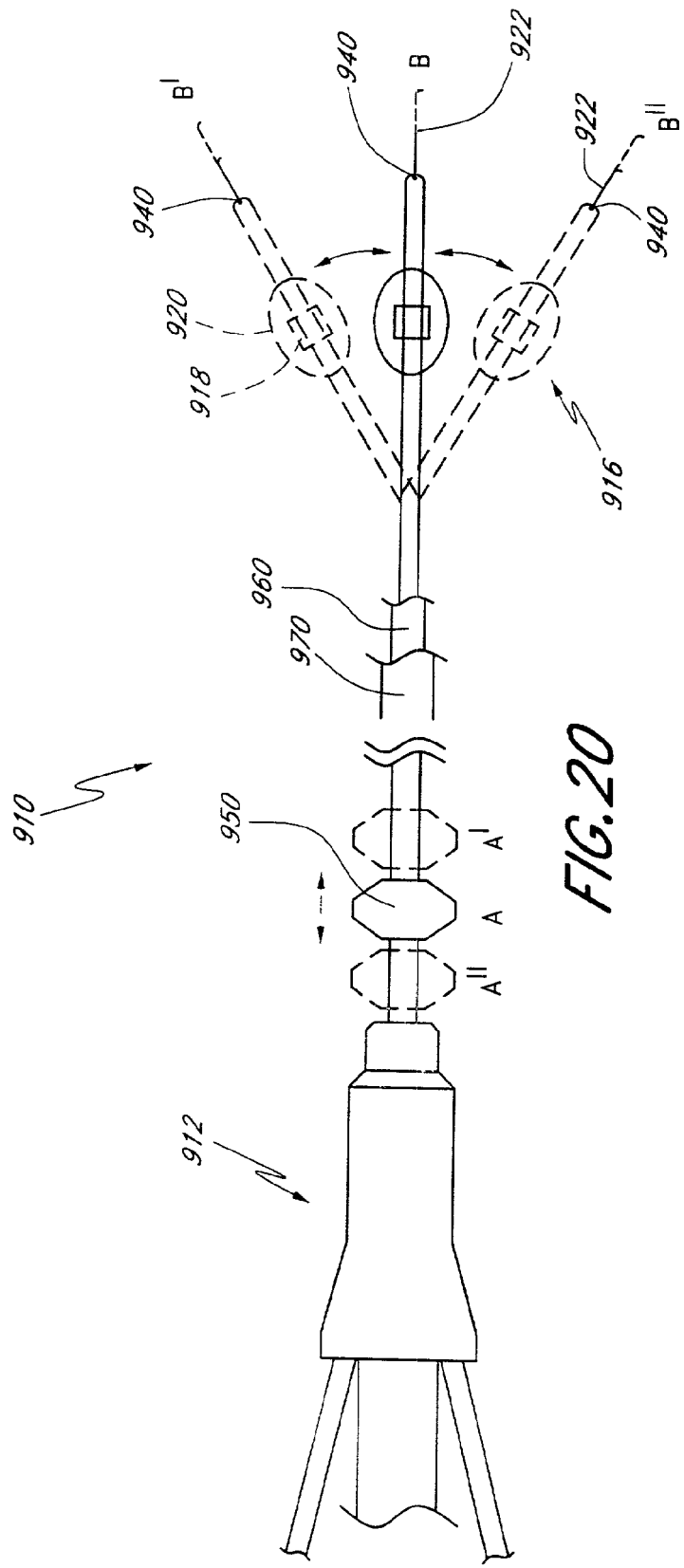
FIG. 20 is a side view of a deflectable tip catheter of FIG. 19 showing the distal end portion in various deflected positions.

FIG. 20 illustrates the movement of the deflectable tip portion 916 of the deflectable tip catheter 910 according to one embodiment of the present invention. When the thumbslide 950 on the handle 912 is moved distally from position A to position A' (drawn in phantom), the distal end portion 916 of the elongated body 14 is deflected from position B (zero deflection) to position B'. Furthermore, in some embodiments of the handle portion 912, when the thumbslide 950 on the handle 912 is moved from position A to position A" (drawn in phantom), the distal end portion 916 of the elongated catheter body 914 is deflected from position B (zero deflection) to position B". Still referring to FIG. 20, for purposes of illustration, the deflectable tip catheter 910 is shown slidably engaged in a left atrial guide catheter 960, such as for example, a transeptal sheath, which is also slidably engaged in an introducer sheath 970. The guidewire 922 is illustrated as emerging from the distal port 940 in the deflectable tip portion 916.

In the preferred embodiment of the deflectable tip catheter 910 shown in FIG. 19, the handle 912 is a modified version of the BIOSENSE handle that is commercially available from Johnson & Johnson. The back end of the handle originally comes with only one through hole of about 0.095". This hole was opened to 0.110" and a second through hole was made to about 0.130". These holes were used to extend the guidewire and inflation lumens all the way out of the handle (see extension tubes 944 and 946). A 0.042"/0.035" hypotube (4 cm long) was fused at the proximal end of the multilumen elongated catheter body 914, then a PVC extension was attached to the hypotube (PVC extension being about 914 cm long, 0.045"/0.125"). A 0.047"/0.057" polyimide tubing was fused at the proximal end of the elongated body. A 0.026"/0.013" Teflon tube was loaded into the pull wire lumen and advanced all the way from the proximal end portion to the distal tip. A PTFE-coated mandrel (0.008") was loaded into the Teflon tube and anchored at the distal end. The inside diameter of the BIOSENSE handle was also modified. It originally had two round through holes, one of about 0.115" and a second of about 0.075". Both holes were enlarged and connected together to form a single hole. This large hole was used to extend electrical and fluid lumens to proximal connections.

In an alternative embodiment of the deflectable tip catheter 910, a new generation BIOSENSE handle may be used. Using the new generation handle, single or two direction deflection is possible and the handle is designed such that the pull wire is moved rather than the catheter shaft.

Figure 21:
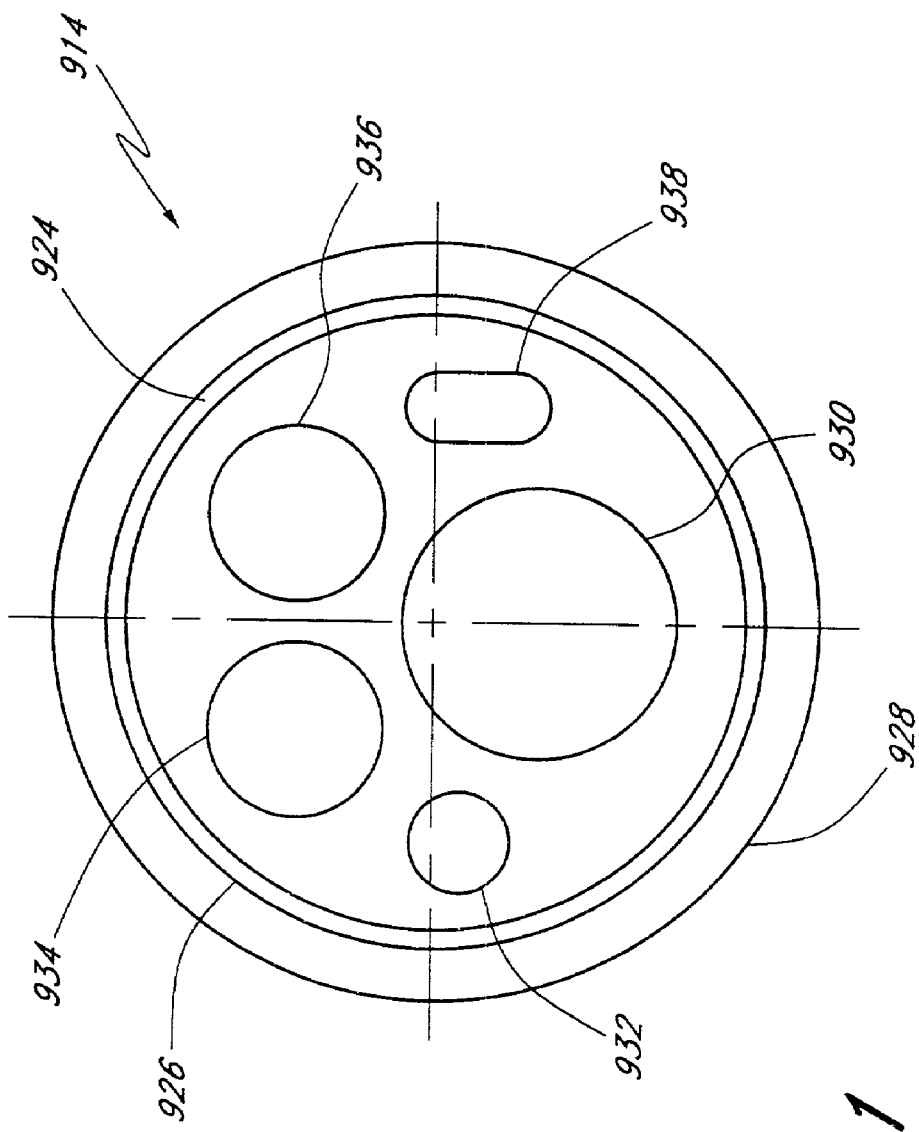
FIG. 21 is a cross-sectional view taken along line 21—21 of the deflectable circumferential ultrasound ablation catheter shown in FIG. 19.

With reference to FIG. 21, there is shown a cross-sectional view of the elongated catheter body 914 taken along line 21—21 of the deflectable tip catheter 910 shown in FIG. 19. As illustrated, the elongated catheter body 914 preferably comprises, generally, an inner catheter 924, an intermediate layer preferably comprising a stainless steel braid 926, and an outer extrusion 928. Within the elongated catheter body 914 may be disposed several lumens, including for example, a guidewire lumen 930, a pull wire lumen 932, an inflation lumen 934, a coaxial cable lumen 936, and a thermocouple leads lumen 938. In addition to providing the requisite lumens, the elongated catheter body 914 is also adapted to be introduced into the left atrium such that the distal tip portion 916 can be placed within the pulmonary vein ostium in a transeptal procedure.

Referring now to FIGS. 19 and 21, the guidewire lumen 930 in the deflectable tip catheter 910 extends from a proximal port 942 in the guidewire lumen extension tube 944 to the distal port 940 in the deflectable tip portion 916. The guidewire lumen 930 preferably is adapted to slideably receive guidewires ranging from about 0.010 inch to about 0.038 inch in diameter, and preferably is adapted for use with guidewires ranging from about 0.018 inch to about 0.035 inch in diameter. Where a 0.035 inch guidewire is to be used, the guidewire lumen 930 preferably has an inner diameter of about 0.040 inch to about 0.052 inch.

The pull wire lumen 932 extends longitudinally through the elongated catheter body 914 and is formed to slidably receive the pull wire that extends from the handle 912 to the deflectable tip portion 916. The pull wire is adapted to deflect the deflectable tip portion by applying tension along the varied stiffness transitions along the catheter's length. Acceptable pull wires may have a diameter within the range from about 0.008 inch to about 0.020 inch, and may further include a taper, such as, for example, a tapered outer diameter from about 0.020 inch to about 0.008 inch.

The inflation lumen 34 in the elongated catheter body 914 operably couples a pressurizable fluid source (not shown) to the expandable member 920. The inflation lumen 934 extends longitudinally through the elongated catheter body 914 from the expandable member 920 to a proximal port 948 at the proximal end of the inflation lumen extension tube 946. By introducing fluid into the proximal port 948, a physician can inflate and deflate the expandable member 920, as known in the art. The inflation lumen 934 preferably has an inner diameter of about 0.020 inch in order to allow for rapid deflation times, although this may vary based upon the viscosity of inflation medium used, length of the lumen, and other dynamic factors relating to fluid flow and pressure.

The elongated catheter body 914 may also include a thermocouple leads lumen 938 for providing temperature feedback. The expandable member 920 can include one or more thermal sensors that are provided on either the outside or the inside of the expandable member 920. Monitoring temperature at this location provides indicia for the progression of the ablation procedure. If the temperature sensors are located inside the expandable member 920, the feedback control may also need to account for any temperature gradient that occurs through the wall of the expandable member. The thermocouple leads extend from the thermal sensor through the thermocouple leads lumen 938 in the elongated catheter body 914 to the proximal end of the device where the signal can be monitored using suitable external equipment.

Still referring to FIGS. 19 and 21, the outer extrusion 928 of the elongated catheter body 914 comprises a thin-walled, resilient tubing. The outer extrusion 928 may be formed of any of the biocompatible resilient plastics typically used in catheters, with polyimide and polyurethane available under the tradename PEBAX (from Atochem of Glen Rock, N.J.) being preferred materials.

Disposed within the outer extrusion 928, and radially outside of the inner catheter 924 is an intermediate layer 926 adapted to provide the catheter with good flexibility while maintaining high fidelity torque transmission along the elongated catheter body 920. A preferred material for the intermediate layer 926 is a metal braid formed of interleaved lengths of stainless steel. The stainless steel braid 926 is coated with a polyurethane (such as PEBAX) to form the outer extrusion 928. The outer extrusion 928 bonds to the inner catheter 924 to form a unitary catheter structure. The elongated catheter body 914 preferably has a length in the range from about 100 cm to about 140 cm.

The elongated catheter body 914 is constructed to be at least 30% stiffer than the deflectable tip portion 916. According to this relationship, the elongated catheter body 914 may be suitably adapted to provide push transmission to the deflectable tip portion 916 while the deflectable tip portion 916 is suitably adapted to track through bending anatomy during in vivo delivery of the deflectable tip portion 916 of the device into the desired ablation region. When constructed for use in transeptal left atrial ablation procedures, the elongated catheter body 914 desirably has an outer diameter provided within the range from about 5 French to about 15 French, and more preferably from about 7 French to about 12 French.

Figure 22:
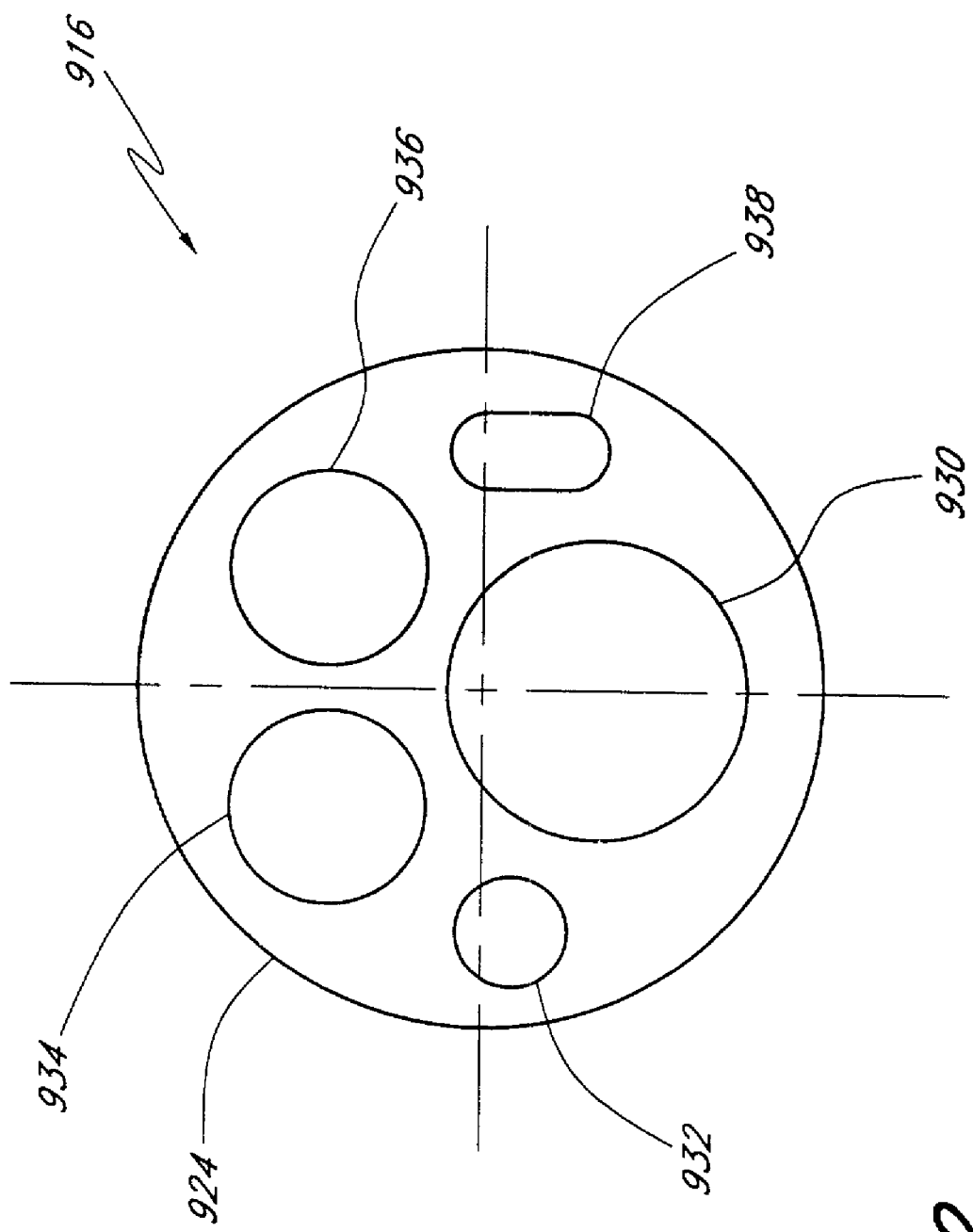
FIG. 22 is a cross-sectional view taken along line 22—22 of the deflectable circumferential ultrasound ablation catheter shown in FIG. 19.

Referring now to FIG. 22, there is shown a cross-sectional view of the deflectable tip portion 916 taken along line 22—22 of the deflectable tip catheter 910 shown in FIG. 19. The same lumens are present within the deflectable tip portion 916 as detailed above with respect to the cross-sectional view of the elongated catheter body 914. However, the intermediate, torque-transmitting braid (926 in FIG. 21) is not present within the outer extrusion (928 in FIG. 21). Moreover, the outer extrusion itself is thinner, to facilitate flexibility of the distal end region. Thus, for illustration purposes, because of the relative thinness of the catheter wall 929 in the distal region, the wall (inner and outer surfaces) is labeled using a single reference numeral 929.

Figure 23:
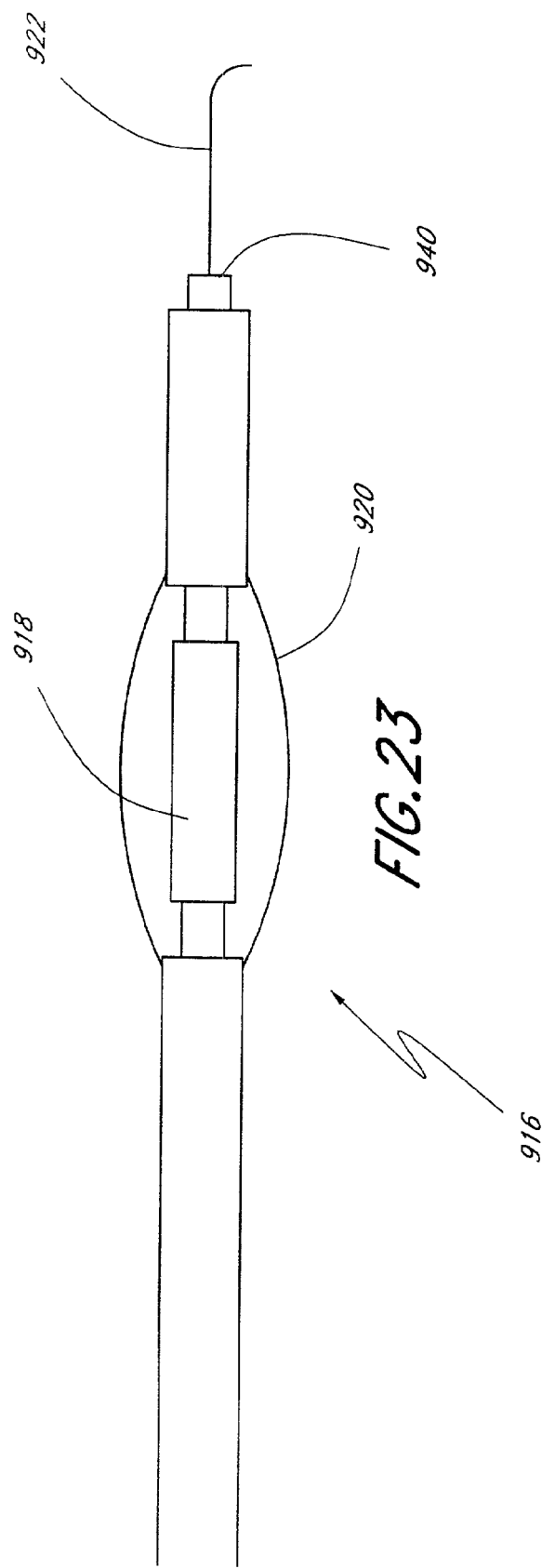
FIG. 23 illustrates the distal portion of the circumferential ultrasound ablation catheter.

Referring now to FIG. 23, the expandable member 920 disposed on the deflectable tip portion 916 preferably comprises an inflatable balloon having a diameter in a collapsed state roughly the same as that of the elongated catheter body 914. The balloon can be expanded to a diameter generally matching the diameter of the circumferential region of tissue, preferably from about 2 cm to about 3 cm, and may be expandable to a plurality of expanded positions in order to work with pulmonary vein ostia and/or pulmonary veins of various sizes. Although the expandable member described above is an inflatable balloon, it will be understood that the ablation catheter can also include other types of expandable members, such as, for example baskets, cages and like expandable structures without departing from the scope of the invention.

The ablation element 918 is disposed on the deflectable tip portion 916 and cooperates with the expandable member 920 such that the ablation element 918 is held in a generally fixed position relative to the target circumferential region of tissue. In the preferred embodiment, the ablation element 918 is an ultrasound transducer adapted to emit ultrasonic sound waves sufficient to ablate a circumferential region of tissue when coupled to a suitable excitation source. The ablation element can be located outside or inside the expandable member, or can be located at least partially outside the expandable member. The ablation element, in some forms, also includes a portion of the expandable member. For example, as illustrated in FIG. 23, the deflectable tip catheter assembly includes an ultrasonic transducer located within the expandable member 920. In one preferred embodiment, the ultrasonic transducer excites a portion of the expandable member 920 during ablation and the heat in the expandable member is transferred to the surrounding tissue.

Energy from the ablation control system is typically delivered to the ablation element via electrical conductor leads. The ablation control system includes a current source for supplying current to the ablation element, a monitoring circuit, and a control circuit. The current source is coupled to the ablation element via a lead set (and to a ground patch in some modes). The monitor circuit desirably communicates with one or more sensors (e.g., temperature and/or current sensors) which monitor the operation of the ablation element. The control circuit is connected to the monitoring circuit and to the current source in order to adjust the output level of the current driving the ablation element based upon the sensed condition (e.g., upon the relationship between the monitored temperature and a predetermined temperature set point).

The deflectable tip catheter also desirably includes temperature feedback for monitoring the progression of the lesion. For instance, the expandable member can include one or more thermal sensors (e.g., thermocouples, thermistors, etc.) that are provided to either the outer side or the inside of the expandable member. If the temperature sensors are located inside the expandable member, the feedback control may also need to account for any temperature gradient that occurs through the wall of the expandable member. If the sensors are placed on the exterior of the expandable member, they may also be used to record electrogram signals by reconnecting the signal leads to different input port of a signal-processing unit. Such signals can be useful in mapping the target tissue both before and after ablation.

The thermocouples and/or electrodes desirably are blended into the expandable member in order to present a smooth profile. Transition regions, which are formed by either adhesive or melted polymer tubing, "smooth out" the surface of the expandable member as the surface steps up from the outer surface of the expandable member to the thermocouple surface. Various constructions to integrate the thermocouples and/or electrodes into the expandable member, as well as various approaches to using thermocouples and electrodes with an expandable member, are described in detail below.

In some modes of the present deflectable tip catheter, a position monitoring system may also be employed to facilitate positioning of the ablation member. The position monitoring system includes a sensor control system and a display. The sensor control system communicates with one or more sensor elements located in, or near the expandable member. In one variation, the ablation element and sensor element are combined in a single element that provides both sensing and ablation capabilities. In other variations, separate elements are used for the ablation element and the sensor element(s).

An ultrasonic position monitoring system uses a single, circumferentially symmetric ultrasonic transducer. The sensor can be the ultrasonic ablation element, or a separate ultrasonic transducer in addition to an ultrasonic ablation element. The transducer is positioned in a pulmonary vein, and the transducer is operably connected to a sensor control system. In one device, the sensor control system is a Panametrics Model 5073PR. The sensor control system includes a transmitter, a receiver, and a diplexer. An output from the transmitter is provided to a transmitter port (port 1) of the diplexer. An output from a receiver port (port 3) of the diplexer is provided to an input of the receiver. A transducer port (port 2) of the diplexer is provided through a connector to the transducer. An output from the receiver is provided to the display.

A diplexer is commonly used in radar and sonar systems to isolate the transmitter output from the receiver input. Energy provided to the transmitter port of the diplexer (port 1) is provided to the transducer port (port 2) of the diplexer, but not to the receiver port of the diplexer (port 3). Energy provided from the transducer to the transducer port of the diplexer (port 2) is provided to the receiver port (port 3) of the diplexer, but not to the transmitter port (port 3) of the diplexer.

The diplexer can be a circulator or an electronically controlled switch controlled by a timing generator. The timing generator sets the switch to connect the transmitter to the transducer for a first time period. The timing generator then sets the switch to connect the receiver to the transducer for a second time period. By switching the transducer between the transmitter and the receiver, the diplexer effectively "timeshares" the transducer between the transmitter and the receiver.

The transmitter generates a signal that drives the transducer. When the diplexer connects the transmitter to the transducer, the drive signal from the transmitter causes the transducer to emit an ultrasonic sound wave. The ultrasonic sound wave propagates through the interior of the expandable member, through the wall of the expandable member, and reflects off of the inner wall of the ostium. The reflected ultrasonic energy returns to the transducer and causes the transducer to generate an echo signal. The echo signal is provided through the diplexer to the receiver. The receiver amplifies and processes the echo signal to produce a display signal. The display signal is provided to the display.

The transducer transmits a radiated wave. For a cylindrically symmetric transducer, the radiated wave will approximate a cylindrical wave that expands away from the transducer. When the cylindrical wave reaches the ostium, the wave will be reflected in a substantially cylindrically symmetric fashion to produce a reflected wave that is similar to a cylindrical wave as well. The reflected wave propagates back to the transducer.

Reflections will occur when the ultrasonic sound wave propagating in a medium strikes a transition (or interface) in the acoustic properties of the medium. Any interface between materials having different acoustic properties will cause a portion of the wave to be reflected.

The transmit pulse causes the transducer to vibrate (in a manner very similar to a bell) during the ring-down period thereby producing the ring-down signal. The echo pulse is caused by ultrasonic energy that is reflected from the ostium back to the transducer. During the ring-down period it is difficult to see signals caused by reflections (such as the signal) because the signals produced by reflections are typically relatively small in amplitude and are easily masked by the relatively large amplitude portions of the ring-down signal. Thus, it is difficult to detect reflections from targets that are so close to the transducer that their reflections return during the ring-down period. This can limit the minimum useful range of the transducer.

The ring-down time of the transducer can be reduced by configuring the transmitter to provide a shaped transmit pulse. The shaped transmit pulse drives the transducer in a manner that reduces the amplitude of the ringing and shortens the ring-down period. Since the ring-down period is shorter, the shaped transmit pulse allows the transducer to be used to detect targets at a shorter distance.

In a device where the transducer is also used as the ablation element, the transmitter provides two power modes, a low-power mode used for position measurements, and a high-power mode used for ablation. When ablation is desired, the diplexer stops switching between the receiver and the transmitter, and stays locked on the transmitter while the transmitter operates in the high-power mode.

Ultrasonic ablation requires that the transducer produce an ultrasonic wave having relatively higher power. Higher power typically requires a transducer having a relatively large physical size. Larger transducers often have longer ring-down times. While the use of a shaped transmit pulse will reduce ring-down times, for some transducers even the use of a shaped transmit pulse does not shorten the ring-down time sufficiently to allow the ablation element to be used for position sensing. Moreover, in some devices, the ablation element is not an ultrasonic transducer, and thus may be unsuitable for use as a position sensor. Thus, in some devices, it is desirable to add one or more ultrasonic transducers to be used for position sensing.

Construction of Deflectable Tip Catheter Assembly

Referring again to FIG. 19, to facilitate actuation of the deflectable tip, the deflectable tip catheter 910 is preferably constructed to the following specifications. In a first deflectable tip catheter design, the elongated catheter body 914 has an outer diameter of 8 French, with an outer extrusion comprising 63D PEBAX. The deflectable tip portion 916 (approximately 3 cm) has an outer diameter of 8 French, with an outer extrusion comprising 40D PEBAX. The elongated catheter body 914 has at least five lumens (guidewire, inflation, pull wire, coaxial power cable, and sensor leads) as detailed above, wherein each of the wires, lumens or leads uses one of the five lumens described with reference to FIG. 22. The thumb slide 950 of the handle 912 moves the elongated catheter body 914 over the deflecting pull wire to achieve single direction deflection. Distal movement of the thumb slide 950 pushes the shaft over the pull wire to deflect the deflectable tip portion 916. The guidewire, balloon inflation/deflation, power cable and thermocouple lumens are routed through the handle in a way that allows the lumens to slide independent of the handle's proximal end.

In a second alternative design, the elongated catheter body 914 has an outer diameter of 10 French, with an outer extrusion comprising 63D PEBAX. The distal end portion 916 (approximately 3 cm) has an outer diameter of 10 French, with an outer extrusion comprising 40D PEBAX. Individual lumens for the guidewire and balloon inflation are created using separate polyimide or Teflon tubes which run through the entire length of the catheter shaft and are heat bonded into the distal deflectable tip. The thumb slide 950 of the handle portion 912 pushes the elongated catheter body 914 over the deflecting pull wire to achieve single direction deflection. Due to the elongated catheter body pushing over the pull wire to deflect the distal tip, all internal wires and lumens must be free of the elongated catheter body and fixed within the non-motion part of the handle and at the distal end of the catheter.

In a third alternative design, the elongated body 914 has an outer diameter of 9+ French, with an outer extrusion comprising 55D PEBAX. The distal end portion 916 (approximately 3 cm) has an outer diameter of 9+ French, with an outer extrusion comprising 40D PEBAX. The elongated catheter body 914 has five lumens (guidewire, inflation, pull wire, coaxial power cable, and sensor leads) as detailed above, wherein each of the wires, lumens or leads uses one of the five lumens described with reference to FIG. 22. The thumb slide 950 of the handle portion 912 pushes the shaft over the deflecting pull wire to achieve single direction deflection. Due to the elongated catheter body 914 pushing over the pull wire to deflect the distal tip, the guidewire, balloon inflation/deflation, power cable and thermocouple lumens must be routed through the handle in a way that allows the lumens to slide independent of the handle's proximal end. A mixture of tubing materials (as described above) are used to extend the lumen paths through the handle.

In a fourth alternative design, the elongated body 914 has an outer diameter of 10–12 French, with an outer extrusion comprising 55D PEBAX. The distal end portion 916 (approximately 3 cm) has an outer diameter of 10–12 French, with an outer extrusion comprising 40D PEBAX. The elongated catheter body 914 has five lumens (guidewire, inflation, pull wire, coaxial power cable, and sensor leads) as detailed above. The deflecting pull wire(s) move to achieve one or two directions of deflection. This design yields a stiffer catheter shaft. Due to the pull wires moving within the elongated catheter body to steer the distal tip, this design affords a better chance that the deflectable tip portion 916 will return to a straight (zero) position.

The inflatable balloon may be constructed from a variety of known materials, although the balloon preferably is adapted to conform to the contour of a pulmonary vein ostium and/or pulmonary vein wall. For this purpose, the balloon material can be of the highly compliant variety, such that the material elongates upon application of pressure and takes on the shape of the body lumen or space when fully inflated. Suitable balloon materials include elastomers, such as, for example, but without limitation, silicone, latex, or low durometer polyurethane (for example a durometer of about 80 A).

In addition, or in the alternative to constructing the inflatable balloon of highly compliant material, the inflatable balloon can be formed to have a predefined fully inflated shape (i.e., be preshaped). The balloon is shaped to generally match the anatomic shape of the body lumen in which the inflatable balloon is inflated. For instance, the inflatable balloon can have a distally tapering shape to generally match the shape of a pulmonary vein ostium, and/or can include a bulbous proximal end to generally match a transition region of the atrium posterior wall adjacent to the pulmonary vein ostium. In this manner, the desired seating within the irregular geometry of a pulmonary vein or vein ostium can be achieved with both compliant and non-compliant balloon variations.

Another variation of the deflectable tip catheter may employ a removable handle. The deflectable catheter consists of a tubular member made from a wire wound coil surrounding a moveable pull wire. The distal end of the pull wire is attached internally to the distal end of the tubular member. The proximal end of the pull wire, which extends beyond an externally threaded proximal end of the tubular member, has a enlarged stop or ball that is engaged within a recess in the shaft of a pull knob. The shaft of the pull knob is slideably engaged within a bore in the proximal region of a handle. The distal region of the handle is tapered and includes an internally threaded hole adapted to receive the externally threaded proximal end of the tubular member. Pulling on the pull knob causes the tubular member to deflect.

In the preferred embodiment of the deflectable tip catheter 910 shown in FIG. 19, the handle 912 is a modified version of the BIOSENSE handle that is commercially available from Johnson & Johnson. The back end of the handle originally comes with only one through hole of about 0.095". This hole was opened to 0.110" and a second through hole was made to about 0.130". These holes were used to extend the guidewire and inflation lumens all the way out of the handle (see extension tubes 944 and 946). A 0.042"/0.035" hypotube (4 cm long) was fused at the proximal end of the multilumen elongated catheter body 914, then a PVC extension was attached to the hypotube (PVC extension being about 14 cm long, 0.045"/0.125"). A 0.047"/0.057" polyimide tubing was fused at the proximal end of the elongated body. A 0.026"/0.013" Teflon tube was loaded into the pull wire lumen and advanced all the way from the proximal end portion to the distal tip. A PTFE-coated mandrel (0.008") was loaded into the Teflon tube and anchored at the distal end. The inside diameter of the BIOSENSE handle was also modified. It originally had two round through holes, one of about 0.115" and a second of about 0.075". Both holes were enlarged and connected together to form a single hole. This large hole was used to extend electrical and fluid lumens to proximal connections.

Figure 24:
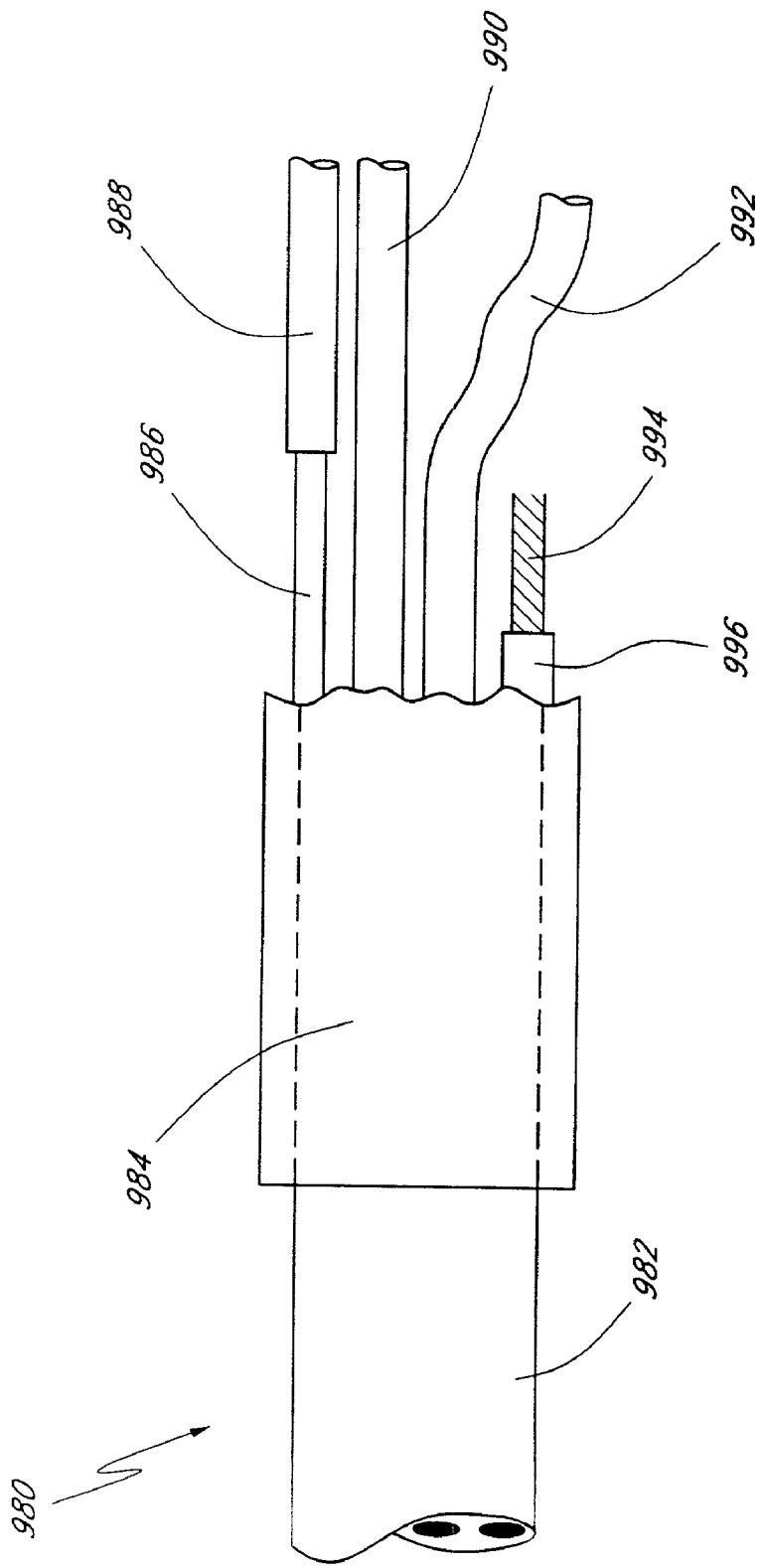
FIG. 24 is a partially cut away view of the proximal end of the present invention.

With reference to FIG. 24, there is illustrated an expanded schematic view of one preferred modification of the proximal end 980 of the elongated catheter body 914. It is understood, however, that any other extensions and modifications within the skill of those in the art are encompassed within the scope of the present disclosure. Here, surrounding the proximal end portion is a shrink-wrap layer 984, formed from ⅛ inch plastic shrink-wrap, such as for example PET. An extension of the guidewire lumen is formed using a plastic tubing 986, such as for instance 0.057"/0.048" polyimide tubing that extends about 16.5 cm beyond the proximal end portion 982. A single lumen polyimide/PEBAX sleeve 988 may surround the extension. The inflation lumen is also extended about 16.5 cm using a hypotube 990, preferably of 0.042"/0.035". The coaxial cable 992 extends about 16 cm proximally from the proximal end portion 982. A 0.008" PTFE-coated mandrel was used for the deflecting pull wire 994, which is shown slidably engaged in a 0.026"/0.013" Teflon tube 996. The Teflon tubing 996 extends only about 1 cm past the proximal end portion and the pull wire 994 extends about 4 cm beyond the proximal end portion, where it connects to the handle (not shown).

Notwithstanding the specific device constructions just described, other embodiments of the are also contemplated. For example, while the figures illustrate an "over-the-wire" catheter construction, other guidewire tracking designs are suitable substitutes, such as, for example, catheter devices which are known as "rapid exchange" or "monorail" variations, wherein the guidewire is only housed coaxially within a lumen of the catheter in the distal region of the catheter.

Method of Operation

With reference to FIGS. 25–28, the operation of the deflectable tip catheter of the present invention will now be addressed. The flow diagram in FIG. 25 broadly illustrates in diagrammatical form a method of using a deflectable tip catheter to access a pulmonary vein and form a circumferential lesion.

Figure 25:
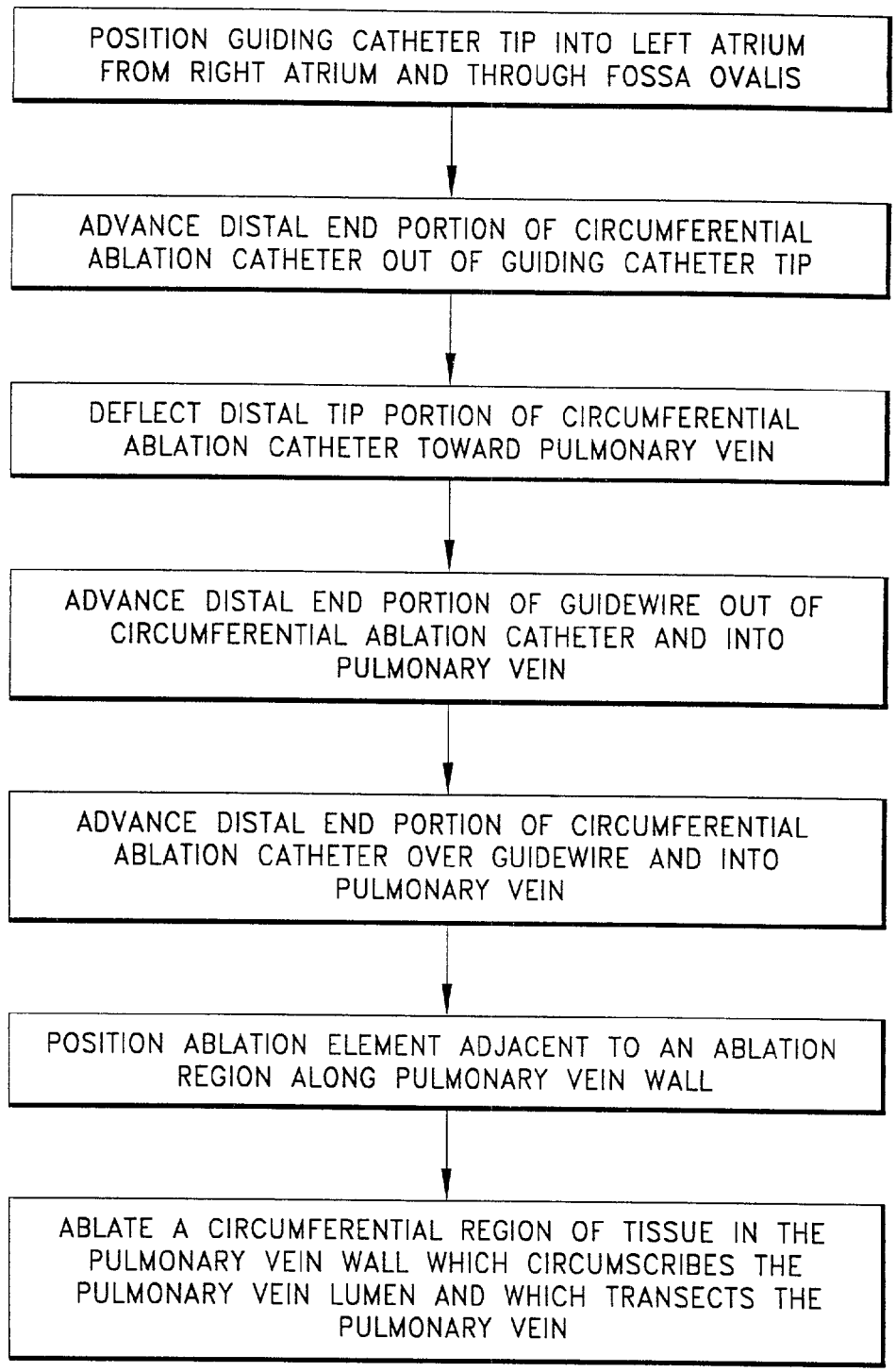
FIG. 25 diagramatically shows sequential, general steps of a method for treating atrial arrythmia using the deflectable tip catheter of the present invention.
Figure 26:
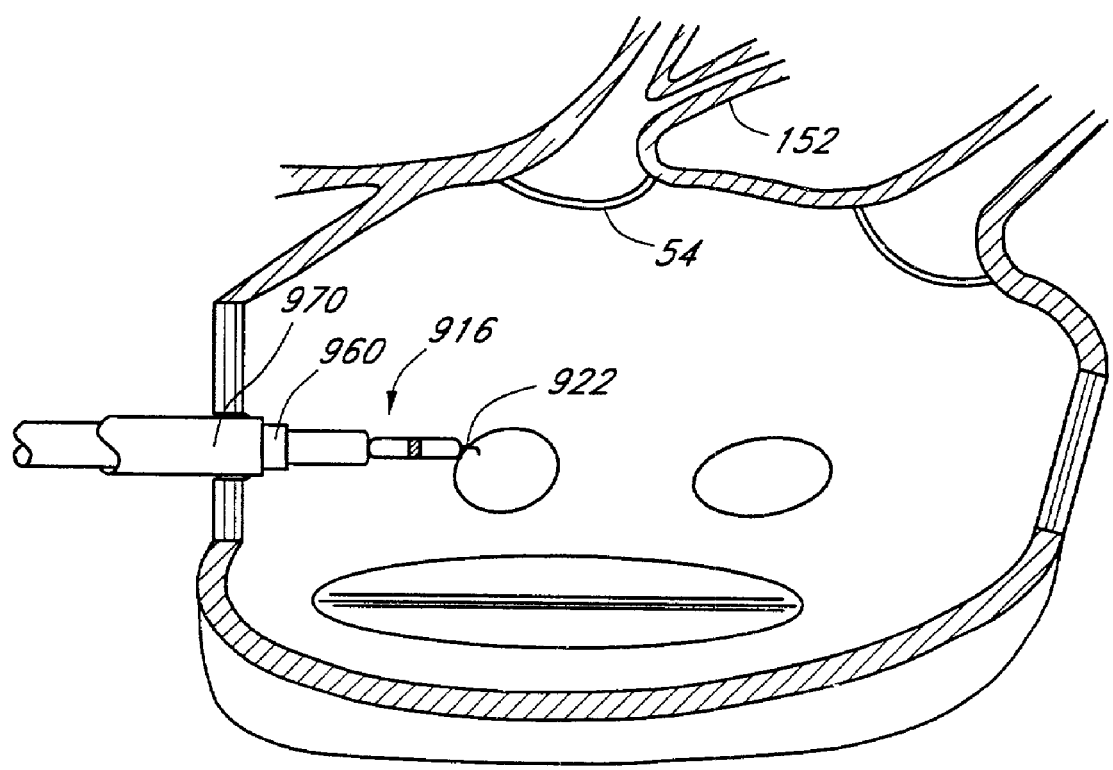
FIG. 26 is a perspective view showing the deflectable tip catheter of FIG. 19 being advanced into the left atrium.
Figure 27:
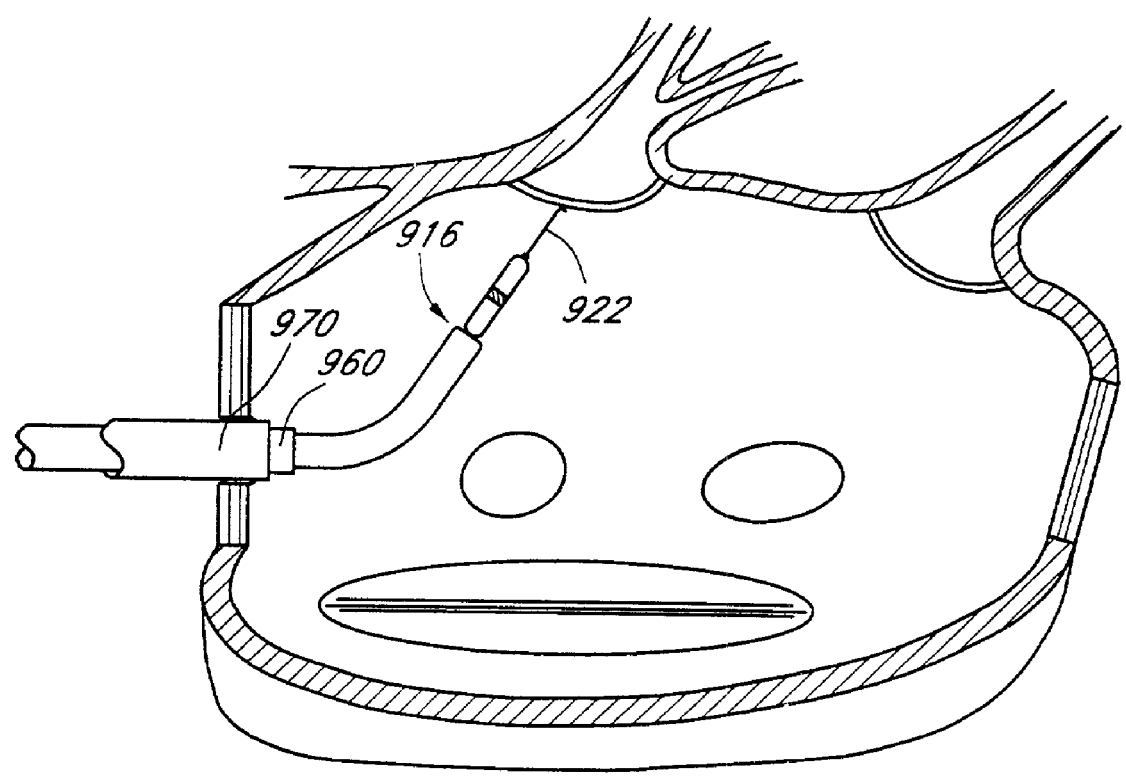
FIG. 27 is a perspective view showing the deflectable tip catheter of FIG. 19 whereby the deflectable tip portion is deflected to direct the guidewire toward the desired pulmonary vein.

According to the method described in FIG. 25, a physician advances the ablation catheter assembly into the left atrium, as illustrated in FIG. 26, by manipulating the handle and actuating the thumb-slide to steer the deflectable tip. The deflectable tip catheter is preferably advanced through a guiding catheterer 960 which is coaxial within a transeptal sheath 970 seated in the fossa ovalis. Once the deflectable tip portion 916 is inside the left atrium, the thumb-slide on the handle is actuated to deflect the deflectable tip portion toward the selected pulmonary vein as illustrated in FIG. 27. The physician then distally advances the guidewire 922 through the deflectable tip catheter. The guidewire 922 is advanced from the distal port 940 in the deflectable tip portion 916 and, due to the deflection, is directed into the selected pulmonary vein to a suitable anchoring position.

Figure 28:
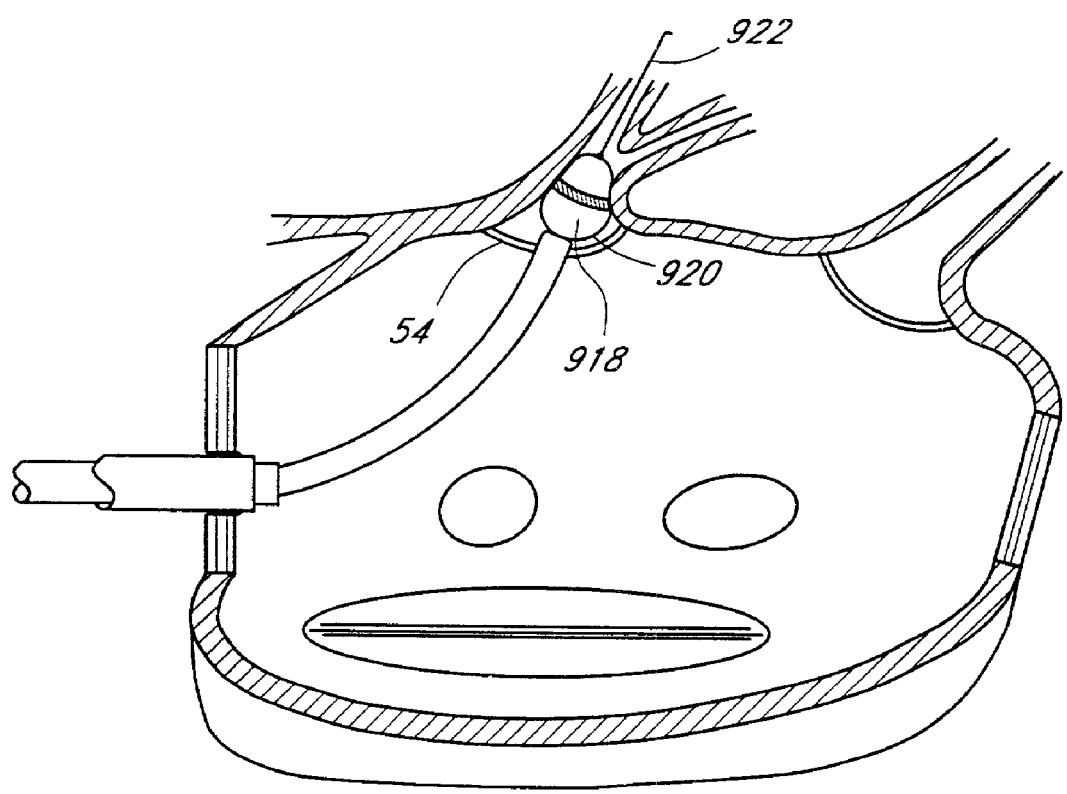
FIG. 28 is a perspective view of a circumferential ablation device assembly during use in a left atrium subsequent to performing transeptal access and guidewire advancement steps according to the method of FIG. 25.

Once the distal end of the guidewire 922 is positioned in the pulmonary vein, the deflectable tip catheter is advanced over the guidewire 922 until the expandable member 920 is positioned at the selected pulmonary vein ostium 54. As the catheter is advanced over the guidewire 922, the deflectable tip portion 916 may be deflected to reduce the resistance between the catheter and the guidewire. Once the expandable member 920 is positioned at the desired location relative to the targeted region of circumferential tissue, the guidewire 922 may be advanced further into a pulmonary vein or pulmonary vein branch for increased support. The expandable member 920 is then expanded to engage the tissue and anchor the ablation element 918 relative to the ostium 54 as illustrated in FIG. 28. Once the ablation element 918 is securely anchored by expansion of the expandable member 920, delivery of energy (e.g., thermal, RF, ultrasonic, electrical, etc.) is commenced to ablate at least the substantial portion of the circumferential region of tissue.

In a variation of this method, once the expandable member is engaged in the pulmonary vein ostium and the guidewire is positioned distally in the vein, the guidewire is retracted back into the tip of the ablation catheter. The deflectable tip portion is then manipulated such that the guidewire may be advanced distally into a different distal branch of the vein, thereby providing a different orientation of the ablation element to enhance alignment for ablation.

In another variation to this method, the deflectable tip portion can be deflected within the pulmonary vein after the expandable member has been expanded to engage the circumferential region of tissue. By deflecting the deflectable tip portion of the seated catheter, the orientation of the ablation element and the contact with the surrounding tissue can be altered to optimize ablation.

While a number of variations of the invention have been shown and described in detail, other modifications and methods of use contemplated within the scope of this invention will be readily apparent to those of skill in the art based upon this disclosure. It is contemplated that various combinations or subcombinations of the specific embodiments may be made and still fall within the scope of the invention. For example, the described embodiments are believed useful when modified to treat other tissues in the body, in particular other regions of the heart, such as the coronary sinus and surrounding areas. Further, the disclosed assemblies may be useful in treating other conditions, wherein aberrant electrical conduction may be implicated, such as for example, heart flutter. Indeed, other conditions wherein catheter-based, directed tissue ablation may be indicated, such as for example, in the ablation of fallopian tube cysts. Accordingly, it should be understood that various applications, modifications and substitutions may be made of equivalents without departing from the spirit of the invention or the scope of the following claims.

What is claimed is:

1. A method for placing a therapeutic or diagnostic device within a body structure comprising:
   providing a catheter with proximal and distal end portions and a guidewire lumen which extends along at least a portion of said distal end portion and terminates at a distal port, said catheter having said therapeutic or diagnostic device disposed on said distal end portion, said catheter having a deflectable tip located along said distal end portion, the deflectable tip being deflectable by manipulation of a pull wire;
   slidably engaging a guidewire within said guidewire lumen;
   advancing said distal end portion of said catheter into a patient's body;
   deflecting said deflectable tip such that said distal port is positioned to direct advancement of said guidewire toward said body structure;
   advancing said guidewire out of said distal port and toward said body structure; and
   advancing said catheter over said guidewire such that said therapeutic or diagnostic device is positioned at said body structure.

2. A method for placing a therapeutic or diagnostic device within a body structure comprising:
   providing a catheter with proximal and distal end portions and a guidewire lumen which extends along at least a portion of said distal end portion and terminates at a distal port, said catheter having said therapeutic or diagnostic device disposed on said distal end portion, said catheter having a deflectable tip located along said distal end portion, the deflectable tip being deflectable by manipulation of a pull wire;
   slidably engaging a guidewire within said guidewire lumen;
   advancing said distal end portion of said catheter into a patient's body;
   deflecting said deflectable tip such that said distal port is positioned to direct advancement of said guidewire toward said body structure;
   advancing said guidewire out of said distal port and toward said body structure;
   advancing said catheter over said guidewire such that said therapeutic or diagnostic device is positioned at said body structure; and
   anchoring said catheter to said body structure.

3. A method for placing a therapeutic or diagnostic device at a location where a pulmonary vein extends from an atrium:
   providing a catheter with proximal and distal end portions and a guidewire lumen which extends along at least a portion of said distal end portion and terminates at a distal port, said catheter having said therapeutic or diagnostic device disposed on said distal end portion, said catheter having a deflectable tip disposed along said distal end portion;
   slidably engaging a guidewire within said guidewire lumen;
   advancing said distal end portion of said catheter into an atrium;

deflecting said deflectable tip such that said distal port is positioned to direct advancement of said guidewire toward said location;

advancing said guidewire out of said distal port and toward said location;

advancing said catheter over said guidewire such that said therapeutic or diagnostic device is positioned at said location; and treating a region of tissue at said location.

* * * * *